United States Patent
Mak et al.

(10) Patent No.: US 10,168,317 B2
(45) Date of Patent: Jan. 1, 2019

(54) MICROFLUIDIC DEVICE, SYSTEM, AND METHOD FOR TRACKING SINGLE CELLS AND SINGLE CELL LINEAGES

(71) Applicant: CORNELL UNIVERSITY, Ithaca, NY (US)

(72) Inventors: Michael Mak, Boston, MA (US); David Erickson, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/406,310

(22) PCT Filed: Jun. 10, 2013

(86) PCT No.: PCT/US2013/044937
§ 371 (c)(1),
(2) Date: Dec. 8, 2014

(87) PCT Pub. No.: WO2013/185125
PCT Pub. Date: Dec. 12, 2013

(65) Prior Publication Data
US 2015/0140596 A1    May 21, 2015

Related U.S. Application Data

(60) Provisional application No. 61/657,555, filed on Jun. 8, 2012.

(51) Int. Cl.
*G01N 33/50* (2006.01)
*B01L 3/00* (2006.01)
(Continued)

(52) U.S. Cl.
CPC .... *G01N 33/5005* (2013.01); *B01L 3/502761* (2013.01); *G01N 33/5008* (2013.01);
(Continued)

(58) Field of Classification Search
CPC .......... G01N 33/5005; G01N 33/5008; G01N 33/574; G01N 2500/10; G01N 2800/52;
(Continued)

(56) References Cited

U.S. PATENT DOCUMENTS

2009/0093374 A1    4/2009    Suh et al.
2010/0170797 A1    7/2010    Arlett et al.

OTHER PUBLICATIONS

Chaw et al. (2007). Multi-step microfluidic device for studying cancer metastasis. Lab Chip, v7, p. 1041-1047; Reference U).*
(Continued)

*Primary Examiner* — Sean C. Barron
(74) *Attorney, Agent, or Firm* — FisherBroyles, LLP; Andrew K. Gonsalves, Esq.

(57) ABSTRACT

The present invention relates to a microfluidic device, a microfluidic system, and methods for tracking single cells, multiple cells, single cell lineages, and multiple cell lineages in series and/or in parallel. The microfluidic device comprises a substrate having one microfluidic channel formed therein or a plurality of microfluidic channels formed therein and arranged in parallel. The microfluidic system comprises: a microfluidic device according to the present invention; a cell loading reservoir in fluid communication with the inlet end of each microfluidic channel of the microfluidic device; and an outlet reservoir in fluid communication with the outlet end of each microfluidic channel of the microfluidic device. The present invention also relates to a high throughput microfluidic system and a kit for tracking single cells and/or single cell lineages.

25 Claims, 28 Drawing Sheets

(51) Int. Cl.
*G01N 33/574* (2006.01)
*C12M 3/06* (2006.01)

(52) U.S. Cl.
CPC .... *G01N 33/574* (2013.01); *B01L 2200/0668* (2013.01); *B01L 2300/087* (2013.01); *B01L 2300/0861* (2013.01); *B01L 2400/0457* (2013.01); *B01L 2400/086* (2013.01); *C12M 23/16* (2013.01); *G01N 2500/10* (2013.01); *G01N 2800/52* (2013.01)

(58) Field of Classification Search
CPC ......... B01L 3/502761; B01L 2400/086; B01L 2300/087; B01L 2200/0668; B01L 2400/0457; B01L 2300/0861
See application file for complete search history.

(56) References Cited

OTHER PUBLICATIONS

Hulkower et al. (2011). Cell Migration and Invasion Assays as Tools for Drug Discovery. Pharmaceutics, v3, p. 107-124.*
Echeverria et al. (2010). An Automated High-Content Assay for Tumor Cell Migration through 3-Dimensional Matrices. Journal of Biomolecular Screening, v15(9), p. 1144-1151.*
BioNumbers (Useful fundamental numbers in molecular biolog (2010), 2 pages plus appended pub. date from Internet Archive.*
International Search Report and Written Opinion issued in International Application No. PCT/US2013/044937, dated Sep. 13, 2013.
Rowat et al., "Tracking lineages of single cells in lines using a microfluidic device," *PNAS*, 106(43):18149-18154 (2009).
Lee et al., "Microfluidic system for automated cell-based assays," *Journal of Laboratory Automation*, 12(6):363-367 (2007).
Falconnet et al., "High-thoughput tracking of single yeast cells in a microfluidic imaging matrix," *Lab Chip*, 11(3):466-473 (2011).

* cited by examiner

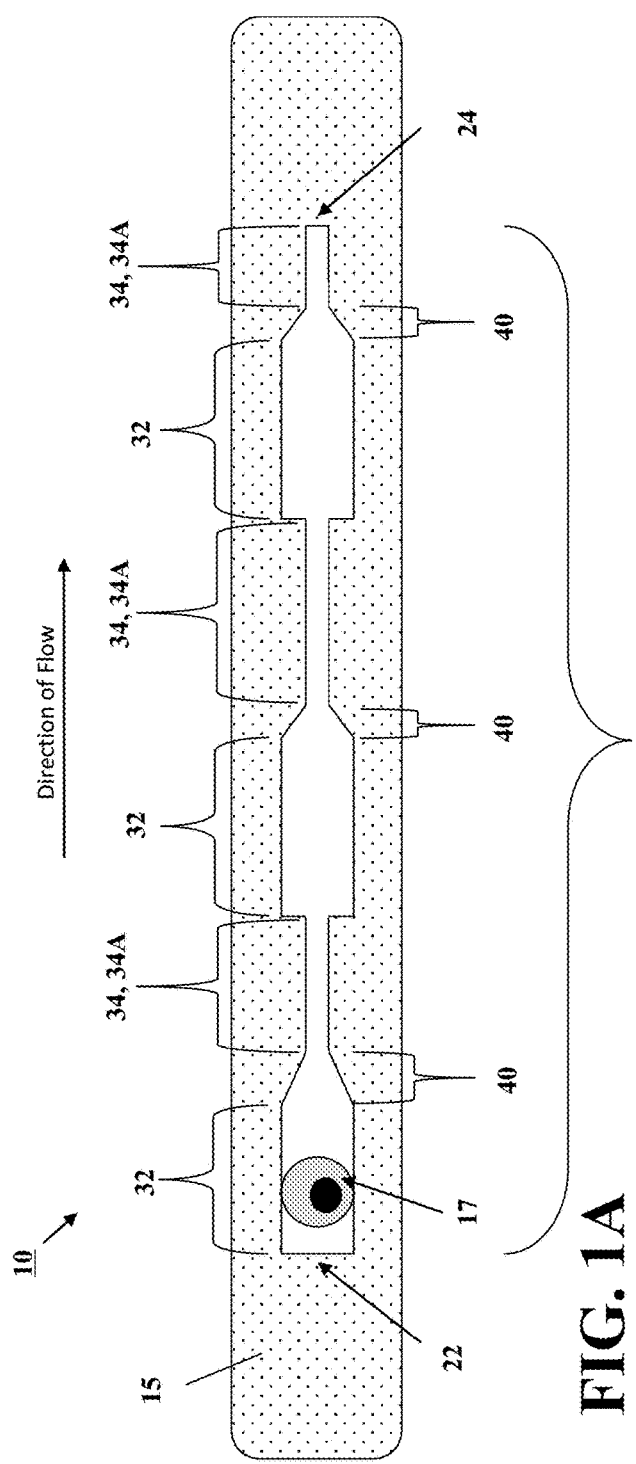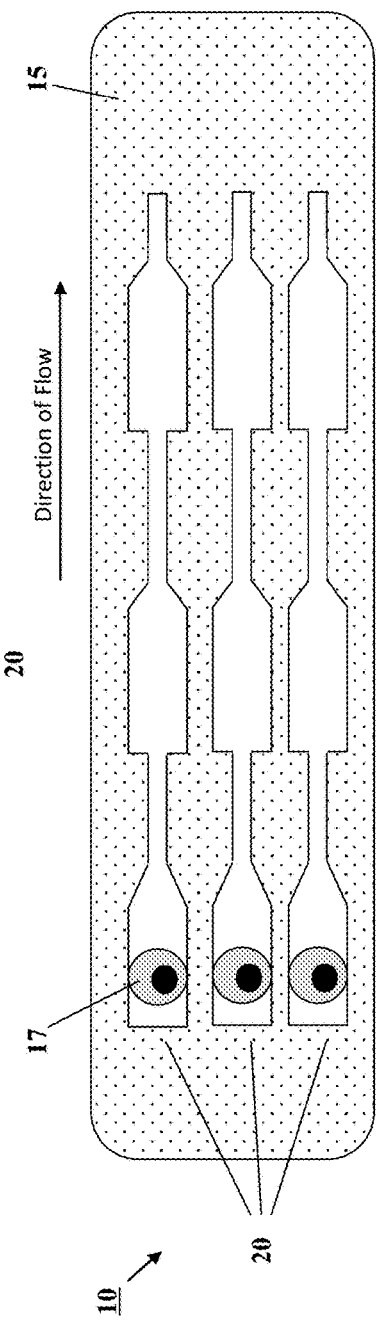
FIG. 1A
FIG. 1B

Plasticity in Morphology and Invasion Dynamics

Cell Behavior and Decision Making based on Mechanical Cues During Invasion

MICROFLUIDIC DEVICE, SYSTEM, AND METHOD FOR TRACKING SINGLE CELLS AND SINGLE CELL LINEAGES

CROSS-REFERENCE TO RELATED APPLICATIONS

This application is a U.S. National Phase filing under 35 U.S.C. § 371 of International Application No. PCT/US2013/044937, filed Jun. 10, 2013, and published as WO 2013/185125-A1 on Dec. 12, 2013, which claims priority benefit of U.S. Provisional Patent Application Ser. No. 61/657,555, filed Jun. 8, 2012, the entire disclosures of which are hereby incorporated by reference herein in their entirety.

GOVERNMENT RIGHTS STATEMENT

This invention was made with Government support under grant number U54CA143876 awarded by the National Institutes of Health and grant number ECS-9876771 awarded by the National Science Foundation. The United States Government has certain rights in the invention.

FIELD OF THE INVENTION

The present invention relates to microfluidic devices, microfluidic systems, methods, and kits for, inter alia, tracking single cells and single cell lineages.

BACKGROUND OF THE INVENTION

Cancer metastasis involves a series of mechanical events at the single-cell level. In order to invade to distal sites, aggressive cells must be able to squeeze across small spaces in the extracellular matrix (ECM) of the tumor stroma and endothelial barrier and circulate and traffic through microvessels smaller than the size of the cell (A. F. Chambers et al., *Nature Reviews Cancer*, 2002, 2, 563-572; P. Friedl et al., *Nature Reviews Cancer*, 2003, 3, 363-374; P. Friedl et al., *Current Opinion in Cell Biology*, 2011, 23, 55-64). Under such confined microenvironments, these cells must acquire deformed morphologies. There have been many studies on cell deformability, with techniques ranging from more conventional atomic force microscopy (AFM) (M. J. Rosenbluth et al., *Biophysical Journal*, 2006, 90, 2994-3003; M. P. Stewart et al., *Nat. Protocols*, 2012, 7, 143-154) and micropipette aspiration (MPA) (R. M. Hochmuth, *Journal of Biomechanics*, 2000, 33, 15-22) to more recent microfluidic systems with active (optical forces, hydrodynamic inertial focusing) (J. Guck et al., *Biophysical Journal*, 2005, 88, 3689-3698; I. Sraj et al., *Journal of Biomedical Optics*, 2010, 15, 047010-047010; D. R. Gossett et al., *Proc. Natl. Acad. Sci. USA*, 2012, 109, 7630-7635) and passive (microconstrictions) (S. Gabriele et al., *Biophysical Journal*, 2009, 96, 4308-4318; A. Adamo et al., *Analytical Chemistry*, 2012, 84, 6438-6443; W. Zhang et al., *Proceedings of the National Academy of Sciences*, 2012, 109, 18707-18712) deformation actuators. In particular, we are interested in deformations in the most extreme form observed in physiological systems— deformations at the subnucleus scale. This is important because such deformations are often observed in cell invasion through the ECM and in microcirculation (P. Friedl et al., *Current Opinion in Cell Biology*, 2011, 23, 55-64; K. Yamauchi et al., *Cancer Research*, 2005, 65, 4246-4252; P. Friedl et al., *Nat Rev Mol Cell Biol*, 2012, 13, 743-747; A. Pathak et al., *Integrative Biology*, 2011, 3, 267-278). These events in the metastatic process suggest that cell deformability is an important property in the context of cancer.

Recent work using microfluidic techniques has shown that deformability may be correlated with disease states in cells, metastatic potential, and stem cell differentiation (J. Guck et al., *Biophysical Journal*, 2005, 88, 3689-3698; D. R. Gossett et al., *Proc. Natl. Acad. Sci. USA*, 2012, 109, 7630-7635; W. Zhang et al., *Proceedings of the National Academy of Sciences*, 2012, 109, 18707-18712). Deformability in these cases is often measured by the aspect ratio of a cell under a fixed stress, such that more deformable cells exhibit a higher aspect ratio. Another common metric is the amount of time it takes a cell to flow through a microconstriction under pressure. These assays are typically high throughput and automated (have minimal manual operations) during measurements, which offer appeal towards clinical applications.

A key disadvantage of these high throughput microfluidic assays is that the information content is typically simplistic and does not fully appreciate the complexity of a biological phenomenon. In particular, the mechanical properties of cells are intrinsically complex in nature and heterogeneous. Not only does heterogeneity exist between different components of the cell, such as the cytoplasm, cytoskeleton, and nucleus, but heterogeneity exists even within the cytoskeletal and nucleoskeletal networks. As a result, a simple one-shot measurement of each cell (i.e. aspect ratio under asymmetric stress or average transit time across a barrier), while offering an appealing and simple assay, is a reductionist characterization of biological cells. Fundamental properties, such as creep strain dynamics, that are pertinent to the deformability of viscoelastic materials are difficult to measure with such techniques. As such, conventional, high resolution and more comprehensive measurements from traditional techniques such as AFM and MPA offer more detailed information about the state and fundamental properties of individual cells.

Micropipette aspiration and atomic force microscopy have been used to elucidate more complex phenomena associated with the mechanical properties of cells and nuclei. For instance, micropipette studies were able to produce high resolution data that revealed and enabled the development of mathematical models of the viscoelasticity of different cell types, which as an example characterized the distinction between solid like cells (endothelial cells) and liquid like cells (neutrophils) (R. M. Hochmuth, *Journal of Biomechanics*, 2000, 33, 15-22). Additionally, MPA of isolated cell nuclei identified the contributions of different subnucleus structures on force bearing properties under different conditions (swollen and unswollen nuclei) and further revealed that the creep compliance of the nucleus follows a power-law temporal dependence over time scales from 0.1 to 1000 seconds (K. N. Dahl et al., *Biophysical Journal*, 2005, 89, 2855-2864). AFM studies have also been critical in revealing local cell stiffness as well as cell forces and stress under compression and extension (M. P. Stewart et al., *Nat. Protocols*, 2012, 7, 143-154; D. A. Fletcher et al., *Nature*, 2010, 463, 485-492).

In these existing methods, there is a tradeoff between 1) experimental simplicity and automation and 2) the complexity of the measurable properties. More complex material properties such as cell strain dynamics during deformation and relaxation require more complicated procedures that are practicable typically only in labor intensive and bulky apparatuses (MPA and AFM) (M. J. Rosenbluth et al., *Biophysical Journal*, 2006, 90, 2994-3003; M. P. Stewart et al., *Nat. Protocols*, 2012, 7, 143-154; R. M. Hochmuth, *Journal of Biomechanics*, 2000, 33, 15-22), while more automated systems such as microfluidic constriction assays, optical stretchers, and inertial focusing methods produce static and reductionist measurements and are currently limited to simple experimental procedures (J. Guck et al., *Biophysical Journal*, 2005, 88, 3689-3698; I. Sraj et al., *Journal of Biomedical Optics*, 2010, 15, 047010-047010; D. R. Gossett et al., *Proc. Natl. Acad. Sci. USA*, 2012, 109, 7630-7635; S. Gabriele et al., *Biophysical Journal*, 2009, 96, 4308-4318; A. Adamo et al., *Analytical Chemistry*, 2012, 84, 6438-6443). The incorporation of more functionality in microfluidic assays often requires more manual labor or additional components such as robotic actuators for image-assisted flow modulation, thus reducing their automation or adding to their already bulky systems that require external pressure pumps and optical components (e.g. high power lasers). These tradeoffs limit the adoptability of the mentioned techniques and thus the practicability of the field of cell biomechanics to select experts in select settings. Mechanical properties such as cell deformability and viscoelasticity, however, are critical and complementary to many areas in cell biology, with implications in cancer metastasis, immune cell responses, tissue homeostasis, blood diseases, and stem cell differentiation (D. A. Fletcher et al., *Nature*, 2010, 463, 485-492; D. Discher et al., *Annals of biomedical engineering*, 2009, 37, 847-859; F. Lautenschläger et al., *Proceedings of the National Academy of Sciences*, 2009, 106, 15696-15701; S. Kumar et al., *Cancer and Metastasis Reviews*, 2009, 28, 113-127; M. J. Paszek et al., *Cancer Cell*, 2005, 8, 241-254; Y. Park et al., *Proceedings of the National Academy of Sciences*, 2010, 107, 6731-6736; D. A. Fedosov et al., *Proceedings of the National Academy of Sciences*, 2011, 108, 35-39; W. H. Grover et al., *Proceedings of the National Academy of Sciences*, 2011, 108, 10992-10996; J. P. Shelby et al., *Proceedings of the National Academy of Sciences*, 2003, 100, 14618-14622). Therefore there is a need for multifunctional, procedurally adept, and automated systems that require minimal labor and components in order to promote accessibility and technology adoption.

The present invention is directed to overcoming these and other deficiencies in the art.

SUMMARY OF THE INVENTION

The present invention generally relates to, inter alia, devices, systems, and methods that enable the tracking of single cells and single cell lineages.

In one aspect, the present invention relates to a microfluidic device for tracking single cells, multiple cells, single cell lineages, and multiple cell lineages in series and/or in parallel. The microfluidic device of the present invention comprises a substrate having one microfluidic channel formed therein or a plurality of microfluidic channels formed therein and arranged in parallel. Each microfluidic channel of the microfluidic device includes an inlet end, an opposing outlet end, and a channel portion. The inlet end functions to receive at least one cell and an accompanying fluidic medium into the microfluidic channel. The opposing outlet end functions to dispense of the fluidic medium flowing from the microfluidic channel and optionally to extract the at least one cell or a lineage of cells derived from the at least one cell from the microfluidic channel. The channel portion comprises at least one single cell-scaled region and at least one subcell-scaled constriction region disposed between the inlet end and the outlet end.

In one embodiment of the microfluidic device of the present invention, at least one of the microfluidic channels further comprises a narrowing tapered region between the single cell-scaled region and the subcell-scaled constriction region.

In another embodiment of the microfluidic device of the present invention, at least one of the microfluidic channels further comprises at least one growth chamber region for maintaining and/or proliferating a plurality of cells, where the at least one growth chamber has a volume sufficient to hold at least two, non-deformed cells.

In another aspect, the present invention relates to a microfluidic system for tracking single cells, multiple cells, single cell lineages, and multiple cell lineages in series and/or in parallel. The microfluidic system comprises: (i) a microfluidic device according to the present invention; (ii) a cell loading reservoir in fluid communication with the inlet end of each microfluidic channel of the microfluidic device; and (iii) an outlet reservoir in fluid communication with the outlet end of each microfluidic channel of the microfluidic device, where a flow path for a fluidic medium runs from the cell loading reservoir through the microfluidic channel and into the outlet reservoir.

In one embodiment, the microfluidic system of the present invention further comprises a microscopy system for observing cells or cell lineages contained in the microfluidic channels.

In another aspect, the present invention relates to a method for tracking at least one cell or cell lineage migrating through and/or incubating in a microfluidic channel having single cell-scaled and subcell-scaled regions. This method involves the following steps: (i) providing a microfluidic system according to the present invention; (ii) introducing at least one cell into a microfluidic channel of a microfluidic device of the microfluidic system; and (iii) viewing the at least one cell or cell lineage as it migrates through and/or incubates in the microfluidic channel.

In one embodiment of this method, the introducing step further involves generating a flow of the fluidic medium along the flow path of the microfluidic system, where the flow path runs from the cell loading reservoir through the microfluidic channel and into the outlet reservoir.

In another embodiment, this method further involves inducing and maintaining fluidic equilibrium along the flow path after the flow is discontinued.

In another embodiment, this method further involves removing unloaded cells from the cell loading reservoir to prevent additional individual cells from entering into a microfluidic channel that already contains an individual cell or individual cell lineage.

In another embodiment, this method further involves (i) extracting the cells or cell lineages from the microfluidic channels subsequent to viewing their behavior within the microfluidic channels; and (ii) optionally culturing the extracted cells or cell lineages.

In another aspect, the present invention relates to a method for tracking behavior of at least one cell or cell lineage in response to exposure to an agent of interest.

This method involves: (i) providing a microfluidic system according to the present invention; (ii) introducing at least one cell into a microfluidic channel of a microfluidic device of the microfluidic system; (iii) exposing the at least one cell or a cell lineage derived from the at least one cell to an agent of interest; and (iv) viewing the at least one cell or cell lineage in response to the agent as the at least one cell or cell lineage moves through or optionally incubates in the microfluidic channel. The agent of interest is introduced under conditions effective to expose the at least one cell or a cell lineage derived from the at least one cell to the agent.

In one embodiment, this method further involves identifying cells that are resistant to intended effects of the agent of interest and extracting the identified resistant cells from the microfluidic channels.

In another embodiment, the method further involves culturing the extracted resistant cells.

In another aspect, the present invention relates to a high throughput microfluidic system for tracking single cells and/or single cell lineages. The high throughput microfluidic system includes a plurality of microfluidic devices according to the present invention; a cell loading reservoir in fluid communication with the inlet end of each microfluidic channel of each microfluidic device; and an outlet reservoir in fluid communication with the outlet end of each microfluidic channel of each microfluidic device. A flow path for a fluidic medium runs from the cell loading reservoir through the microfluidic channel and into the outlet reservoir of each microfluidic device of the high throughput microfluidic system.

In another aspect, the present invention relates to a kit for tracking single cells and/or single cell lineages. The kit includes a microfluidic device or a plurality of microfluidic devices according to the present invention; and at least one kit component effective for integrating the microfluidic device into a microfluidic system that comprises a cell loading reservoir in fluid communication with the inlet end of the microfluidic channel of the microfluidic device and an outlet reservoir in fluid communication with the outlet end of the microfluidic channel of the microfluidic device.

The devices, systems, kits, and methods of the present invention provide various improvements and advantages over the prior art. For example, in one aspect of the present invention, mechanical barriers smaller than the cell nucleus (subnucleus barriers) are integrated into a confined microfluidic design. Cells are induced to migrate in 1-D along a confined microchannel comparable to the size of the cell. They then encounter patterns of subnucleus barriers that induce cell transition dynamics, changes in cell morphology, and boundary effects on cell division. These invasion dynamics and morphological effects can then be correlated with pharmacologic treatments, drug resistance, and other mechanical effects associated with the invasion phenomena and cancer metastasis, such as cell division asymmetry, small cell fractionalization from long extensions, and changes in cell phenotype (due to chemical or mechanical inputs).

In another aspect, the present invention provides a novel assay that introduces micro-architectures into highly confining microchannels to probe the decision making processes of migrating cells. The conditions are meant to mimic the tight spaces in the physiological environment that cancer cells encounter during metastasis within the matrix dense stroma and during intravasation and extravasation through the vascular wall. In one embodiment, the assay is used to investigate the relative probabilities of a cell 1) permeating and 2) repolarizing (turning around) when it migrates into a spatially confining region. Using the assay, one can observe the existence of both states even within a single cell line, indicating phenotypic heterogeneity in cell migration invasiveness and persistence. Varying the spatial gradient of the taper can induce behavioral changes in cells, and different cell types respond differently to spatial changes. For example, in a particular embodiment, for bovine aortic endothelial cells (BAECs), higher spatial gradients induce more cells to permeate (60%) than lower gradients (12%). Furthermore, highly metastatic breast cancer cells (MDA-MB-231) demonstrate a more invasive and permeative nature (87%) than non-metastatic breast epithelial cells (MCF-10A) (25%). The present invention enables one to examine the migration dynamics of cells in the tapered region and derive characteristic constants that quantify this transition process. Using the present invention, data was collected that indicated that cell response to physical spatial gradients is both cell-type specific and heterogeneous within a cell population, analogous to the behaviors reported to occur during tumor progression. Incorporation of micro-architectures in confined channels enables the probing of migration behaviors specific to defined geometries that mimic in vivo microenvironments.

In another aspect, the present invention provides devices, systems, and methods for elucidating mechanical phenomena/markers beyond just invasiveness. The present invention enables the analysis of morphological effects, impact on cell division, the functional role of invasion phases (extensions, rotations, deformations of the cell body and nuclei), and the plasticity in invasion mechanisms (varying time constants, different invasion morphologies—both of the same cell for multiple sampling as well as across different cells).

These events are elicited by having repeating patterns of the described subnucleus barrier of variable length. Repeats of the subnucleus barrier as well as repeats of the idea of "dimensional modulation" at predefined lengths allow for multiple sampling per cell as well as enabling the observation of morphological changes more clearly. In one embodiment, the devices, systems, and methods of the present invention do not rely on just one tapered region.

The present invention further provides a means for emphasizing the subnucleus length scale of the barrier because mechanical forces acting on the cell nucleus can potentially induce phenotypic changes in cells, and in these subnucleus barriers the invading cell nucleus has to deform substantially. In one embodiment, the present invention expands on the function of an embodiment that includes a tapered-channel device. For example, under the present invention, one can "filter" for cells that have invaded across the long confined subnucleus barrier and perform microarray tests that show at least preliminarily that those cells have a different gene expression profile. Thus, the present invention enables isolating cell populations with this approach, thereby enabling the study of, inter alia, heterogeneity in cell populations.

Additionally, using the present invention, it was demonstrated that very long cell extensions can be induced via dimensional modulation (i.e., by these subnucleus barriers). These extensions have then been observed to fractionalize into what appears to be mini-cells. This is another phenomenological event that is possible to induce via repeating patterns of the subnucleus barrier, and this could be another potential mechanical biomarker.

The assay of the present invention and related aspects are effective to assess the effects of chemotherapeutic drugs on the single-cell level, and emphasize on both the mechanical cell dynamics that can be studied as well as the "evolution" of single cells as indicated by morphological evolution during the course of an experiment in which the cell has been treated with the drug, failed to divide, undergone failed mitosis with disrupted cytoskeletal architecture, and recovered but with a new morphology. Confined microfluidic spaces allow for these events to be observed more easily. The present invention has been used to perform numerical simulations that showed that autologous chemotactic gradients may be inducible in confined dimensionally modulated spaces, so another function of the assay could be to study geometrically induced autologous chemotaxis.

In a particular aspect, the present invention provides a cell assay apparatus comprising a microfluidic confinement and barriers of the subnucleus length scale that can induce and facilitate measurements of cell invasion and effects and changes in cell state for the detection and discovery of cell features and biomarkers. In one embodiment the biomarkers can included, without limitation, including cell plasticity, morphological effects, invasion dynamics, cell division, directed evolution, heterogeneous subpopulations, and chemotaxis.

The present invention provides devices, systems, and methods that enable one to explore and better quantify dynamic and mechanical events exhibited during the invasion process. In a particular embodiment, using dimensional modulation in a microfluidic platform, the present invention enables one to elucidate the cell invasion program in a high throughput manner, and quantify higher order mechanical dynamics, interface induced morphological effects, and the impacts of microtubule stabilization and drug resistance during invasion. Here, higher order refers to terms above the $1^{st}$ order approximation of the cell displacement function ($0^{th}$ order being fixed displacement, and $1^{st}$ order being the velocity term).

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIGS. 1A-1D are schematic drawings of top views of various embodiments of a microfluidic device of the present invention. FIG. 1A illustrates a microfluidic device having one microfluidic channel formed in a substrate. FIG. 1B illustrates a microfluidic device having a plurality of microfluidic channels formed in a substrate. FIG. 1C illustrates a microfluidic device having one microfluidic channel formed in a substrate and including inlet and outlet adapters for fitting a cell loading reservoir and an outlet reservoir onto the microfluidic device. FIG. 1D illustrates a microfluidic device having a plurality of microfluidic channels formed in a substrate and including inlet and outlet adapters for fitting a cell loading reservoir and an outlet reservoir onto the microfluidic device.

FIG. 4A: The dynamics of a cell invading across subnucleus barriers can be segmented into 4 phases, as shown in the timelapse image stack (17 min/frame). The cell slows down as it reaches the barrier (phase 1), the cell body starts permeating into the barrier (phase 2), the cell pauses or otherwise stops monotonic forward motion (phase 3), and the cell resumes monotonic forward motion and exits the barrier (phase 4). FIG. 4B: The average time constants for these phases are measured for invasions across the subnucleus barriers SNB10 (n=62) and SNB60 (n=20), where n is the number of invasion events observed. The width of the larger channel is 15 μm.

FIG. 5A: The probability of phase 3 existing for the two different subnucleus barriers SNB10 and SNB60. SNB60 induces a higher probability of phase 3 existing (70%, n=20) than SNB10 (19.4%, n=62). Error bars represent standard error of the mean (s.e.m.) from Bernoulli statistics and *** indicates p<0.001 (Chi-squared test). FIG. 5B: A timelapse image stack (17 min/frame) showing a cell invading across SNB10 with no phase 3 observed. The contractile force of the cell is enough to deform the cell nucleus across the barrier in a monotonic forward motion. FIG. 5C: As this cell invades from top to bottom across SNB60, a stiff aggregate at the rear of the cell is stuck at the barrier interface. A back extension is protruded, which tensionally reduces the width of the aggregate and facilitates intracellular trans-barrier transport. 34 minutes elapsed between subsequent frames. FIG. 5D: As this cell is invading from the LC into SNB60, cell body rotations, with visualization facilitated by endocytosed particles, can be seen in the timelapse image stack during the invasion process. These rotational dynamics may help position the cell more favorably and/or sample more energetically favorable conformations as the cell is invading across the subnucleus barrier. 34 minutes elapsed between subsequent frames. The width of the larger channel is 15 μm.

FIG. 6A: Taxol-treated (1604) MDA-MB-231 cells take much longer to permeate across the subnucleus barriers than untreated MDA-MB-231 cells. The total invasion times are 0.86 hrs (n=62 invasion events), 3.33 hrs (n=20 invasion events), 22 hrs (n=42 invasion events), 22 hrs (n=31 invasion events), for untreated cells across SNB10, untreated cells across SNB60, taxol-treated cells across SNB10, and taxol-treated cells across SNB60, respectively. Many of the taxol-treated cells have yet to permeate through the subnucleus barrier by the end of the experiments, so the data represents a lower-bound measurement. Cells that have not permeated by the end of the experiments were only accounted for if they have spent at least 4 hrs at the barrier. This way we have disregarded arbitrarily short lower-bound measurements for data that was truncated too early (less than 4 hrs). Inset: the average speed of untreated (0.93 μm/min, n=12) and 1604 taxol-treated (0.53 μm/min, n=10) MDA-MB-231 cells in the larger channel LC during a 3.4 minute time interval. Error bars are s.e.m. FIG. 6B: Log-log plot of the average normalized mean-squared displacements (MSD) vs. time for untreated (black circles, n=12 cells) and taxol-treated cells (red squares, n=10 cells) in the larger channel LC. Normalization is with respect to the first data point (3.4 minute time interval) of each cell. Error bars are s.e.m. A non-linear least squares fit to a power-law model shows a dependence of $t^{1.667}$ ($R^2$: 0.996, 95% confidence [1.66, 1.673]) and $t^{1.014}$ ($R^2$: 0.9829, 95% confidence [1.006, 1.022]) for untreated and taxol-treated MDA-MB-231 cells, respectively. For Brownian motion, MSD $\propto$ t.

FIG. 7A: The average cell extension length measured at a random point in time for MDA-MB-231 cells in the larger channel LC (53 µm, n=42 cells), while interacting with SNB10 (85 µm, n=50 cells), while interacting with SNB60 (95 µm, n=45 cells), and K20T cells in the LC (109 µm, n=35 cells). Extension lengths are measured from the center of the cell body to the end of the longest extension. The subnucleus barrier induces longer cell extensions and K20T cells also have longer cell extensions.  represents p<0.01 and * represents p<0.001 from ANOVA statistics. FIG. 7B: Histograms and typical cell morphologies at each scenario. The width of the larger channel is 15 µm.

FIG. 10A: The user simply pipettes the sample of interest into the inlet reservoir (left) and gravity drives the flow, enabling the device to operate without any external pressure actuators. Cells are automatically driven to the micropipette constrictions (inset). FIG. 10B: After sample loading, the multi-step serial cell deformation experiments are performed automatically with no manual input required.

FIG. 11A: Individual untreated and taxol treated cells were driven via pressure driven flow to permeate across sequential subnucleus-scaled constrictions. Taxol treated cells are larger (length=31±2 µm, n=26) (inset) and require a longer transit time across the first constriction (550±109s, n=26) than untreated cells (length=22±0.9 µm, n=36; transit time 1=254±59s, n=34). For both cell groups, the initial transit requires the longest time. Subsequent transits are faster and the difference between the two cell groups is reduced. The number of cells n examined in subsequent transit events ranged from 20 to 40. * denotes p<0.01. FIG. 11B: The transit times across the third, fourth, and fifth constrictions are normalized by the transit time across the second constriction of the same cell. Transit times are further reduced at subsequent constrictions after the second permeation. * denotes p<0.01 when compared to unity. Error bars are s.e.m.

FIG. 12A: The same MDA-MB-231 cell is deformed across multiple microconstrictions (3.3 µm×10 µm×60 µm) in series in the serial micropipette device. Subsequent transits are faster and display altered strain dynamics. The cell is allowed to relax before subsequent deformations, as described in the text, and the extent of their relaxed state right before the next deformation event is displayed in the corresponding pictures (on the label). In the first transit, multiple phases are exhibited in the strain dynamics—an initial rapid phase, followed by a stagnant phase, and a moderate rate final phase. FIG. 12B: More details about the strain dynamics of the first transit are elucidated when considering the transit dynamics of the cell nucleus, as shown here with a live nucleus stain. The image is a kymograph along the center of the micropipette constriction (longitudinal axis vs. time). Simultaneous phase contrast and fluorescence imaging help display the cell boundaries, the nucleus, and the constriction. This enables a more comprehensive consideration of the contributing elements in the phases of cell deformation dynamics. As shown, phase 1 is the initial cell response to a fixed stress from the external pressure, phase 2 is when the stiff cell nucleus is obstructed at the entry of the constriction due to insufficient pressure but viscoelastic creep enables slow permeation, and during phase 3 the nucleus has sufficiently deformed (partially) into the constriction leading to an increase in subsequent strain rate. FIG. 12C: The subsequent transit for the same cell as in FIG. 12B displays a faster strain rate without prolonged nucleus obstruction at the constriction interface. Both the cell boundaries and the nucleus deform into the constriction more quickly. For scale reference, the length of the constriction is 60 µm.

As shown in FIG. 17D, cells are shown migrating in the tapered microchannel device, which simulates physiological spatial gradients encountered by cells during the metastatic process. The width of the larger channel is 15 µm.

FIG. 18A: Image of actual device tapered microchannels from brightfield microscopy. Larger channels (15 µm×10 µm) are connected to smaller channels (4 µm×10 µm) via a tapered junction. The tapering angles are 1, 2, 3, 7, 15, and 40 degrees from low to high. The first three junctions are considered "low gradients" and the last three are considered "high gradients." Scale bar 100 µm. FIG. 18B: Schematic of fabrication procedure. Standard contact photolithography is used to pattern SU8 masters which are then used in PDMS soft lithography to generate microchannels.

FIGS. 21A-21B: Timelapse image stack (FIG. 21A) juxtaposed on top of the data and sigmoid curve fit of the velocity profile on the same time interval (FIG. 21B) of a permeating MDA-MB-231 cell during transition in the tapered junction. The time constants for the first and second sigmoidal curves are approximately 6 and 3 minutes, respectively, and the delay constant is 1 hour. $R^2$ of the fit is 0.7. FIGS. 21C-21D: Timelapse image stack (FIG. 21C) juxtaposed on top of the data and sigmoid curve fit of the velocity profile on the same time interval (FIG. 21D) of a repolarizing MCF-10A cell during transition in the tapered junction. The time constants for the first and second sigmoidal curves are both approximately 10 minutes, and the delay constant is 2 hours. $R^2$ of the fit is 0.94.

FIG. 29A: MDA-MB-231 metastatic breast cancer cells treated with the chemotherapeutic taxol exhibit a less extended, more rounded morphology. However, after failed mitosis due to microtubule disruption from taxol, the cells recover a more extended morphology. FIG. 29B: This more extended morphology from taxol-treated cells after failed mitosis resembles the morphology of K20T cells, which are the taxol-resistant variant of the MDA-MB-231 cells.

DETAILED DESCRIPTION OF THE INVENTION

Figure 1C:
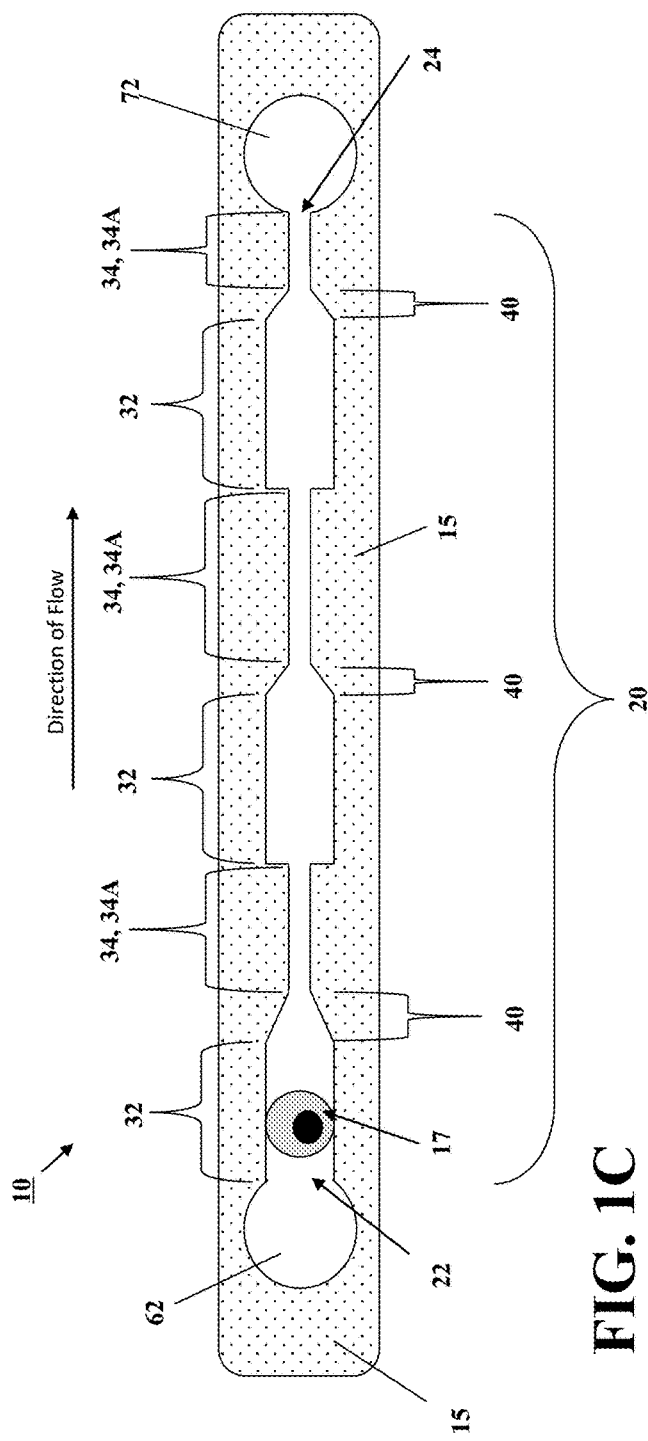

The present invention generally relates to, inter alia, devices, systems, and methods that enable the tracking of single cells and single cell lineages. For example, the devices, systems, and methods of the present invention can be used for applications such as: (i) loading a single cell into a single microfluidic channel in a highly parallel manner such that many parallel microfluidic channels are loaded with one cell each; (ii) enabling each single cell loaded into isolated single microfluidic channels to proliferate into isolated single-cell lineages; (iii) tracking of invasion dynamics, proliferation, and drug and molecular effects on isolated single-cells and single-cell lineages; (iv) tracking the emergence of drug resistance from single-cells and single-cell lineages; (v) tracking heterogeneous responses to drug treatment of single-cells and single-cell lineages; (vi) tracking the evolutionary dynamics of single-cells and single-cell lineages in parallel; and (vii) tracking the phenotypic or morphological traits that are passed on to progenies of the same single-cell lineage. Further, the devices, systems, and methods of the present invention can be used for tracking multiple single-cells and single-cell lineages in parallel, as multiple single-cells and single-cell lineages are isolated in parallel in the devices of the present invention. For example, each microfluidic channel of a parallel array of microfluidic channels can be loaded with one cell which can then proliferate and propagate into single-cell progenies that are all localized and isolated along the same microfluidic channel. In addition, the devices and systems of the present invention can be scaled up and incorporated into multi-well (e.g., 96-well) plate formats, e.g., when multiple devices are incorporated on the same plate or slide.

Microfluidic Devices, Microfluidic Systems, and Microfluidic Kits

In one aspect, the present invention relates to a microfluidic device for tracking single cells, multiple cells, single cell lineages, and multiple cell lineages in series and/or in parallel. The microfluidic device of the present invention comprises a substrate having one microfluidic channel formed therein or a plurality of microfluidic channels formed therein and arranged in parallel. Each microfluidic channel of the microfluidic device includes an inlet end, an opposing outlet end, and a channel portion. The inlet end functions to receive at least one cell and an accompanying fluidic medium into the microfluidic channel. The opposing outlet end functions to dispense of the fluidic medium flowing from the microfluidic channel and optionally to extract the at least one cell or a lineage of cells derived from the at least one cell from the microfluidic channel. The channel portion comprises at least one single cell-scaled region and at least one subcell-scaled constriction region disposed between the inlet end and the outlet end.

The microfluidic device can be configured so that the at least one cell can be received into the microfluidic channel as a single cell at a time or as a plurality of cells in close proximity to one another. Therefore, in one embodiment, a single cell can be interrogated or analyzed in the microfluidic channel, and in another embodiment more than one cell can be interrogated or analyzed in the same microfluidic channel.

In one embodiment, the at least one single cell-scaled region has a cross-sectional shape and dimension effective to allow only a single cell to move along a given portion of the single cell-scaled region at a time. For example, in a particular embodiment, even if more than one cell were contained in the same single cell-scaled region, the second cell into the region would not be able to pass the first cell into the region, due to the cross-sectional shape and dimension of the region not providing sufficient space for the second cell to pass the first cell. In a particular embodiment, the cells in the microfluidic channel are prompted to move into the inlet end of the microfluidic channel by generating a flow of the fluidic medium into the microfluidic channel. The flow can be created by various means, including, without limitation, by inducing a pressure gradient flowing from the inlet end to the outlet end of the microfluidic channel, by gravity, by establishing an electric field, etc. In certain embodiments, cells move into the microfluidic channel without the aid of a flow (e.g., by "crawling" into the microfluidic channel). In certain embodiments, after cell loading, the microfluidic device can be equilibrated so there is no longer any flow, thereby enabling the study of cell dynamics when the microfluidic device is in equilibrium.

As used herein, the term "subcell-scaled constriction region" refers to any region of the microfluidic channel that has a smaller diameter than the single cell-scaled region. The subcell-scaled constriction region functions to at least cause a single cell to deform from its normal three-dimensional geometry. In certain embodiments, the subcell-scaled constriction region can have a diameter that is smaller than that of the single cell-scaled region but larger than the diameter of the cell's nucleus. In other embodiments, the subcell-scaled constriction region can have a diameter that is smaller than the diameter of the cell's nucleus, and is referred to herein as a "subnucleus-scaled constriction region." The "subnucleus-scaled constriction region" is also referred to herein by other terms, but one of ordinary skill in the art will readily recognize when such other terms are referring to the subnucleus-scaled constriction region (e.g., the term uses the word "subnucleus" or the like).

In one embodiment, the at least one subcell-scaled constriction region has a cross-sectional shape and dimension effective to cause a single cell to undergo a deformation stage due to size exclusion when the single cell comes into contact with the subcell-scaled constriction region.

The substrate of the microfluidic device can be made of any material or combination of materials suitable for use in providing microfluidic channels that can allow living cells to migrate through or incubate in the microfluidic channels. In one embodiment, the substrate comprises a material that is sufficiently transparent to enable viewing of the at least one cell or lineage of cells derived from the at least one cell as they migrate through or incubate in the microfluidic channel or plurality of microfluidic channels. In one embodiment, a suitable material for use in making the substrate can be a polymeric material. Examples of suitable polymeric materials for use as the substrate can include, without limitation, polymethylmethacrylate (PMMA), polycarbonate, polytetrafluoroethylene, polyvinylchloride (PVC), polydimethylsiloxane (PDMS), polysulfone, and the like.

Various microfluidic device fabrication methods can be used to make the microfluidic device of the present invention, including, without limitation, standard photolithography and soft lithography techniques. In a particular embodiment, standard stepper photolithography can be used on a resist (e.g., SU8 resist) on a silicon substrate followed by PDMS-soft lithography.

In one embodiment, at least one of the microfluidic channels comprises a serial microfluidic channel region comprising multiple, alternating single cell-scaled regions and subcell-scaled constriction regions.

The subcell-scaled constriction regions of the serial microfluidic channel region can have the same or different dimensions, in that their length, width, and height can be the same or different, as long as they conform to the requirement that they are subcell-scaled (i.e., smaller than the diameter of the cell or cells being studied or used in the microfluidic device).

In one embodiment, the plurality of microfluidic channels arranged in parallel have serial microfluidic channel regions that are the same, substantially the same, or different in terms of the numbers and dimensions of the alternating single cell-scaled regions and subcell-scaled constriction regions.

In one embodiment, the cross-sectional shape of the single cell-scaled region and the subcell-scaled constriction region is selected from the group consisting of a rectangle, a square, a circle, an oval, a triangle, and any other polygonal shape.

In a particular embodiment, the single cell-scaled region has a cross-sectional shape of a rectangle having a width of between about 10 and about 50 micrometers and a height of between about 10 and about 50 micrometers. More particularly, the single cell-scaled region can have a cross-sectional shape of a rectangle having a width of about 15 micrometers and a height of about 10, or having a width of about 10 micrometers and a height of about 15 micrometers.

In one embodiment, the subcell-scaled constriction region has a cross-sectional shape of a rectangle having a width of between about 1 and about 30 micrometers and a height of between about 1 and about 30 micrometers. More particularly, the subcell-scaled constriction region can have a cross-sectional shape of a rectangle having a width of about 3 micrometers and a height of about 10, or having a width of about 10 micrometers and a height of about 3 micrometers. In another more particular embodiment, the subcell-scaled constriction region can have a cross-sectional shape of a rectangle having a width of about 3.3 micrometers and a height of about 10, or having a width of about 10 micrometers and a height of about 3.3 micrometers.

In one embodiment, the single cell-scaled region has a cross-sectional shape of a rectangle having a width of about 15 micrometers and a height of about 10 micrometers, and the subcell-scaled constriction region has a cross-sectional shape of a rectangle having a width of about 3.3 micrometers and a height of about 10 micrometers.

The length of the single cell-scaled regions and the length of the subcell-scaled constriction regions can be the same or different within a single microfluidic channel, and can be the same or different in parallel microfluidic channels. In a particular embodiment, the length of the single cell-scaled region can range from between about 10 micrometers and about 1,000 micrometers, and the length of the subcell-scaled constriction region can range from between about 10 micrometers and about 1,000 micrometers. However, the present invention also contemplates microfluidic channels, single cell-scaled regions, and subcell-scaled constriction regions having lengths that are longer than 1,000 micrometers, depending on the application of the microfluidic device and microfluidic system of the present invention. In further embodiments, the length of the single cell-scaled region and the subcell-scaled constriction region can range, without limitation, from between about 10 micrometers and about 750 micrometers, from between about 10 micrometers and about 500 micrometers, from between about 10 micrometers and about 400 micrometers, from between about 10 micrometers and about 300 micrometers, from between about 10 micrometers and about 200 micrometers, from between about 10 micrometers and about 150 micrometers, from between about 10 micrometers and about 100 micrometers, from between about 10 micrometers and about 90 micrometers, from between about 10 micrometers and about 80 micrometers, from between about 10 micrometers and about 70 micrometers, from between about 10 micrometers and about 60 micrometers, from between about 10 micrometers and about 50 micrometers, from between about 10 micrometers and about 40 micrometers, from between about 10 micrometers and about 30 micrometers, from between about 10 micrometers and about 25 micrometers, from between about 10 micrometers and about 20 micrometers, and from between about 10 micrometers and about 15 micrometers.

In one embodiment of the microfluidic device of the present invention, at least one of the microfluidic channels further comprises a narrowing tapered region between the single cell-scaled region and the subcell-scaled constriction region. The tapered region can be of various tapering angles. The tapered regions can have the same or different tapering angles. In certain embodiments, the tapering angle of the tapered regions can ranging from "high" gradients of tapering angles that are larger than 7 degrees to "low" gradients of tapering angles that are smaller than 3 degrees. In particular embodiments, the tapering angles can include, without limitation, 1, 2, 3, 7, 15, 20, 25, 30, 35, and 40 degrees from low to high.

Figure 25:
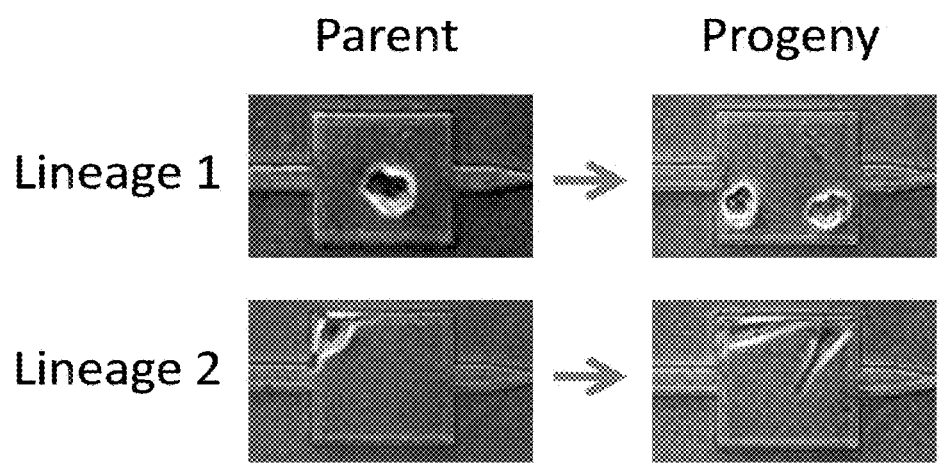
FIG. 25 illustrates a certain motile, morphological, and other phenotypic attributes are passed on from parent to daughter cells, as observed in one embodiment of a microfluidic device/microfluidic system of the present invention, with the microfluidic channel including one embodiment of a growth chamber as described herein. Lineages 1 and 2, both from the same MDA-MB-231 bulk population, display different inheritable phenotypes. Single-cell lineage tracking is facilitated by parallel chambers. Here, an additional, larger, growth chamber is incorporated into the single-cell microfluidic channels to enable single cells to grow and single-cell lineages to be tracked more easily over a larger and localized region. Single-cell lineage 1 displays a rounded morphology and that morphology is maintained in the daughter cells. Similarly, lineage 2 displays a spindle-shaped morphology that is maintained in the daughter cells.

In another embodiment of the microfluidic device of the present invention, at least one of the microfluidic channels further comprises at least one growth chamber region for maintaining and/or proliferating a plurality of cells, where the at least one growth chamber has a volume sufficient to hold at least two, non-deformed cells. An illustrative example of a suitable growth chamber is found in FIG. 25. However, the present invention contemplates that the growth chamber can be of any geometric shape, as long as it can contain more than one cell at the same time.

Various illustrative embodiments of the microfluidic device of the present invention are shown in FIGS. 1A-1D.

Referring to FIG. 1A, there is shown microfluidic device 10 comprising substrate 15 having one microfluidic channel 20 formed therein. Microfluidic channel 20 of microfluidic device 10 includes inlet end 22, opposing outlet end 24, and a channel portion comprising single cell-scaled regions 32 and subcell-scaled constriction regions 34 (also shown as subnucleus-scaled constriction regions 34A) disposed between inlet end 22 and outlet end 24 of microfluidic channel 20. In addition, narrowing tapered regions 40 are contained between single cell-scaled regions 32 and subcell-scaled constriction regions 34 (also shown as subnucleus-scaled constriction regions 34A). As shown in FIG. 1A, a single cell 17 is illustrated as being in the first single cell-scaled region 32 after having entered microfluidic channel 20 through inlet end 22. The direction of flow is indicated by an arrow flowing from left to right of microfluidic channel 20, i.e., from inlet end 22 toward outlet end 24. While the embodiment of microfluidic device 10 shows outlet end 24 terminating as a subcell-scaled constriction region 34 (also shown as subnucleus-scaled constriction region 34A), the microfluidic devices of the present invention can also terminate at their outlet ends as single cell-scaled regions and/or as narrowing tapered regions, as well as subcell-scaled constriction regions.

Referring to FIG. 1B, there is shown microfluidic device 10 comprising substrate 15 having a plurality of microfluidic channels 20 formed therein and arranged in parallel. Microfluidic channels 20 are shown to have the same configuration as the microfluidic channel illustrated in FIG. 1A. However, this is only for illustrative purposes and is not meant to limit the microfluidic device of the present invention to such a configuration. As shown in FIG. 1B, single cells 17 are illustrated as being in each microfluidic channel 20. The direction of flow is indicated by an arrow flowing from left to right of microfluidic channels 20, i.e., from the inlet end toward the outlet end of each microfluidic channel 20. While the embodiment of microfluidic device 10 shows three microfluidic channels 20, the microfluidic devices of the present invention can have any number of microfluidic channels arranged in parallel with one another, and can have different configurations in terms of their serial arrangement and parallel arrangement, as provided herein.

Referring to FIG. 1C, there is shown microfluidic device 10 comprising substrate 15 having one microfluidic channel 20 formed therein. Microfluidic channel 20 of microfluidic device 10 includes inlet end 22, opposing outlet end 24, and a channel portion comprising single cell-scaled regions 32 and subcell-scaled constriction regions 34 (also shown as subnucleus-scaled constriction regions 34A) disposed between inlet end 22 and outlet end 24 of microfluidic channel 20. In addition, narrowing tapered regions 40 are contained between single cell-scaled regions 32 and subcell-scaled constriction regions 34 (also shown as subnucleus-scaled constriction regions 34A). Further, as shown in FIG. 1C, inlet adapter 62 is formed in substrate 15 and in fluid communication with inlet end 22 of microfluidic channel 20. Inlet adapter 62 functions as an adapter for fitting and installing the cell loading reservoir when incorporating microfluidic device 10 into a microfluidic system of the present invention. Inlet adapter 62 may also itself function as a cell loading reservoir of the microfluidic system of the present invention. Further, as shown in FIG. 1C, outlet adapter 72 is formed in substrate 15 and in fluid communication with outlet end 24 of microfluidic channel 20. Outlet adapter 72 functions as an adapter for fitting and installing the outlet reservoir when incorporating microfluidic device 10 into a microfluidic system of the present invention. Outlet adapter 72 may also itself function as an outlet reservoir of the microfluidic system of the present invention. As shown in FIG. 1C, a single cell 17 is illustrated as being in the first single cell-scaled region 32 after having entered microfluidic channel 20 through inlet end 22 from inlet adapter 62. The direction of flow is indicated by an arrow flowing from left to right of microfluidic channel 20, i.e., from inlet end 22 toward outlet end 24. While the embodiment of microfluidic device 10 shows outlet end 24 terminating as a subcell-scaled constriction region 34 (also shown as subnucleus-scaled constriction region 34A), the microfluidic devices of the present invention can also terminate at their outlet ends as single cell-scaled regions and/or as narrowing tapered regions, as well as subcell-scaled constriction regions. Further, while inlet adapter 62 and outlet adapter 72 are shown as having a circular shape, the present invention is not meant to be limited by any particular shape for the inlet and outlet adapters.

Figure 1D:
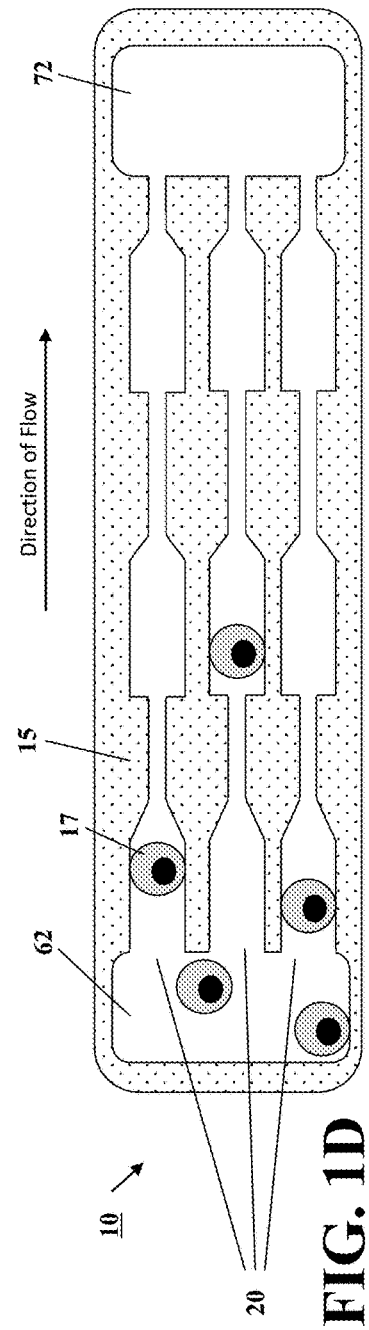

Referring to FIG. 1D, there is shown microfluidic device 10 comprising substrate 15 having a plurality of microfluidic channels 20 formed therein and arranged in parallel. Microfluidic channels 20 are shown to have the same configuration as the microfluidic channel illustrated in FIG. 1A. However, this is only for illustrative purposes and is not meant to limit the microfluidic device of the present invention to such a configuration. Further, as shown in FIG. 1D, inlet adapter 62 is formed in substrate 15 and in fluid communication with the inlet end of each microfluidic channel 20. Inlet adapter 62 functions as an adapter for fitting and installing the cell loading reservoir when incorporating microfluidic device 10 into a microfluidic system of the present invention. Inlet adapter 62 may also itself function as a cell loading reservoir of the microfluidic system of the present invention. Further, as shown in FIG. 1D, outlet adapter 72 is formed in substrate 15 and in fluid communication with the outlet end of each microfluidic channel 20. Outlet adapter 72 functions as an adapter for fitting and installing the outlet reservoir when incorporating microfluidic device 10 into a microfluidic system of the present invention. Outlet adapter 72 may also itself function as an outlet reservoir of the microfluidic system of the present invention. As shown in FIG. 1D, single cells 17 are illustrated as being in each microfluidic channel 20 after entering through the inlet ends of the microfluidic channels 20 from inlet adapter 62. The direction of flow is indicated by an arrow flowing from left to right of microfluidic channel 20, i.e., from the inlet end toward the outlet end. While the embodiment of microfluidic device 10 shows three microfluidic channels 20, the microfluidic devices of the present invention can have any number of microfluidic channels arranged in parallel with one another, and can have different configurations in terms of their serial arrangement and parallel arrangement, as provided herein.

In another aspect, the present invention relates to a microfluidic system for tracking single cells, multiple cells, single cell lineages, and multiple cell lineages in series and/or in parallel. The microfluidic system comprises: (i) a microfluidic device according to the present invention; (ii) a cell loading reservoir in fluid communication with the inlet end of each microfluidic channel of the microfluidic device; and (iii) an outlet reservoir in fluid communication with the outlet end of each microfluidic channel of the microfluidic device, where a flow path for a fluidic medium runs from the cell loading reservoir through the microfluidic channel and into the outlet reservoir.

In one embodiment, the cell loading reservoir is configured to hold a population of cells in a fluidic medium. Suitable cell loading reservoirs can include any chamber or chamber-like structure suitable for holding a fluidic medium in a quantity sufficient to contain at least one cell or a plurality of cells. The chamber or chamber-like structure can be designed to feed the fluidic medium into the inlet end of the microfluidic channel of the microfluidic device. The cell loading reservoir can be made of any material that can hold such a fluidic medium. Suitable materials for use as the cell loading reservoir can include, but are not limited to, polymeric materials, gels, and the like. In other embodiments, the cell loading reservoir can be any manual or automatic loading device (e.g., syringe, micropipette, pumping system, etc.) that can be placed in fluid communication with the inlet end of the microfluidic channel or channels of the present invention, and function to feed a fluidic medium and at least one cell or a plurality of cells into the inlet end of the microfluidic channel or channels of the microfluidic device of the present invention.

In one embodiment, the outlet reservoir is configured to hold one or more cells or cell lineages dispensed from the microfluidic channel or microfludic channels. Suitable outlet reservoirs can include any chamber or chamber-like structure suitable for holding a fluidic medium in a quantity sufficient to contain at least one cell or a plurality of cells, and sufficient to allow for establishing a pressure gradient or equilibrating the pressure of the fluidic medium in the microfluidic system when combined with a cell loading reservoir. The chamber or chamber-like structure can be designed to receive the fluidic medium from the outlet end of the microfluidic channel of the microfluidic device. The outlet reservoir can be made of any material that can hold such a fluidic medium. Suitable materials for use as the outlet reservoir can include, but are not limited to, polymeric materials, gels, and the like. In other embodiments, the outlet reservoir can be any dispensing device (e.g., test tube, beaker, laboratory tubing, syringe tube, micropipette, etc.) that can be placed in fluid communication with the outlet end of the microfluidic channel or channels of the present invention, and function to receive a fluidic medium (and optionally at least one cell or a plurality of cells) from the outlet end of the microfluidic channel or channels of the microfluidic device of the present invention.

In one embodiment, the microfluidic system of the present invention further comprises a microscopy system for observing cells or cell lineages contained in the microfluidic channels.

In another embodiment of the microfluidic system, the microscopy system is effective for observing the cells or cell lineages in contemporaneous real-time as they migrate and/or incubate in the microfluidic channels.

In a further embodiment of the microfluidic system, the microscopy system is a video microscopy system effective in creating real-time videos, timelapse images, and/or static images of the cells or cell lineages as they migrate and/or incubate in the microfluidic channels.

In another aspect, the present invention relates to a high throughput microfluidic system for tracking single cells and/or single cell lineages. The high throughput microfluidic system includes a plurality of microfluidic devices according to the present invention; a cell loading reservoir in fluid communication with the inlet end of each microfluidic channel of each microfluidic device; and an outlet reservoir in fluid communication with the outlet end of each microfluidic channel of each microfluidic device. A flow path for a fluidic medium runs from the cell loading reservoir through the microfluidic channel and into the outlet reservoir of each microfluidic device of the high throughput microfluidic system.

Figure 2:
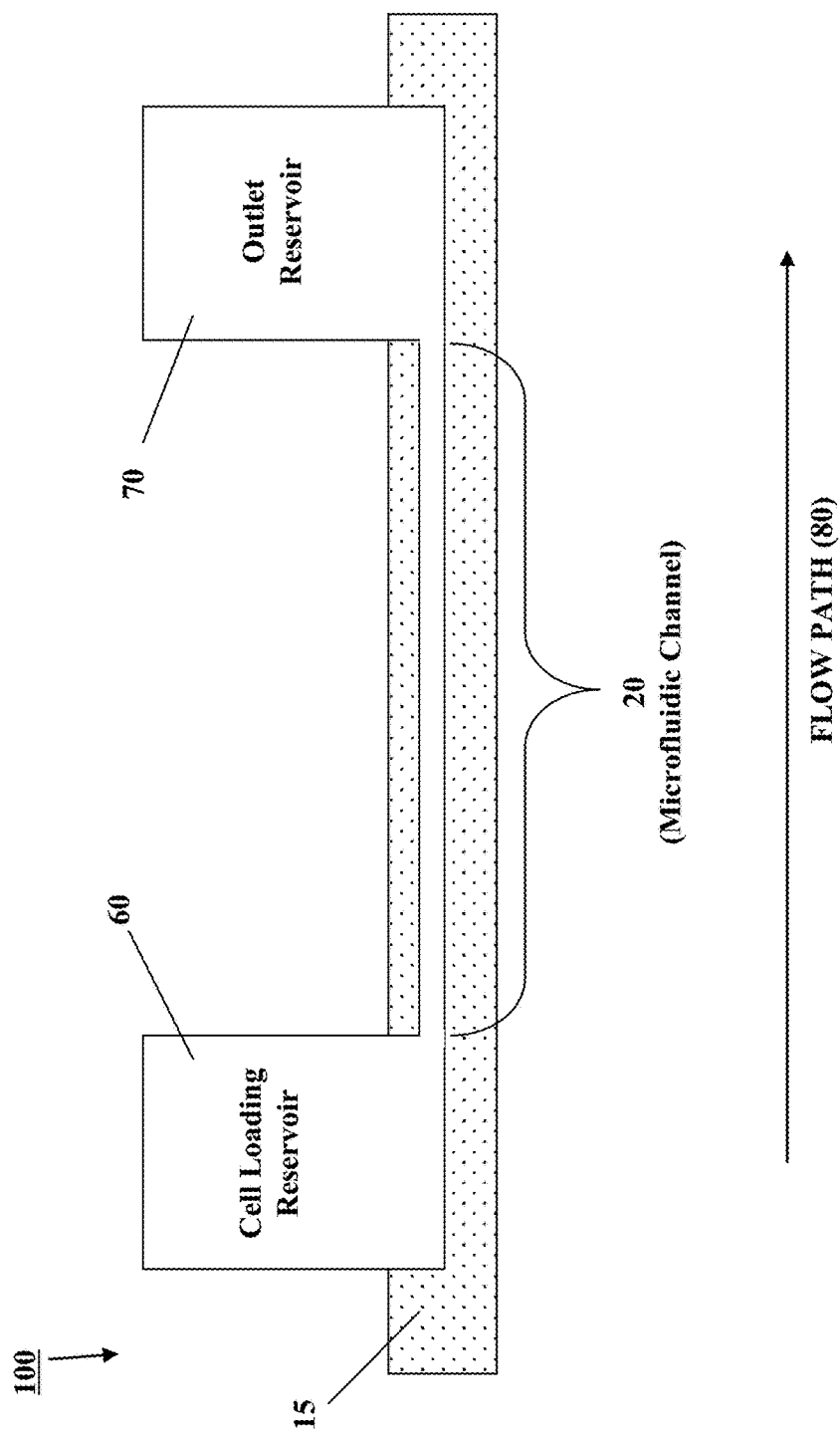
FIG. 2 is a schematic drawing of a side view of one embodiment of a microfluidic system of the present invention.

An illustrative embodiment of a microfluidic system of the present invention is shown in FIG. 2. Referring to FIG. 2, there is shown microfluidic system 100 comprising a microfluidic device of the present invention having cell loading reservoir 60 and outlet reservoir 70 integrated in fluid communication with microfluidic channel 20 formed in substrate 15. Cell loading reservoir 60 is in fluid communication with the inlet end of microfluidic channel 20, while oulet reservoir 70 is in fluid communication with the outlet end of microfluidic channel 20. Flow path 80 proceeds in the direction of the arrow whereby a fluidic medium runs from cell loading reservoir 60 through microfluidic channel 20 and into outlet reservoir 70. As shown illustratively in FIG. 2, cell loading reservoir 60 and outlet reservoir 70 are shown as chambers of the same size and shape. However, the microfluidic system of the present invention is not limited to cell loading reservoirs and outlet reservoirs that are of the same size and shape, as long as they function together according to cell loading reservoirs and outlet reservoirs as provided herein.

While the embodiments of microfluidic device 10 shown in FIGS. 1A-1D have a certain number of alternating single cell-scaled regions 32 and subcell-scaled regions 34 connected by narrowing tapered regions 40, with these regions having various lengths and shapes, the present invention is not meant to be limited to such configurations. Instead, FIGS. 1A-1D and FIG. 2 are meant to identify particular parts of the microfluidic device and/or microfluidic system of the present invention in general terms. Additional aspects of embodiments of microfluidic devices of the present invention and/or their integration into microfluidic systems of the present invention are further illustrated, without limitation, in FIGS. 3, 4A, 5B-5D, 7B, 8, 9, 10A-10B, 12A-12C, 17D, 18A-18B, 19A-19B, 21A, 21C, 22, 23, 24, 25, 26, 27, 28, 29A-29B, 30, 31, and 32.

In another aspect, the present invention relates to a kit for tracking single cells and/or single cell lineages. The kit includes a microfluidic device or a plurality of microfluidic devices according to the present invention; and at least one kit component effective for integrating the microfluidic device into a microfluidic system that comprises a cell loading reservoir in fluidic communication with the inlet end of the microfluidic channel of the microfluidic device and an outlet reservoir in fluidic communication with the outlet end of the microfluidic channel of the microfluidic device. In various embodiments, the kit component can include, without limitation, a cell loading reservoir, an outlet reservoir, instructions for integrating the cell loading reservoir and outlet reservoir into fluidic communication with the microfluidic device, a microscopy system, a video microscopy system, instructions for making and using the microfluidic system, reagents for use with the microfluidic system, etc.

Method of Tracking Single Cells and Single Cell Lineages

In another aspect, the present invention relates to a method for tracking at least one cell or cell lineage migrating through and/or incubating in a microfluidic channel having single cell-scaled and subcell-scaled regions. This method involves the following steps: (i) providing a microfluidic system according to the present invention; (ii) introducing at least one cell into a microfluidic channel of a microfluidic device of the microfluidic system; and (iii) viewing the at least one cell or cell lineage as it migrates through and/or incubates in the microfluidic channel.

In one embodiment, the introducing step comprises loading a population of cells contained in a fluidic medium into the cell loading reservoir of the microfluidic system under conditions effective to cause at least one cell or multiple cells in close proximity to one another to enter the microfluidic channel through the inlet end of the microfluidic channel and to migrate through and/or incubate in the microfluidic channel.

In one embodiment of this method, the introducing step further involves generating a flow of the fluidic medium along the flow path of the microfluidic system, where the flow path runs from the cell loading reservoir through the microfluidic channel and into the outlet reservoir.

The flow can be generated by establishing a pressure gradient or an electric field along the flow path of the microfluidic system. In one embodiment, the pressure gradient is gravity-based. In one embodiment, the gravity-based pressure gradient is established by keeping the height of the fluidic medium in the cell loading reservoir higher than the height of the fluidic medium in the outlet reservoir. In a particular embodiment, the respective reservoirs have substantially the same geometric size and shape at the point where the liquid is contained in each respective reservoir, though the respective reservoirs need not be of the same geometric size and shape. The reservoirs can include calibration marks for use in determining the respective fluidic medium height in each reservoir.

In one embodiment, generating the flow involves establishing a gravity-based fluidic pressure gradient across the flow path of the microfluidic system under conditions effective to load individual cells into individual microfluidic channels and to move those individual cells through and optionally incubate those individual cells in their respective individual microfluidic channels, at least up to one subnucleus-scaled constriction region.

In one embodiment of this method, the flow is either discontinued or maintained after the at least one cell is introduced into the microfluidic channel. In a particular embodiment, the flow is maintained for a sufficient amount of time and at a sufficient amount of pressure to induce the cells to migrate through a series of alternating single cell-scaled and subcell-scaled regions of the microfluidic channel. This enables the study of flow and pressure based effect on cell behavior. The pressure gradient can be sufficiently high, typically in the hundreds of pascals range or higher, to actively deform individual cells across sequential subcell-scaled constriction regions (e.g., subnucleus-scaled constriction regions) to measure repeated cell deformability of the same cell. Hence, the microfluidic system functions as a microfluidic serial micropipette.

In another embodiment, this method further involves inducing and maintaining fluidic equilibrium along the flow path after the flow is discontinued. This embodiment still is effective to allow cells to crawl and migrate without a pressure gradient.

In one embodiment, the at least one cell or cell lineage is caused to undergo various actions, including, without limitation, cell invasion, cell migration, cell proliferation, cell deformation, and/or drug response as they move through and/or incubate in the microfluidic channels.

In one embodiment, the viewing step comprises observing single cell or single cell lineage behavior during their migration through and/or incubation in the microfluidic channel, where the behavior can include, without limitation, cell invasion, cell migration, cell proliferation, cell deformation, and/or cell response to an introduced agent. The introduced agent can be a drug or any other chemical, biologic, etc., for testing the response of the single cell or single cell lineage thereto.

In one embodiment, multiple cells are introduced into the same microfluidic channel and caused to migrate through and/or incubate in the microfluidic channel.

In one embodiment, multiple cells are allowed to enter into the same microfluidic channel. In a particular embodiment, as one cell (referred to a Cell 1) successfully deforms across one cell-scaled constriction region (e.g., subnucleus-scaled constriction region) and then enters into the next cell-scaled region, another cell (referred to as Cell 2) that entered the same microfluidic channel after Cell 1 then comes into contact and clogs another subcell-scaled constriction region upstream of Cell 1, thereby allowing Cell 1 to undergo mechanical (e.g., stress, strain, cytoskeleton, and/or nucleus) relaxation. This allows for the study of both cell deformation and cell relaxation of two or more different cells in the same microfluidic channel, as well as the interplay between these cells and between deformation and relaxation dynamics.

In one embodiment, the at least one cell introduced into the microfluidic channel is caused to, upon coming into contact with a subcell-scaled constriction region, temporarily stop for a sufficient amount of time to induce an increase in hydrodynamic resistance in the respective microfluidic channel, thereby preventing additional cells from entering the same microfluidic channel, while allowing individual cells to become loaded in a plurality of other parallel microfluidic channels.

In one embodiment, viewing the at least one cell or cell lineage comprises using microscopy to observe the at least one cell or cell lineage in contemporaneous real-time or using video microscopy to create real-time videos or static images of the at least one cell or cell-lineage.

In one embodiment, the at least one cell or cell lineage is viewed migrating through at least one single cell-scaled region and at least one subcell-scaled constriction region.

In one embodiment, the at least one cell or cell lineage is viewed undergoing one or more deformation stage, where the deformation stage comprises an initial temporary stoppage of the at least one cell upon meeting the subcell-scaled constriction region and deformation upon entering and moving along the subcell-scaled constriction region.

In one embodiment, a plurality of cells or cell lineages are simultaneously viewed and compared from a plurality of microfluidic channels at substantially the same region of each microfluidic channel in order to observe heterogeneity between the cells or cell lineages.

In one embodiment, the at least one cell comprises a eukaryotic cell and can include, without limitation, a mammalian cell, a non-mammalian animal cell, a fungal cell, and a plant cell. In a particular embodiment, the at least one cell or cell lineage comprises any primary cancer cell or normal cell from humans, primary cells from animals, and/or cell lines.

In another embodiment, this method further involves removing unloaded cells from the cell loading reservoir to prevent additional individual cells from entering into a microfluidic channel that already contains an individual cell or individual cell lineage. In one embodiment, removing the unloaded cells can be achieved by rinsing the cell loading reservoir under conditions effective to remove all cells contained in the cell loading reservoir.

In another embodiment, this method further involves (i) extracting the cells or cell lineages from the microfluidic channels subsequent to viewing their behavior within the microfluidic channels; and (ii) optionally culturing the extracted cells or cell lineages.

In a particular embodiment of the method, the following steps are performed: Apply a pressure gradient across the device by inducing a difference in liquid height between the cell loading reservoir and the outlet reservoir. Add cells into the cell loading reservoir and allow them to be driven by the flow into the microchannels between the cell loading reservoir and outlet reservoir. Once an individual cell enters an individual channel, it will move along the flow in the larger channel region. As the cell reaches the smaller constriction region, size exclusion would prevent the cell from initially passing through the constriction. Therefore, the cell will be stopped by mechanical exclusion at the entrance into the constriction. The cell will then clog the flow in this particular channel through physical blockage and therefore induce a large hydrodynamic resistance in this channel. The deformability of the cell further increases this blockage as the cell will deform to fill in any gaps in the local cross-section of the channel. This flow stoppage effect in this channel will persist until the cell is able to fully deform into the constriction via viscoelastic creep. This will take at least several minutes at low pressure gradients (e.g. hundreds of Pascals), enabling a substantial amount of time to allow for many other parallel channels to be loaded with a single cell each.

The user can wait until many parallel channels are loaded with a single cell each in accordance with the above steps. The user can then rinse the cell loading reservoir with media to rid remaining cells in the cell loading reservoir that have not been loaded into the channels. The user can then ensure that the liquid height is always higher in the cell loading reservoir to prevent back flow such that cells are driven back out from each channel. This step is required only if the user desires to rid the remaining cell loading reservoir cells in order to prevent those cells from later invading into the single-cell channels.

Once the cells are loaded and the cell loading reservoir is rinsed, first fill the cell loading reservoir with fresh media and then later fill the outlet reservoir with fresh media to the same height to prevent any pressure gradients and flow effects. If the cell loading reservoir and outlet reservoir are joined by a larger over-arching reservoir, the user can now remove the cell loading reservoir and outlet reservoir to allow pressure to be equilibrated across the microchannels.

The user can then incubate the cells at desired conditions and allow them to automatically undergo invasion and proliferation events. Microscopy and video microscopy can be used to track these and other single-cell and single-cell lineage behavioral dynamics. Cell invasion, migration, proliferation, and responses to drugs can be assessed on a single-cell and single-cell lineage basis, since a single cell is loaded in each individual, separate channel in parallel and the subsequent progenies of each single cell will all be isolated in the same microchannel. Cell behavior, phenotypes, and decision making can also be studied.

To study mechanical cell invasion, track the probability and amount of time it takes for each cell to invade across the subnucleus barrier. To study cell proliferation of each single-cell lineage, track the number of cells in each channel over time. To study heterogeneity between single-cells and single-cell lineages, compare the properties of the cells across each separate channel. To study drug responses and drug resistance, study the behavior, growth, or death of cells in each channel. To study the emergence of drug resistance against anti-growth drugs, search for single-cell lineages that continue to grow in the presence of the drug. To study the emergence of drug resistance against any other property, search for single-cell lineages that continue expressing certain properties even under the presence of drugs that inhibit those properties. To extract resistant cells, add a cell suspending chemical (e.g. trypsin) to suspend the cells in the channels and then apply a flow across the channels until the cells are driven into the inlet or outlet for extraction (e.g. via pipetting).

Referring to FIGS. 10A-10B, there is shown one embodiment of a microfluidic device/microfluidic system of the present invention for use in a method of tracking a single cell or single cell lineage. As shown in FIG. 10A, the user can pipette a sample of interest into the inlet reservoir (also referred to herein as the cell loading reservoir) (left) and gravity drives the flow, enabling the microfluidic device/microfluidic system to operate without any external pressure actuators. Cells are automatically driven to the micropipette constrictions (also referred to herein as subcell-scaled constriction regions) (inset). As shown in FIG. 10B, after sample loading, the multi-step serial cell deformation experiments can be performed automatically with no manual input required. For example, in one embodiment, five main steps are performed in an automated manner, as follows: (i) multiple cells flow through the channels and into the constriction region, (ii) cell 1 enters the constriction and clogs the flow as it undergoes deformation under a fixed pressure gradient, (iii) cell 1 fully transits across the barrier and cell 2 subsequently clogs the flow, enabling (iv) cell 1 to relax towards equilibrium at a fixed position, (v) cell 2 fully transits across the barrier and cell 1 clogs the flow at the next constriction, allowing cell 2 to relax at a fixed position while cell 1 undergoes a secondary deformation. In the particular embodiment of FIGS. 10A-10B, the width of the larger channel region is 15 µm, the width of the smaller channel (constriction) region is 3.3 µm, and two different lengths are incorporated at the constrictions (10 µm and 60 µm), as shown in FIG. 10A inset. The height of the channels is a constant 10 µm.

Method of Tracking Drug Resistance

In another aspect, the present invention relates to a method for tracking behavior of at least one cell or cell lineage in response to exposure to an agent of interest. This method involves: (i) providing a microfluidic system according to the present invention; (ii) introducing at least one cell into a microfluidic channel of a microfluidic device of the microfluidic system; (iii) exposing the at least one cell or a cell lineage derived from the at least one cell to an agent of interest; and (iv) viewing the at least one cell or cell lineage in response to the agent as the at least one cell or cell lineage moves through or optionally incubates in the microfluidic channel. The agent of interest is introduced under conditions effective to expose the at least one cell or a cell lineage derived from the at least one cell to the agent.

In one embodiment, the agent of interest comprises a drug or drug candidate targeted against the at least one cell or cell lineage. In a particular embodiment, the drug or drug candidate is a chemotherapeutic. Any other drug or drug candidate is contemplated by the present invention.

In one embodiment, viewing the at least one cell or cell lineage comprises using microscopy to observe the at least one cell or cell lineage in contemporaneous real-time or using video microscopy to create real-time videos or static images of the at least one cell or cell-lineage.

In one embodiment, the at least one cell or cell lineage is viewed undergoing behavior changes in response to the exposure to the agent of interest, wherein the behavior changes comprise static and/or dynamic behavior changes. The behavior changes can include, without limitation, drug resistance, cell growth, cell death, cell invasion, cell migration, cell proliferation, and/or cell deformation.

In one embodiment, this method further involves identifying cells that are resistant to intended effects of the agent of interest and extracting the identified resistant cells from the microfluidic channels.

In another embodiment, the method further involves culturing the extracted resistant cells.

Figure 23:
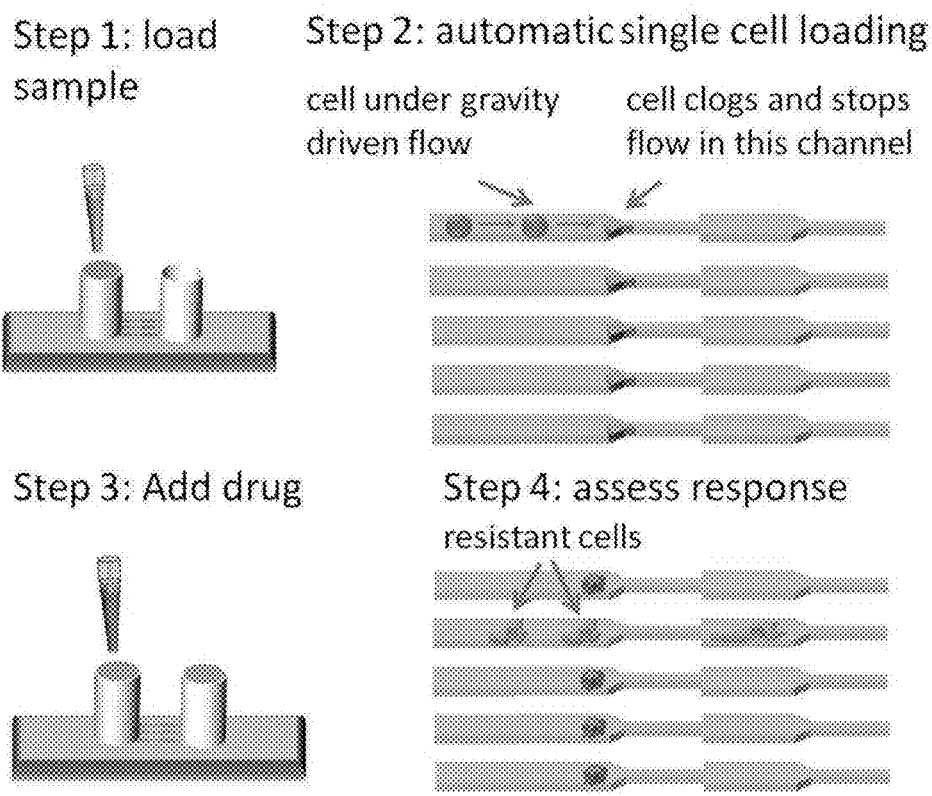
FIG. 23 illustrates operation and workflow of one embodiment of a microfluidic device/microfluidic system of the present invention. The assay developed here maximizes the simplicity of the user interface in performing difficult experiments in parallel enabled through microfluidics.

Referring to FIG. 23, there is shown one embodiment of a microfluidic device/microfluidic system of the present invention for use in a method of tracking drug resistance, including its corresponding operation and workflow. As shown in FIG. 23, the assay or method developed and illustrated in the figure maximizes the simplicity of the user interface in performing difficult experiments in parallel as enabled through microfluidics. As shown in FIG. 23, the user simply pipettes solutions into the inlet reservoirs (also referred to herein as cell loading reservoirs), and massively parallel single-cell experiments are automatically prepared. Flow from the inlet end (via the cell loading reservoir) to the outlet end (into the outlet reservoir) due, for instance, to a pressure gradient (as illustrated here), induces cells in the solution to move along the flow in the larger channel region (also referred to as the cell-scaled region). However, when the cell reaches the smaller channel (constriction) interface (also referred to as the subcell-scaled constriction region), because the constriction is smaller than the cell nucleus, which is stiff, the cell is obstructed at the interface, at least transiently before the cell and its nucleus are able to fully deform across the constriction. When the cell is at the interface, it partially deforms into the constriction and clogs the flow in that channel, thus preventing additional cells from entering that channel. This enables a single cell to be loaded into the channel. The same scheme is operated in parallel with all of the parallel microfluidic channels, thus enabling many parallel channels to be loaded with a single cell each. Each of these channels is spatially separated from each other, thus enabling each single cell and its subsequent progenies from cell division to be isolated in their own channel. This enables the tracking of single-cell and single-cell lineage properties, such as drug responsivity. For example, as shown in steps 3 and 4 of FIG. 23, a drug can be added to the channels and the response of each single-cell lineage can be independently observed. As shown in step 4 of FIG. 23, it is illustrated that the drug loaded in step 3 kills most cells (apoptotic dark green cells), but one lineage (orange cells) continues to proliferate, demonstrating heterogeneity in drug sensitivity. Additionally, this assay can be performed in a very simple manner as illustrated in steps 1-4 of FIG. 23, thus facilitating adoptability, including in biology-heavy labs and clinical settings.

EXAMPLES

The following examples are intended to illustrate particular embodiments of the present invention, but are by no means intended to limit the scope of the present invention.

Example 1

Elucidating Mechanical Transition Effects of Invading Cancer Cells with a Subnucleus-Scaled Microfluidic Serial Dimensional Modulation Device Mechanical boundaries that define and regulate biological processes, such as cell-cell junctions and dense extracellular matrix networks, exist throughout the physiological landscape. During metastasis, cancer cells are able to invade across these barriers and spread to distant tissues. While transgressing boundaries is a necessary step for distal colonies to form, little is known about interface effects on cell behavior during invasion. Here we introduce a device and metric to assess cell transition effects across mechanical barriers. Using MDA-MB-231 cells, a highly metastatic breast adenocarcinoma cell line, our results demonstrate that dimensional modulation in confined spaces with mechanical barriers smaller than the cell nucleus can induce distinct invasion phases and elongated morphological states. Further investigations on the impact of microtubule stabilization and drug resistance reveal that taxol-treated cells have reduced ability in invading across tight spaces and lose their superdiffusive migratory state and taxol-resistant cells exhibit asymmetric cell division at barrier interfaces. These results illustrate that subnucleus-scaled confinement modulation can play a distinctive role in inducing behavioral responses in invading cells and can help reveal the mechanical elements of non-proteolytic invasion.

Figure 3:
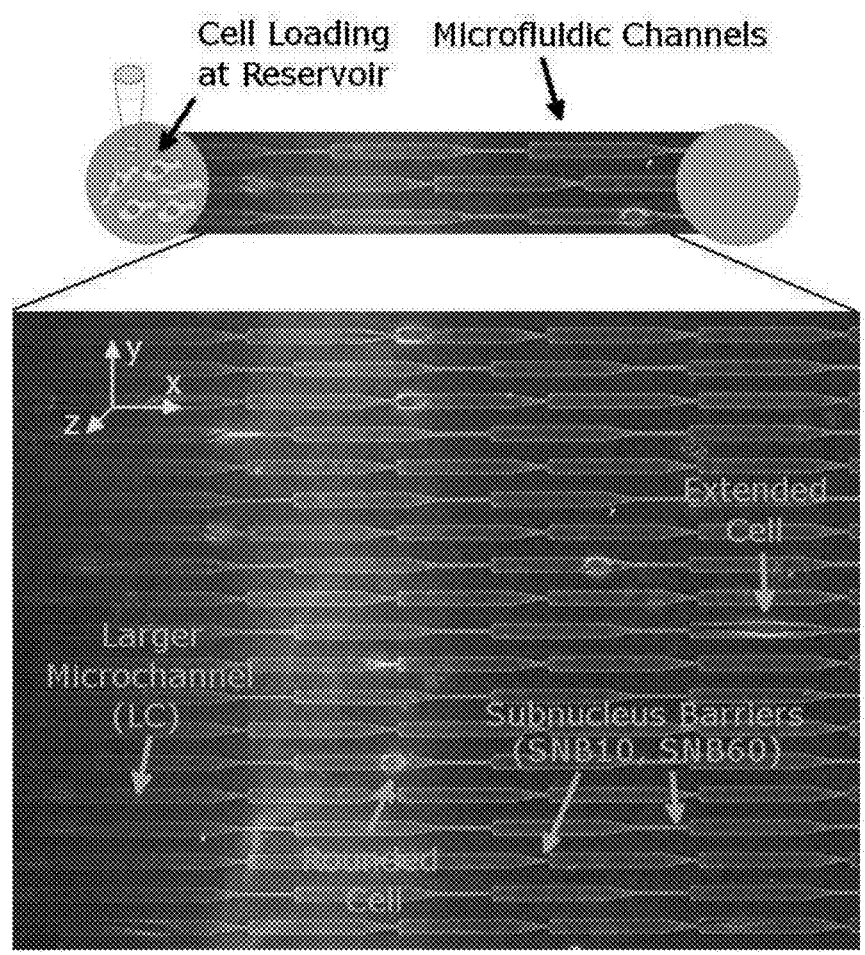
FIG. 3 illustrates one embodiment of a microfluidic device/microfluidic system of the present invention. Microfluidic channels connect two port reservoir regions. Cells are seeded into the reservoir and allowed to invade into the channels. In the actual device, the two ports are connected to the same larger reservoir in order to allow for pressure equilibration and a larger volume of media to be supplied. Expanded view: the multi-stage serial invasion channels (M.U.S.I.C.) device consists of repeating patterns of a larger channel (LC) with width (15 μm) on the scale of the cell connected to a smaller channel (the subnucleus barrier) with width (3.3 μm) smaller than the typical cell nucleus. There are two designs for the subnucleus barrier (SNB)—one is shorter than a typical cell (SNB10) and one is longer (SNB60), with lengths 10 μm and 60 μm, respectively. Transition dynamics occur when cells squeeze across the subnucleus barriers.

Here, we develop an active microfluidic system with complex, well-defined features to study the dynamics and mechanical properties of actively invading cells. As shown in FIG. 3, we incorporate patterns and repetitions along a dimensionally-confined microfluidic channel. Specifically, the dimensions are modulated and confinement features smaller than the cell nucleus are incorporated, which stimulate cell transition dynamics both in motility and morphology. Such highly confined geometries mimic the dimensionality of the smallest physiological spaces relevant in metastasis, for example small pores in the dense ECM of the tumor stroma, endothelial junctions during intravasation, and traffic-inducing microvessels (E. Sahai, *Nature Reviews Cancer*, 2007, 7, 737-749; P. Friedl et al., *Nature Reviews Cancer*, 2003, 3, 363-374; F. Sabeh et al., *Journal of Cell Biology*, 2009, 185, 11-19; Y. Kienast et al., *Nature Medicine*, 2010, 16, 116-122). Additionally, the periodic barrier design imposes multiple interfaces per cell, which is a first step in better quantifying the effects of more complex physiological boundaries that mimic the spatial heterogeneities found in the tumor stroma. The periodic barriers along a single channel also enable the sampling of individual cells multiple times. The goal of our study is to develop a device designed to test the effects of subnucleus-scaled spatial confinement modulation on the dynamics of cell invasion and the specific roles of cell mechanical plasticity and cell-to-cell heterogeneity in tumor progression. Currently there does not exist a standardized technique that can probe into the connections between these important parameters in cancer metastasis, particularly on a single high-throughput platform.

In what follows, we quantify higher order mechanical dynamics, interface induced morphological effects, and the impacts of microtubule stabilization and drug resistance during invasion. Our results reveal several key findings—1) cell transition across spaces smaller than the cell nucleus can be segmented into multiple distinct phases, 2) multiple functional strategies are employed by the cell during invasion, 3) a more extended morphological state is induced by the modulation of confined spaces, 4) microtubule stabilization impairs cell transition across mechanical barriers and alters the motile state of the cell, and 5) taxane-resistance is correlated with geometrically induced asymmetric cell division.

Methods

Cell Culture and Reagents:

MDA-MB-231 cells were obtained from the NCI PS-OC and the ATCC. They were cultured in Leibovitz L-15 media (Life Technologies) supplemented with 10% fetal bovine serum (Atlanta Biologicals) and 1% Penicillin-Streptavidin (Life Technologies). K20T cells were obtained from the Giannakakou lab at Weill Cornell Medical College. They are a taxol-resistant derivative of MDA-MB-231 cells (K. M. Wiesen et al., Cancer Letters, 2007, 257, 227-235). They were cultured in L-15 media supplemented with 10% fetal bovine serum, 1% Penicillin-Streptavidin, and 15 nM paclitaxel (taxol) (Cytoskeleton, Inc). All cells were incubated at 37° C. without supplemented $CO_2$.

Device Fabrication:

Device masters were fabricated at the Cornell Nanofabrication Facility (CNF). Standard stepper photolithography was used on SU8 resist on a silicon substrate followed by PDMS-soft lithography, similarly described in (M. Mak et al., PLoS ONE, 2011, 6, e20825). Briefly, SU8 was spun onto a Si wafer, exposed to UV with a stepper under a patterned photomask, and developed to create patterned master substrates. PDMS was then molded over the master and crosslinked to create microchannels. The channels were bonded to glass slides to create microfluidic devices.

Experiments and Analysis:

Cells were loaded into the inlet reservoir regions at the ends of the microchannels and allowed to spontaneously migrate into the three-dimensionally confined channels. Devices with cells were incubated as in regular cell culture as described above. Timelapse experiments were performed once the cells were in the channels. For each experiment, devices were placed on top of a heating plate maintained at 37° C. Typical durations for timelapse experiments were around 1-2 days at a temporal resolution of 3.4 minutes. Cell tracking and measurements were performed by manual tracing via ImageJ. Data processing and analysis were performed via custom programs on MATLAB. The height of the microchannels used for all experiments with quantitative analysis was 10 μm. 5 μm high channels were used in FIGS. 4A and 5 only for demonstrative purposes and qualitative presentation. The reason was that mechanical features were very clear for 5 μm high channels, but the experimental throughput was low because many cells did not permeate subnucleus barriers that were 5 μm high. For statistical analysis, the Chi-squared test was used for probability measurements, and ANOVA statistics were used for all other measurements, unless otherwise specified. Error bars are standard error of the mean (s.e.m.). Standard DAPI staining was used for fluorescence imaging in FIG. 9. For cell viability in these devices, we found in a typical timelapse experiment of ~23 hrs that less than 10% (5 out of 54) of the cells died while occupying the experimental field of view.

Results and Discussions

Multi-staged Serial Invasion Microchannels (MUSIC) for Investigating Cell Mechanics and Dynamics.

Figure 9:
FIG. 9 illustrates two fixed MDA-MB-231 cells with nuclei counterstained with DAPI in the MUSIC device (fluorescence with brightfield illumination), which corresponds to one embodiment of a microfluidic device/microfluidic system of the present invention. The morphology and deformation of the cell nuclei in the larger channel and during invasion across the subnucleus barrier are demonstrated. The width of the larger channel is 15 µm.

To develop an assay that can directionally focus the cell invasion program for high throughput quantitative analysis, we designed and fabricated a microfluidic device that induces serial dimensional modulation on the cell and nucleus scale (FIG. 3). We refer to this herein as a MUlti-staged Serial Invasion Channels (MUSIC) device. To perform the assay, first we induce spontaneous cell migration into confinement microchannels with cross-sectional area comparable to the cell size—the y and z dimensions are bound such that the cell is forced to move primarily along the x-direction. Then we incorporate a spatially tapering interface that connects the confinement channel to another even smaller channel (referred to as the subnucleus barrier (SNB)) with width smaller than the cell nucleus, which is one of the largest and stiffest organelles in the cell (P. Friedl et al., Current Opinion in Cell Biology, 2011, 23, 55-64). FIG. 9 shows fluorescently stained nuclei at different sections of the device, revealing nuclei morphology and deformation. This device design in essence directs and reduces the 3-D invasion program into a 2-component process—1) the cell migrates in the x-direction while 2) necessarily altering its y-dimensions. Because the migration vector points in one direction (x) and the primary induced region of change is in the orthogonal direction (y), high throughput quantitative analysis can now be accomplished in 1-D, thus increasing the feasibility of experiments and enabling predetermined axes of interest. Furthermore, repeating patterns of the subnucleus barrier are placed along the length of the microchannel, enabling serial effects and multiple sampling of individual cells, therefore providing a way to elucidate the plasticity of mechanisms of invasion for each cell. In our experiments, we consider both 1) cell invasion in only the larger confinement channel region (referred to as LCI) and 2) invasion from the larger channel across the subnucleus barrier (referred to as SNI). Our device design incorporates two different lengths for the SNB—10 μm (SNB10) and 60 μm (SNB60), which are shorter and longer than a typical MDA-MB-231 cell, respectively.

Invasion Dynamics across the Subnucleus Barrier.

Figure 4:
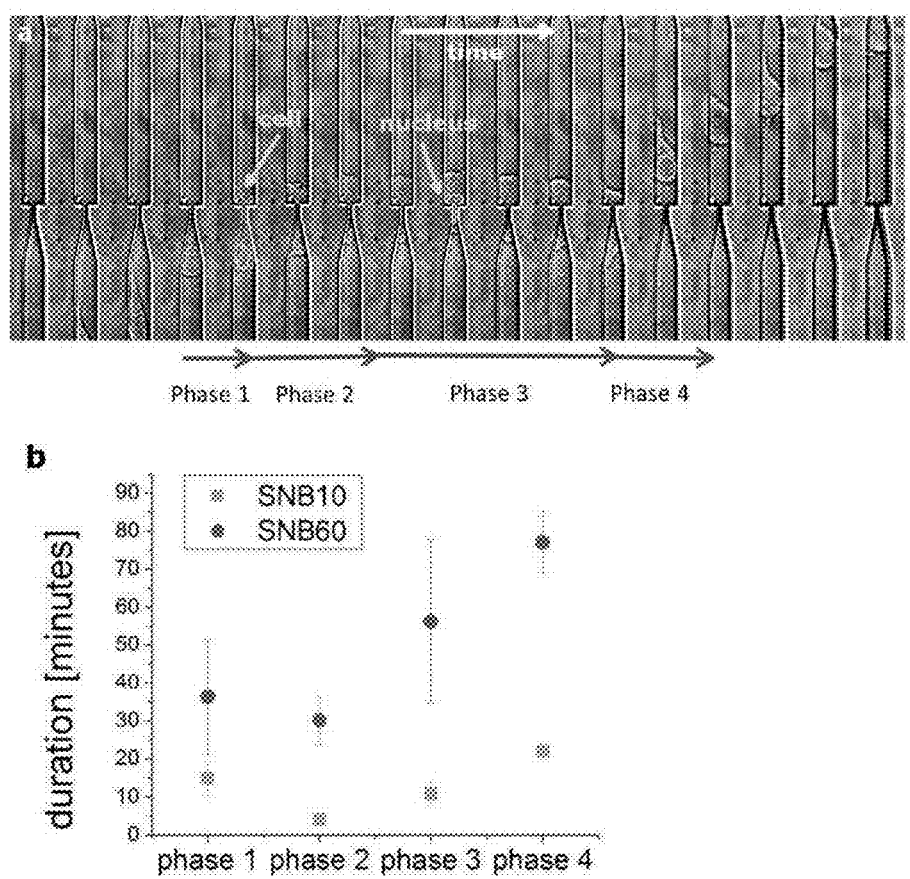
FIGS. 4A-4B illustrate cell invasion phases as observed in one embodiment of a microfluidic device/microfluidic system of the present invention.
Figure 5:
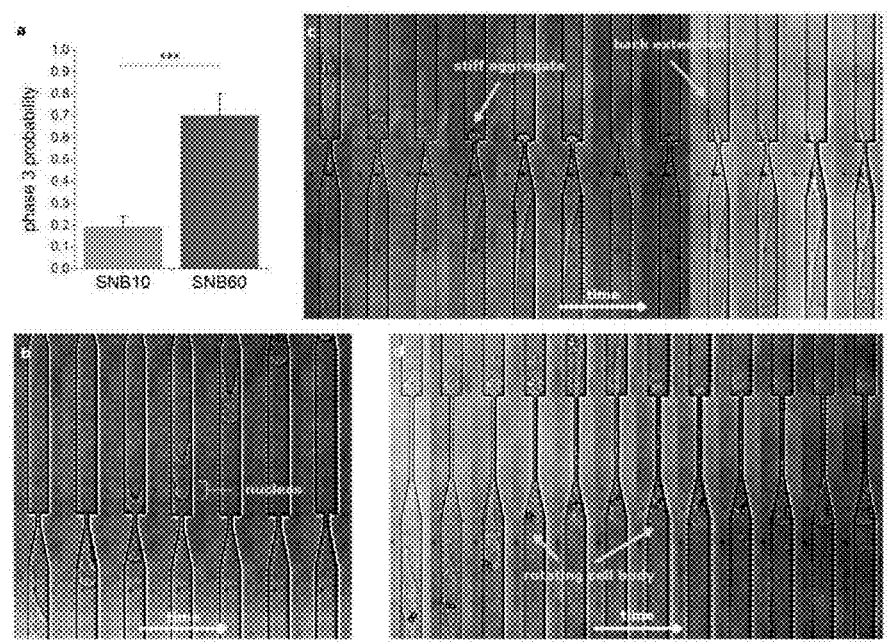
FIGS. 5A-5D illustrate functional strategies during mechanical invasion as observed in one embodiment of a microfluidic device/microfluidic system of the present invention.

To understand higher order effects of cell invasion, we first identified the nonlinearity in the cell displacement function during SNI. Then we segmented the process into 4 distinct phases and measured the time constants of each phase. This is important because SNI is a transition process, so an average velocity approximation does not reveal the transition dynamics. In our analysis, four SNI phases are distinguished by distinct mechanical characteristics as shown in FIG. 4. Phase 1—the cell migrates in the larger channel (LC) and slows down as it approaches the subnucleus barrier interface. Phase 2—the body (bulge region) of the cell starts permeating into the subnucleus barrier. Phase 3—the cell stops monotonic forward motion and either pauses or moves back and forth. Phase 4—the body of the cell exits the subnucleus barrier in a monotonic forward motion. We quantified the invasion time constants for the MDA-MB-231 cell line that models highly invasive breast cancer cells, and we parameterized the subnucleus barrier length (FIG. 4B). By dissecting the measurements into phases, we are able to describe the steps and timeframe for a cell to organize into a conformation that is conducive for subnucleus barrier invasion. Phase 3 is of particular interest in this study because it is a phase that is neglected in conventional assays that score cells based on net cell velocities or average directional persistence. It appears to be a transient reorganization phase, which we will discuss in more detail below.

Multiple Mechanical Strategies are Employed During Invasion.

The probability data in FIG. 5A shows that not all of the invasion phases are exhibited by all cells, and the barrier length can modulate the expression of these mechanical phases. Specifically, the longer subnucleus barrier SNB60 has a higher probability of inducing invasion phase 3, whereas many cells do not exhibit this phase in the shorter barrier SNB10. We take a closer look into the mechanistic steps in cell invasion across a confined area and consider the functional role of the dynamic mechanical processes that take place. Here, we qualitatively describe some of the strategies used by the cell in order to modulate its width and squeeze through the subnucleus barrier. FIGS. 5B-5D demonstrate several scenarios in which the cells squeeze across the barrier. In FIG. 5B, the cell simply contracts and the nucleus of the cell is deformed enough via the contractile force for the cell to move across the constriction. In FIGS. 5C-5D, the cell undergoes phase 3 as described previously. FIG. 5C shows a cell stuck at the barrier due to a stiff intracellular aggregate. A back extension is protruded which tensionally elongates the cell body and reduces the width of the aggregate, thus facilitating intracellular transbarrier transport. In FIG. 5D, the cell moves backwards and forward, during which there are cytoplasmic rotational dynamics. The cell body permeates into the confined region in a rolling motion, which potentially enables the sampling of different energy landscapes and deformable configurations and may reduce the energy required to deform the cell nucleus. Therefore, through dimensional modulation at the length scale of the cell nucleus, we have more clearly identified some of the mechanical and functional phenomena that are active during the invasion process. Recent studies have demonstrated that lamin b1 and dynein help regulate rotations of and force transduction onto the cell nucleus (J. R. Levy et al., *Journal of Cell Science*, 2008, 121, 3187-3195; J. Y. Ji et al., *Journal of Biological Chemistry*, 2007, 282, 20015-20026), so further investigations would be interesting to investigate their contributions to the invasion program.

Microtubule Stabilization Decreases Cell Invasiveness, but not Simply by Reducing Cell Speed.

Figure 6:
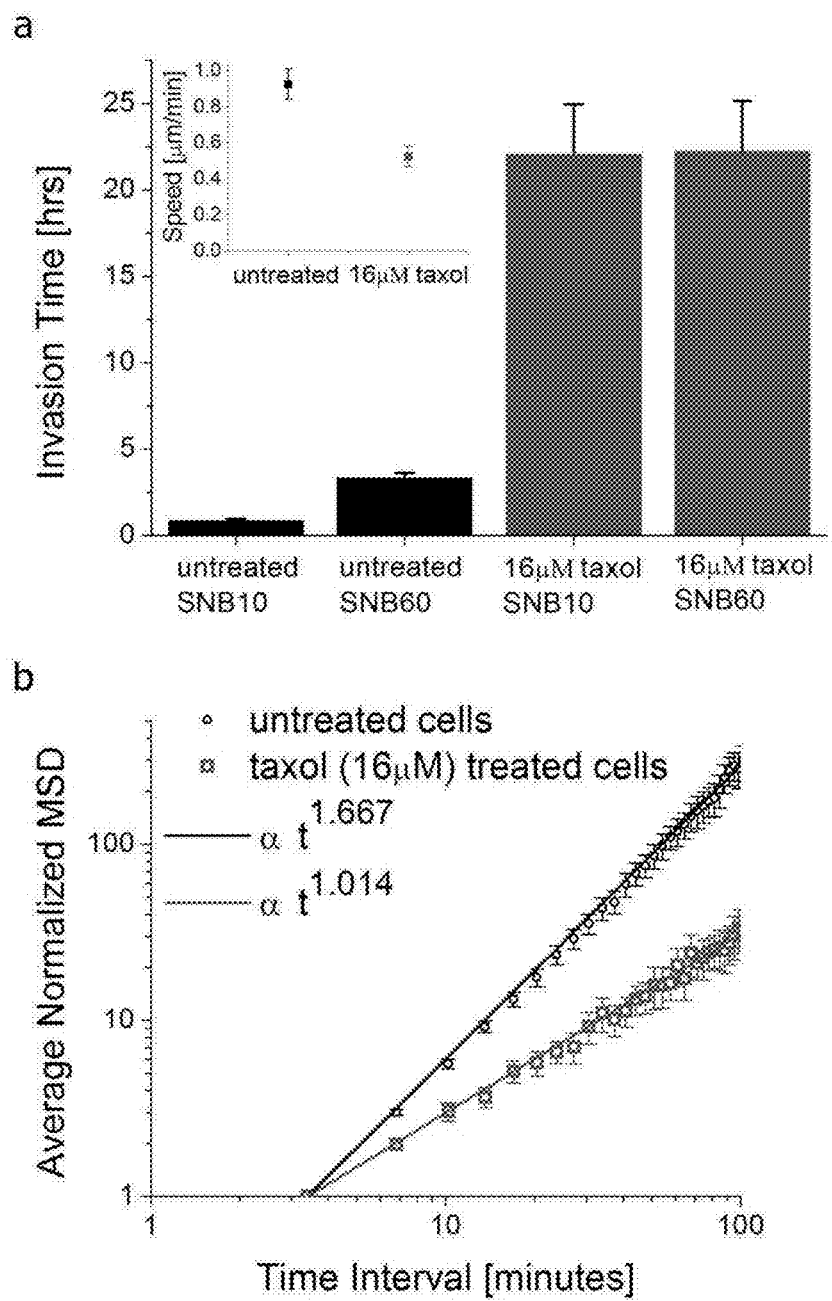
FIGS. 6A-6B illustrate the effects of microtubule stabilization as observed in one embodiment of a microfluidic device/microfluidic system of the present invention.
Figure 7:
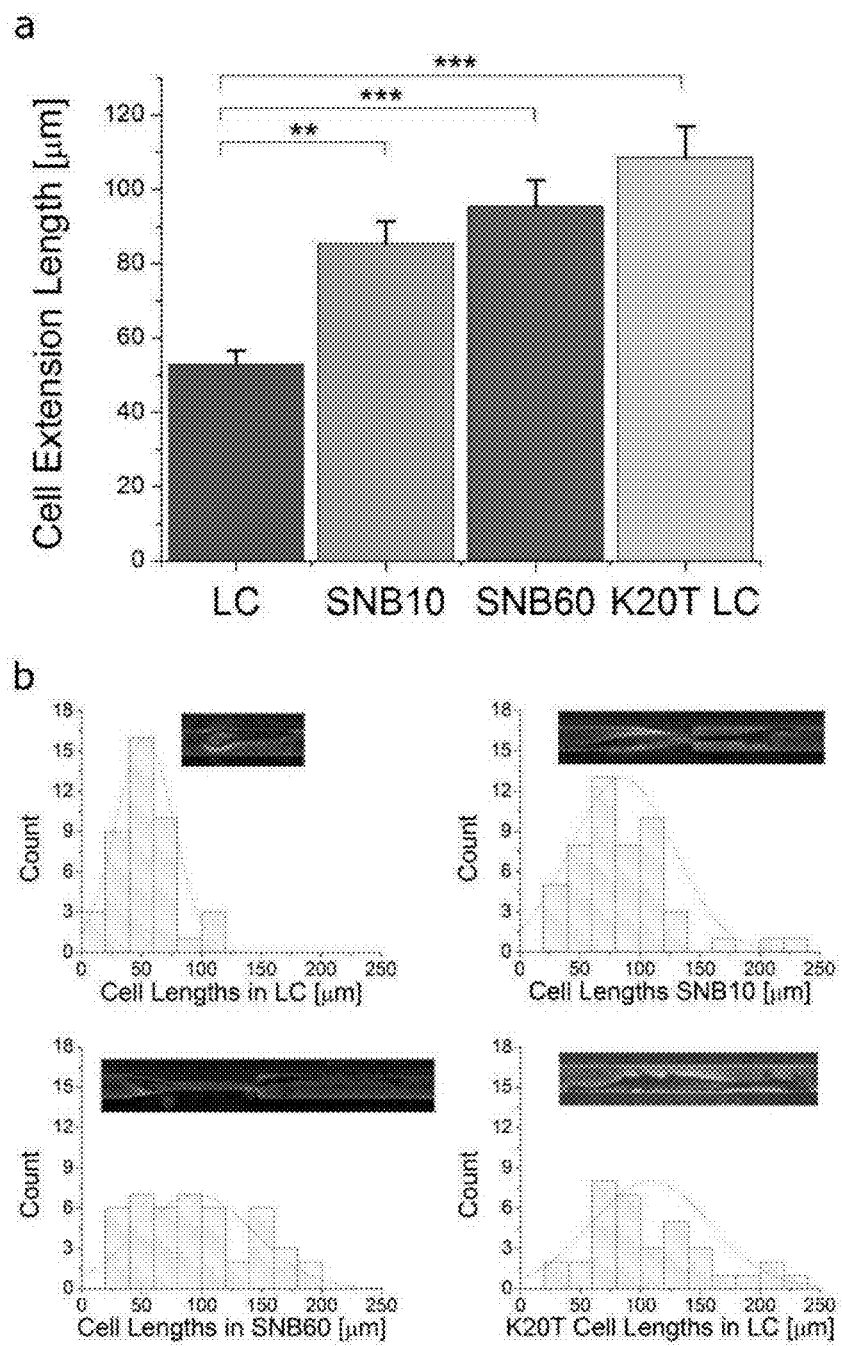
FIGS. 7A-7B illustrate cell extension lengths as observed in one embodiment of a microfluidic device/microfluidic system of the present invention.

Microtubule dynamics are important in many aspects of cell mechanics, including cell division and polarization (A. Takesono et al., *PLoS ONE*, 2010, 5, e8774; K. E. Rankin et al., *Journal of Cell Biology*, 2010, 190, 35-43; M. A. Jordan et al., *Nature Reviews Cancer*, 2004, 4, 253-265; S. Kapoor et al., *Biochemical Pharmacology*, 2012, 83, 1495-1506). Previous studies have demonstrated that microtubule stabilization reduces asymmetric distribution of cell motor proteins and reduces asymmetry in microtubule instability in the cell (S. Kapoor et al., *Biochemical Pharmacology*, 2012, 83, 1495-1506). These properties are necessary for leading and trailing edges of the cell to form, which in turn lead to polarized cell migration. Here, we consider the invasion dynamics of the cell as a result of microtubule stabilization. We compare MDA-MB-231 cells that are either untreated or treated with 16 μM taxol, which stabilizes microtubule dynamics (P. B. Schiff et al., *Proc. Natl. Acad. Sci. USA*, 1980, 77, 1561-1565). We show that taxol-treated cells spend a significantly longer time at the interface of the subnucleus barrier, as shown in FIG. 6A. For instance, for a 10 μm long subnucleus barrier, cells typically take less than 1 hour for permeation. Taxol-treated cells, however, spend t>20 hrs at the interface. Many cells actually spend more than the duration of our timelapse experiments before permeation, so the times specified for taxol-treated cells represent a lower-bound of the actual SNI time.

To explain these results from a mechanical standpoint, we consider migration dynamics of the cells in the larger channel region LC (before reaching the subnucleus barrier interface). In this region, the average cell speed differs by only a factor of ~2 between treated and untreated cells (FIG. 6A (inset)). We consider this to be low compared to the factor of >20 in total SNI time over a barrier that is only 10 μm long. To investigate the possible reasons for this phenomenon, we analyze the second moment of the cell displacement function (i.e. the mean-squared displacement (MSD)). As shown in FIG. 6B, the MSD vs. time interval relation can be fitted well to a power-law model. For untreated cells MSD $\propto t^{1.67}$, whereas for microtubule-stabilized cells MSD $\propto t^1$, where t is the time interval. To help understand the consequence of these results, consider the two limiting cases. If a particle moves at a constant velocity v, MSD=$v^2t^2$, and if a particle is undergoing 1-D Brownian motion (pure random walk), MSD=2Dt, where D is the diffusion coefficient. The power-law dependence on time will manifest on the log-log MSD vs. t curve as the slope. Our results demonstrate that untreated cells are super-diffusive, as consistent with previous 2D studies (P. Dieterich et al., *Proc. Natl. Acad. Sci. USA.*, 2008, 105, 459-463), but microtubule stabilized cells exhibit a purely random motion behavior, indicating that microtubule dynamics contribute to adding a "memory effect" to cell motility.

Since microtubules play an important role in cell polarization, motility, and division, in addition to being a well-targeted molecule in anticancer treatments (M. A. Jordan et al., *Nature Reviews Cancer*, 2004, 4, 253-265), it is particularly interesting to understand their role during mechanical invasion. Microtubule stabilization drastically reduces the ability of MDA-MB-231 cells to invade across subnucleus barriers, and one potential cause is that the cells' natural super-diffusive nature is abolished, reducing them to Brownian movers. Previous studies have shown that signaling through the Rho family of GTPases help stabilize microtubules at the leading edge of cells and can determine migration persistence, phenomenologically distinct from phosphoinositide 3-kinase (PI3K) signaling in chemotaxis (R. J. Petrie et al., *Nature Reviews: Molecular Cell Biology*, 2009, 10, 538-549; R. Pankov et al., *Journal of Cell Biology*, 2005, 170, 793-802). Concentrations of the GTPase Rac1 are modulated through the dimensionality of the microenvironment (1D lines, 2D flat surfaces, and 3D matrices), and a naturally occurring reduction in Rac1 expression in 1D and 3D as compared to 2D environments leads to fewer peripheral protrusions which results in more persistent migratory behavior (R. Pankov et al., *Journal of Cell Biology*, 2005, 170, 793-802). Rho-GTPase signaling may therefore explain the persistent migration in these confined microchannels, and by diminishing this persistence through uniform rather than localized microtubule stabilization, the cell invasion ability across subnucleus barriers is also impaired. This suggests that microtubule stabilization may prevent cells from permeating across tight spaces, which when used together with matrix metalloproteinases (MMP)-inhibitors to prevent proteolytic invasion, may produce a synergistic effect in suppressing invasion across tight physiological spaces (some of which are degradable by MMPs). A previous study used protease inhibitors together with Y27632 (which inhibits Rho-associated protein kinase ROCK) and demonstrated synergistic effects in preventing cell invasion (E. Sahai et al., *Nature Cell Biology*, 2003, 5, 711-719). One difference here is that microtubule targeting drugs are approved and readily available in cancer treatments. These drugs have been applied traditionally for their anti-mitosis and apoptosis effects in addition to potential anti-metastasis properties (M. A. Jordan et al., *Nature Reviews Cancer*, 2004, 4, 253-265; M. E. Stearns et al., *Cancer Cell*, 2007, 11, 526-538). However, it is unclear how they affect single-cell invasion. Our results suggest that for viable cells after treatment, anti-invasion effects from taxol may manifest in the impediment of polarization-dependent permeation across subnucleus barriers (rather than on simply altering cell speed). These details can potentially help in the design of new combination chemotherapeutics.

Dimensional Modulation Induces Differential Cell Extension Lengths.

With the MUSIC device, we demonstrate that dimensional modulation on the scale of the cell and cell nucleus and interface effects from subnucleus barriers can induce morphological changes in invading cells. As demonstrated in FIG. 7, when a cell interacts with a region smaller than the cell nucleus, significantly longer extensions are protruded. These extensions can be hundreds of micrometers long. Interestingly, K20T cells, the taxol resistant derivative of MDA-MB-231 cells, are longer even without interface effects. Furthermore, the cell length distribution data shown in FIG. 7B demonstrates the diversity of morphological states exhibited during the invasion process.

These results suggest that mechanical barriers can cause cells to have a larger, more extended region of influence, which may facilitate nutrient-finding and homing towards the vasculature in conjunction with other mechanisms such as chemotaxis (J. D. Sheilds et al., *Cancer Cell*, 2007, 11, 526-538). Certain cell morphologies have been linked to more potent cancer phenotypes. Compressive forces in 2D experiments for instance lead to a "leader cell" phenotype that is elongated and spindle-shaped and leads neighboring cells in the invasion process (J. M. Tse et al., *PNAS*, 2012, 109, 911-916). Substrate stiffness and tensional forces can induce larger cell areas and activate integrin mediated signaling pathways that lead to more malignant phenotypes (M. J. Paszek et al., *Cancer Cell*, 2005, 8, 241-254). The sidewalls of the subnucleus barriers in the MUSIC device essentially impose compression in the form of normal forces onto the cell and its nucleus during invasion, and the induced cell elongation process likely causes higher tension along the cell. Subnucleus barrier confinements therefore may contribute towards driving metastatic phenotypes.

Taxol Resistant Cells are More Susceptible to Asymmetric Cell Division During Invasion.

Figure 8:
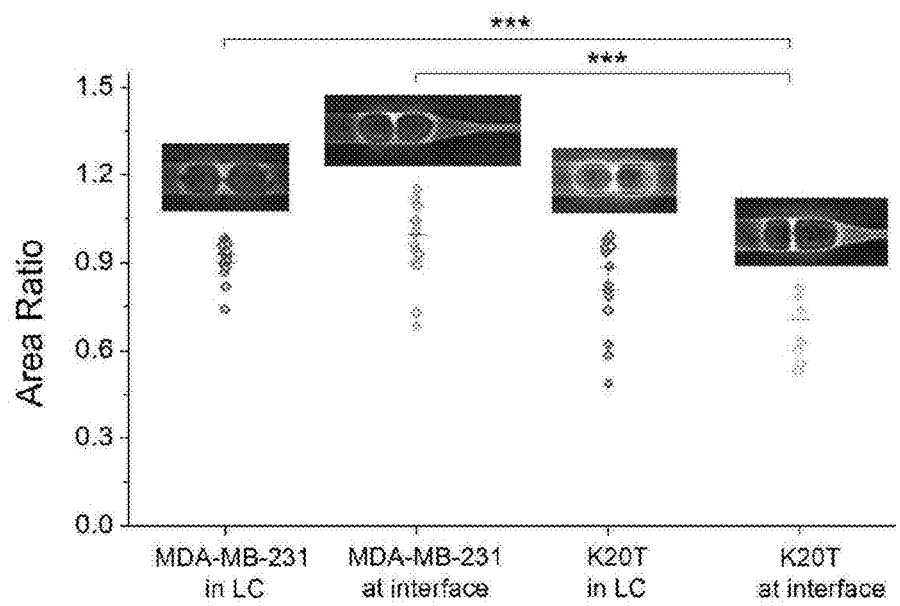
FIG. 8 illustrates cell division asymmetry as observed in one embodiment of a microfluidic device/microfluidic system of the present invention. MDA-MB-231 cells tend to divide symmetrically both in the larger channel LC and at the barrier interface. K20T cells, however, tend to divide asymmetrically at the subnucleus barrier interface. The daughter cell closer to the barrier is larger. AR=area ratio between daughter cells. In the symmetric larger channel LC, AR=smaller cell/larger cell. At the interface, AR=left cell/right cell, and only cells dividing while invading from left to right into the SNB are taken into account. The area ratios measured are (mean=0.91, median=0.92, n=19) for MDA-MB-231 in LC, (mean=0.97, median=0.96, n=17) for MDA-MB-231 at SNB interface, (mean=0.85, median=0.94, n=17) for K20T in LC, and (mean=0.67, median=0.63, n=7) for K20T at SNB interface. *** indicates p<0.001 from ANOVA statistics. Error bars are s.e.m. The width of the larger channel is 15 µm.

K20T cells are taxol-resistant MDA-MB-231 cells selected as described in K. M. Wiesen et al., Cancer Letters, 2007, 257, 227-235. As shown in FIG. 8, K20T cells that divide while moving from left to right into the subnucleus barrier interface exhibit geometric asymmetry in its axis of division, with the daughter cell closer to the confinement region being 50% larger. This phenomenon is not as pronounced in control MDA-MB-231 cells or in K20T cells that divide in the symmetric straight region of the device. Calculations of area ratios are determined by the following methodology: in symmetric large channel regions, the area ratio $AR=A_{smaller\ cell}/A_{larger\ cell}$; in the interface region, only cells moving from left to right into the interface are considered, and the area ratio is determined by $AR=A_{left\ cell}/A_{right\ cell}$. Asymmetric cell division has been linked to aneuploidy and genomic instability, which can potentially lead to accelerated and gain of function mutations (Z. Storchova et al., *Nature Reviews Molecular Cell Biology*, 2004, 5, 45-54; J. A. Knoblich, *Nature Reviews Molecular Cell Biology*, 2010, 11, 849-860; H. Rajagopalan et al., *Nature*, 2004, 432, 338-341). Our results here could imply that the resistant cell line is intrinsically more ready to mutate and that geometric effects during invasion can have an impact on cell division, mutations, and directed evolution. Further investigations into cell ploidy and phenotypic differences between cells that have divided asymmetrically will be necessary to investigate the connections between drug and taxane-resistance and tumor cell evolution during invasion. Previous efforts in 2D protein micropatterning techniques have demonstrated that the axis of cell division and mitotic spindle positioning can be regulated by geometric constraints (J. Fink et al., *Nature Cell Biology*, 2011, 13, 771-778; M. Thery et al., *Nature*, 2007, 447, 493-497). However, connections between cell behavior (migration and division) in 2D geometric patterns and cancer progression and evolution due to invasion, inherently a 3D process, are unclear. Confinement in 3D mechanically simulates tight physiological spaces relevant during invasion, and physiological cell division also usually occurs in 3D, so a transition from 2D engineered patterns to 3D engineered patterns can reveal insights of dimensionality on cell division mechanics. Additionally, the probability of a cell dividing at any given region of fixed length should be higher if there is a mechanical barrier there because the cell spends more time in that region due to the transition dynamics described earlier. Therefore, understanding cell division effects caused by different mechanical barriers during invasion may provide insights towards potential driving elements of cell evolution. This is particularly interesting for cancer cells since they are notorious for their ability to acquire new abilities[4] and they typically do not exhibit contact inhibition (S. Suresh, *Acta Materialia*, 2007, 55, 3989-4014; L. Liu et al., *Proc. Natl. Acad. Sci. USA*, 2011, 108, 6853-6856), so their cell cycle is likely not influenced by external elements such as mechanical confinement. We note here that the throughput of these experiments in this design of the MUSIC device is lower in comparison to the invasion studies since only a fraction of the invading cells will divide at the SNB interface. A next generation device design incorporating more frequent SNBs can increase experimental throughput by increasing the probability that a cell is positioned in a geometrically asymmetric location during division.

CONCLUSION

There are many instances when cells exhibit modulation from their environment. Sometimes the external stimulation exists as chemical cues as in chemotaxis, and sometimes it is presented as mechanical cues, such as during contact inhibition or durotaxis (J. D. Sheilds et al., *Cancer Cell*, 2007, 11, 526-538; L. Liu et al., *Proc. Natl. Acad. Sci. USA*, 2011, 108, 6853-6856; B. C. Isenberg et al., *Biophysical Journal*, 2009, 97, 1313-1322; E. T. Roussos et al., *Nature Reviews Cancer*, 2011, 11, 573-587). Often times the signal is both physical and chemical, as in cell-cell or cell-ECM interactions (M. J. Paszek et al., *Cancer Cell*, 2005, 8, 241-254; E. T. Roussos et al., *Nature Reviews Cancer*, 2011, 11, 573-587; M. H. Zaman et al., *Proc. Natl. Acad. Sci. USA.*, 2006, 103, 10889-10894; Y. Zheng et al., *Proc. Natl. Acad. Sci. USA*, 2012). Here we presented a different form of mechanical modulation—modulation in the confinement dimensions of invading cells. This is of particular interest towards cancer progression and metastasis because tumor growth can lead to increased confinement sensed by the cells and cell invasion can involve permeation across tight spaces, from tumor stroma to basement membranes to endothelial junctions (A. F. Chambers et al., *Nature reviews*, 2002, 2, 563-572; E. Sahai, *Nature Reviews Cancer*, 2007, 7, 737-749; J. M. Tse et al., *PNAS*, 2012, 109, 911-916). We have created a platform—serial dimensional modulation at the subnucleus length scale—and device (MUSIC) that enable new phenomenological events associated with mechanical cell invasion and boundary effects to be elucidated and quantified. We focused on higher order invasion dynamics, morphologies, division, and pharmacologic effects and thus have demonstrated the details and wide range of biological phenomena on the single-cell scale that can be interrogated with our approach. Our analysis revealed some important characteristics, such as elongated morphologies, cell division asymmetry, and super-diffusivity, that suggest potential mechanical elements during invasion that can drive cancer metastasis and progression. Our previous work (M. Mak et al., *PLoS ONE*, 2011, 6, e20825) has also shown that more subtle geometric effects such as barrier angles could impact invasion behavior and that cancer cells of different metastatic grades exhibit differential invasion capacities across mechanical barriers. Further studies using the MUSIC device for different cancer cell lines with different external chemotactic inputs can help elicit and establish characteristic behavioral signatures of mechanical invasion and identify modulation effects from chemokines Therefore, our platform has potential applications in uncovering subtle properties of cell invasion, drug screening, and discovering mechanical biomarkers. The portable and versatile lab-on-a-chip form-factor of and the label free properties measurable by our technique also facilitate implementation in clinical and commercial settings.

Example 2

A Simple Automated Serial Micropipette and the Implications of Cancer Cell Repeated Deformations Cells are complex viscoelastic materials that are frequently in deformed morphological states, particularly during the cancer invasion process. The ability to study cell mechanical deformability in an accessible way can be enabling in many areas of research where biomechanics is important, from cancer metastasis to immune response to stem cell differentiation. Furthermore, phenomena in biology are frequently exhibited in high multiplicity. For instance, during metastasis, cells undergoing non-proteolytic invasion squeeze through a multitude of physiological barriers, including many small pores in the dense extracellular matrix (ECM) of the tumor stroma. Therefore, it is important to perform multiple measurements of the same property even for the same cell in order to fully appreciate its dynamics and variability, especially in the high recurrence regime. We have created a simple and minimalistic micropipette system with automated operational procedures that can sample the deformation and relaxation dynamics of single-cells serially and in a parallel manner. We demonstrated its ability to elucidate the impact of an initial cell deformation event on subsequent deformations for untreated and Paclitaxel treated MDA-MB-231 metastatic breast cancer cells, and we examined contributions from the cell nucleus during whole-cell micropipette experiments. Finally we developed an empirical model that characterizes the serial factor, which describes the reduction in cost for cell deformations across sequential constrictions. We performed experiments using spatial, temporal, and force scales that match physiological and biomechanical processes, thus potentially enabling a qualitatively more pertinent representation of the functional attributes of cell deformability.

Therefore there is a need for multifunctional, procedurally adept, and automated systems that require minimal labor and components in order to promote accessibility and technology adoption.

To address this need, to eliminate the tradeoff, and to simplify labor for complex experimental procedures—we considered several factors. In order to fully appreciate the biomechanical properties of cells but in a high throughput and automated manner, it is necessary to develop a scalable microfluidic design that incorporates scale matching in important experimental parameters, such as spatial, temporal, and force properties. Not only is it important for feature sizes of the device to be on the order of the cell and nucleus size, but the time scale of measurements should match biomechanical time scales as in strain and relaxation events. It may also be important for externally applied forces onto cells to be comparable in magnitude to those present in biological systems in order to appreciate physiological responses, as in migration and invasion driven by cell generated forces. For instance, if the flow rate used in microfluidic techniques is too high, which is typically the case in previous studies aimed at high throughput operations, relaxation dynamics cannot be studied and appreciated since they are slower. If the flow rate is too low, experiments would be impractical as cells would not deform sufficiently. By performing time-scale matching, we can appreciate the properties conferred upon the cell by the coupling of relaxation and deformation dynamics. This is particularly interesting in the context of cancer metastasis, in which cells undergo frequent squeezing and recovery events during and after invasion across highly confined physiological spaces (e.g. constricted gaps in the ECM, endothelial junctions, microvessels). Furthermore, while typical experiments especially in microfluidics can sample many cells, individual cells are usually sampled only once. Because each cell is a highly complex system, a single sample per cell may not provide details about the diversity of and dynamics associated with the responses of a single cell. Thus, such data, while high throughput, are limited by their inability to distinguish the variability between different cells in a population and the variability of a property within an individual cell.

The device we present here is a parallel array of serial micropipettes capable of performing both deformation and relaxation measurements of individual cancer cells. Each cell is sampled multiple times for the assessment of consequential effects, which enables us to answer questions such as 1) how does one deformation event impact subsequent deformation events and 2) what are the key dynamics that govern serial deformations? Addressing these questions is important because it offers a more comprehensive assessment of a complex cell mechanical property (deformability) over a one-shot measurement (e.g. the aspect ratio of a cell under a fixed stress). This is also important for physiological relevance because, for instance, during the metastatic cascade, cells typically undergo a multitude of deformation events, from active invasion across confined spaces of the ECM in the tumor stroma to circulation across small blood and lymphatic vessels. Cancer cells therefore undergo constant deformations. Because cells are viscoelastic, their deformability is impacted by their conformational states conferred from their previous deformation events. However, the dynamics of serial deformations are unclear, and our device enables these dynamics to be elucidated. By understanding if and how a cell is conditioned by deformations in subsequent events, we can begin to gain potential insights toward the mechanical elements that govern cancer metastasis.

For our experiments, we used the MDA-MB-231 cell line, which model highly metastatic breast adenocarcinoma. Their metastatic nature and previous studies (J. Guck et al., *Biophysical Journal*, 2005, 88, 3689-3698; M. Mak et al., *Plos One*, 2011, 6; L. Liu et al., *Proceedings of the National Academy of Sciences*, 2013, 110, 1686-1691) indicate that their deformation dynamics are of particular interest. Our results demonstrate several key findings. An initial deformation event facilitates subsequent serial deformations of the same cell, and this mechanical conditioning is dependent on the initial and remaining strain on the cell. The strain dynamics during deformation are dependent on both the viscoelastic cell body and nucleus. These experiments were performed in a simple microfluidic design with an automated experimentation scheme, which increases the capacity of practicable experiments and provides an instantly enabling technology to any basic biology lab setting in a small self-reliant form factor requiring no external equipment or micromanagement.

Experimental Section

Cell Culture

MDA-MB-231 cells were obtained from the NCl Physical-Sciences and Oncology Center. They were cultured in Leibovitz L-15 media (Life Technologies) with 10% fetal bovine serum (Atlanta Biologicals) and 1% Penicillin-Streptavidin (Life Technologies) at 37° C. without $CO_2$.

Device Fabrication

Device masters were fabricated at the Cornell NanoScale Facility (CNF). Standard photo- and soft-lithography techniques were used to create devices. Briefly, SU8 was spun onto a silicon wafer and exposed under a photomask with the micropipette patterns in a stepper. The patterned wafer was then developed to create a negative image of the device. PDMS was cast onto the master and crosslinked to create the micropipette channels. The channels were then bonded to glass slides to create the finished microfluidic device.

Experiments and Analysis

Devices were treated with 1% bovine serum albumin (BSA) (Sigma-Aldrich) in serum-free media (L-15) for several hours before experiments in order to prevent stiction. Additionally, cells used in experiments were resuspended in serum-free media. Cells were loaded into the inlet reservoir of the device and experiments were automatically conducted as described in the design and operations section of this paper. The device was placed and kept on a heating plate set at 37° C. Videos were recorded at 500 ms per frame under a microscope, which produced the data of the experiments. Experimental analysis and cell tracking were performed using ImageJ and custom MATLAB programs. For statistical analysis, one-way ANOVA was used to determine statistical significance. Error bars on data represent standard error of the mean (s.e.m.). For taxol experiments, cells were incubated in 10 μM taxol (Cytoskeleton, Inc.) for 1 day prior to experiments. For fluorescence experiments, NucBlue (a live nucleus counterstain that is formulated from Hoechst 33342) (Life Technologies) was used and cells were incubated in the dye in complete growth media for 15 minutes.

Results and Discussion

Device Design and Operations

Figure 10:
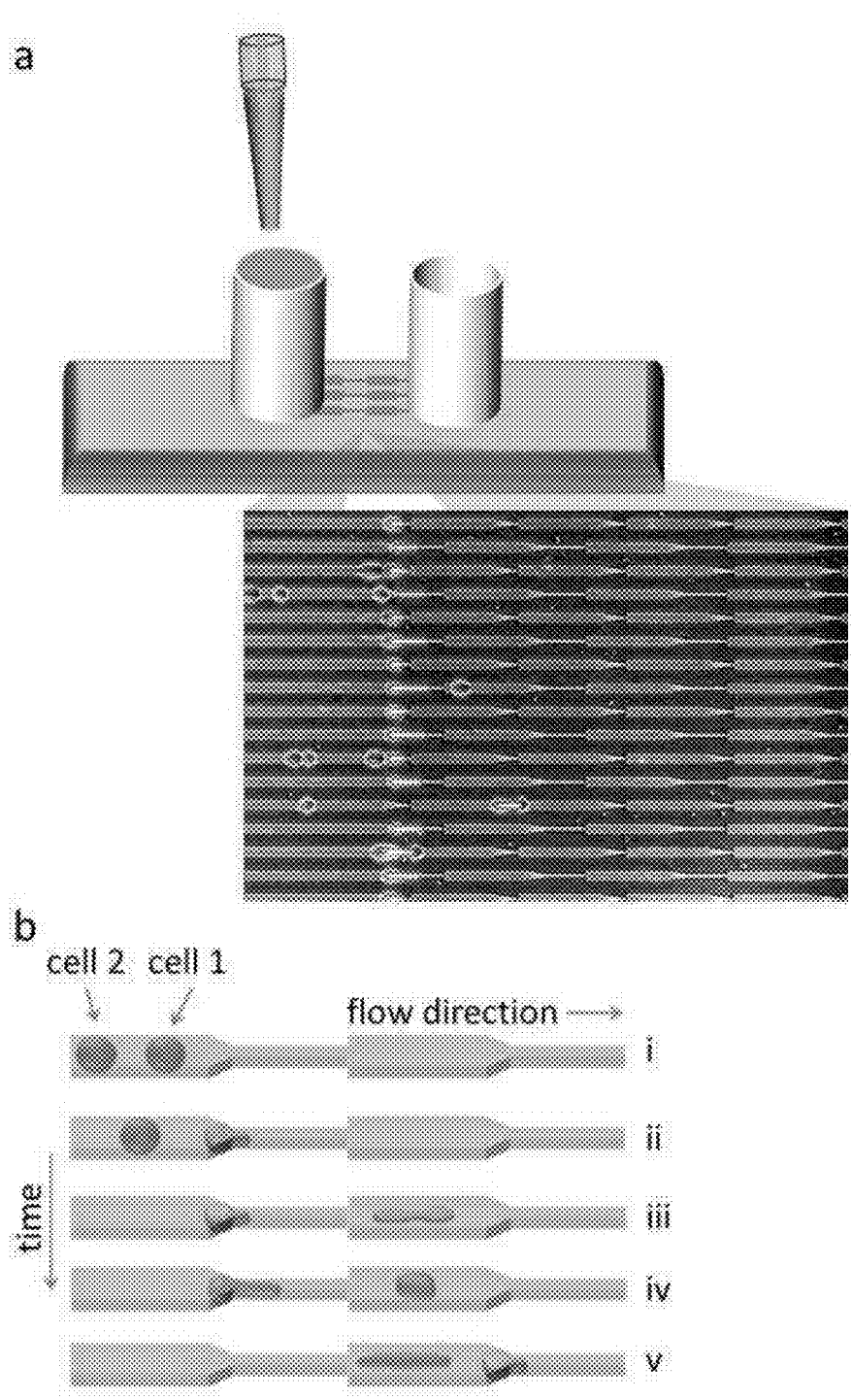
FIGS. 10A-10B are schematic illustrations of one embodiment of a microfluidic device/microfluidic system of the present invention and operations thereof.

The device consists of parallel microchannels. Each channel contains a series of microconstrictions to serve as a serial micropipette capable of deforming objects multiple times via pressure driven flow. The larger region of the channel has a width of 15 μm, which is on the order of the size of a cell. The smaller constriction region is 3.3 μm, which is smaller than the cell nucleus, thus ensuring that the cell undergoes a substantial deformation that samples a key organelle in the cell that often limits cell squeezing in physiological landscapes due to its size and stiffness. Additionally, two different lengths of the constriction region are incorporated, one that is 10 μm-long (shorter than a typical cell) and one that is 60 μm-long (longer than a typical cell), mimicking short physiological barriers such as ECM-pores and long physiological barriers such as microvessels, respectively (FIG. 10A inset). A pressure gradient is induced on-chip across each channel by applying a difference in liquid height between the inlet and the outlet of the device. This enables device operation without external pressure sources. For the experiments here, we applied a pressure gradient of around 400 pa, which is comparable to interstitial pressures in tumors (Y. Boucher et al., *Cancer Research*, 1990, 50, 4478-4484). Our device design and operations facilitate more conventional micropipette studies than existing microfluidic constriction or deformation schemes, enabling multifaceted studies in an automated manner as shown in FIG. 10 and described in the following:

Strain Rate at Fixed Pressure:

Cells that enter the constriction region essentially clog the flow (inducing infinite hydrodynamic resistance) so the pressure drop (400 pa) across the channel is entirely across the cell. In considering the cross-sectional area of the channel and thus the area of the cell that the pressure is acting on, this translates into an applied force across the cell of around 60 nN, which is on the scale of the forces that an individual cell generates (M. Prass et al., *The Journal of Cell Biology*, 2006, 174, 767-772; C. M. Kraning-Rush et al., Plos One, 2012, 7, e32572; C. A. Lemmon et al., *Biophysical Journal*, 2009, 96, 729-738). Timelapse microscopy enables the tracking of the cell strain over time under this fixed pressure.

Release and Relaxation after an Initial Strain:

After an initial strain is applied to the cell during constriction transit, cell relaxation dynamics can be assessed. This is accomplished in an automated manner in this device as subsequent cells will plug the constrictions as they undergo transits, stopping the flow, and enabling the previously deformed cell to relax at a fixed position for tracking.

Tracking Serial Cell Deformations:

Every micropipette channel is designed with multiple constrictions in series to enable the multiple sampling of each transiting cell. This is important because each cell is dynamic and heterogeneous, and a static measurement of a cell property does not provide insights into its full capacity. The serial design induces cells to necessarily transit across multiple barriers to probe dynamic effects. However, even at relatively low pressures, subsequent transit times can be fast due to a mismatch in the relaxation rates and flow speeds (the cell is still in a highly deformed state in subsequent transits), thus masking the dynamic regime in the behavior of serial deformations. With our device, because each serial micropipette consists of a single channel, intermittent flow pauses are automatically generated as multiple cells are transiting across the same micropipette channel, as shown in FIG. 10, thus enabling cells to relax back towards its initial conformation before the next deformation event. This enables us to probe into the dynamics that govern multiple cell deformations and cell mechanical properties that result from the coupling between relaxation and deformation.

Repeated Cell Transits and Taxol Treatment

Figure 11:
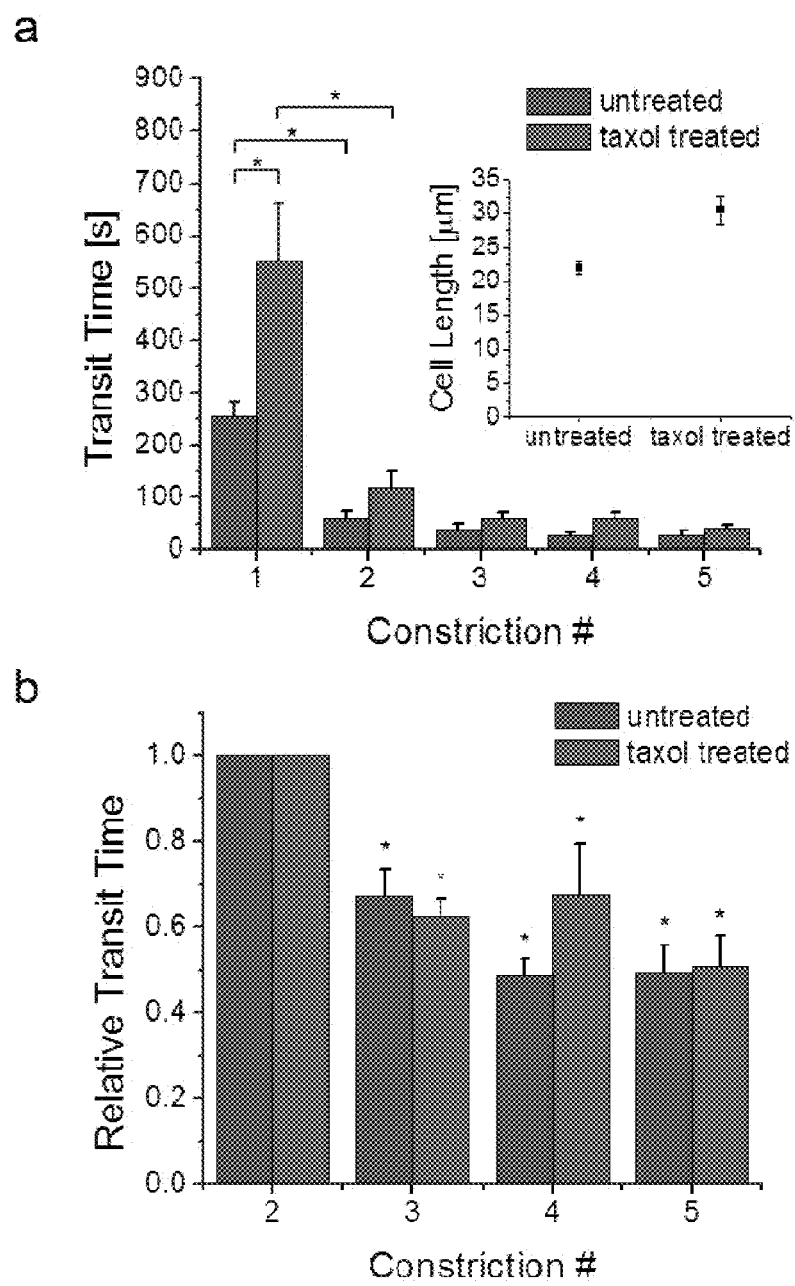
FIGS. 11A-11B illustrate cell permeation across sequential micropipette constrictions and the effects of taxol treatment, as observed in one embodiment of a microfluidic device/microfluidic system of the present invention.
Figure 12:
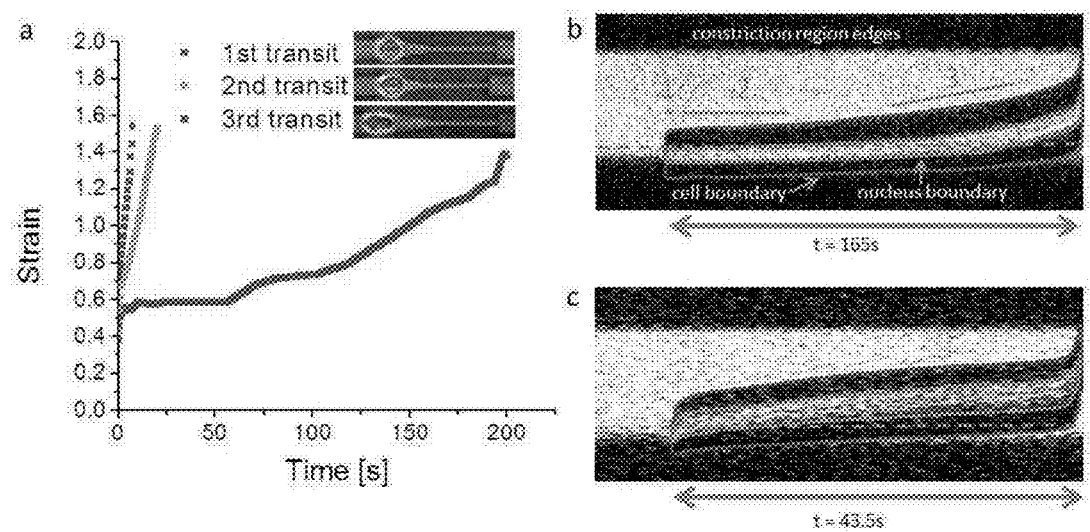
FIGS. 12A-12C illustrate serial deformation dynamics, as observed in one embodiment of a microfluidic device/microfluidic system of the present invention.

Using the procedure demonstrated previously, we measured the transit times of the same cell across 5 sequential constrictions. Here, we considered situations in which only one cell was present in the serial micropipette channel, so cell 2 from FIG. 10 was not present, and we examined experiments from the 10 µm-long constriction design. Because cell 2 was not present, cell relaxation between constrictions is typically less than 1 second. We investigated the serial deformations of both untreated cells and cells treated with 10 µM Paclitaxel (taxol), a chemotherapeutic drug that stabilizes microtubules and inhibits cell division (P. B. Schiff et al., *Proc. Natl. Acad. Sci. USA*, 1980, 77, 1561-1565; M. A. Jordan et al., *Nature Reviews Cancer*, 2004, 4, 253-265; K. E. Gascoigne et al., *Journal of Cell Sciences*, 2009, 122, 2579-2585), for 1 day. As shown in FIG. 11A, the transit times across constrictions decrease after the first transit. The transit time across the first constriction is larger for taxol treated cells, which we may expect as the size of these cells is significantly larger than untreated cells (FIG. 11A inset) due to mitotic inhibition. Here, the size is defined by the length of the cells in the microchannel, since the cell width generally fills the channel width. As the cells transit across subsequent barriers, however, the transit times collapse between the two cell groups, demonstrating that once the cells are under sufficient deformation, cell size becomes less important in determining transit times. Interestingly, we also found that cell permeation across constrictions is further facilitated after the second transit, as illustrated in FIG. 11B. For each cell, we normalized the transit times across the third, fourth, and fifth constrictions to the transit time across the second constriction of the same cell, and our results show that cells can transit across the later constrictions more quickly.

These findings suggest that cells that undergo perpetual deformations exhibit less difficulty in permeating across highly confining subnucleus-scaled mechanical barriers. Since aggressive cancer cells are constantly undergoing deformations, particularly across dense ECM networks with subnucleus-scaled pore sizes, it may be easier for them to invade than more static cells. In nutrient-deprived regions, as in locations where large tumors are forming, energetic efficiency may be important in tumor activity, and invasion becomes more efficient for more aggressively invasive cells. Additionally, we showed that taxol treatment, which is a common therapeutic for metastatic breast cancer, increases the size of the cell and the initial transit time. Once the cell is conditioned after the initial deformation event, the relative difference in cell transit times becomes less distinguishable, suggesting that for aggressive cells, size may not be critical in the cost of invasion. Taxol, however, also reduces directionally polarized migratory behavior (M. Mak et al., *Lab on a Chip*, 2013, 13, 340-348; A. Takesono et al., *Plos One*, 2010, 5, e8774), which makes persistent invasion across confined barriers more difficult. This suggests that anti-invasion properties of taxol (M. Mak et al., *Lab on a Chip*, 2013, 13, 340-348; M. E. Stearns et al., *Cancer Research*, 1992, 52, 3776-3781) may result from a synergy of cell size increase and decreased directional persistence in migration, which would decrease the probability of occurrence of the initial deformation event and thus inhibit subsequent easier invasions.

The Strain Dynamics of Serial Deformations

Next we examined the serial deformation dynamics of cells in which cell 2 in the configuration in FIG. 10 was present. This allowed for more substantial cell relaxation over longer durations, on average over 3 minutes, between subsequent deformations. The results for the remainder of this paper will be based on this coupled-cell configuration in order to better appreciate both deformation and relaxation dynamics.

Our experiments show that even after prolonged relaxation, an initial deformation event facilitates subsequent deformations, as demonstrated in FIG. 12A. The initial deformation requires the longest time, and the strain vs. time curve displays several phases. Here, strain refers exclusively to the strain of each cell along the long axis of the channel, i.e. the length that the cell is stretched from equilibrium divided by the cell's equilibrium length. With respect to the strain rate of the cell, the three main phases identifiable are 1) the initial shortest and fastest phase followed by 2) a longer, stagnant phase then followed by 3) a moderately fast phase. Deformations across subsequent barriers have reduced or eliminated phases 2 and 3, enabling the cell to deform and transit across the barrier more easily.

To better gauge the nature of these phases, we stained the nuclei of live cells and performed simultaneous phase contrast and fluorescence imaging to distinguish relative contributions from the core of the cell (i.e. primarily the cytoskeleton) and the largest and stiffest organelle, the cell nucleus. FIG. 12B shows the kymograph of a typical cell transit event, and the transit phases are now more apparent. The first phase is when part of the cell can easily deform into the constriction (likely due to a simple force balance between the applied pressure and the initial elastic response of the cell) (N. Desprat et al., *Biophysical Journal*, 2005, 88, 2224-2233; 0. Thoumine et al., *Journal of Cell Science*, 1997, 110, 2109-2116). Phase 2 is when the nucleus is obstructed and its stiffness is too high to transit further into the constriction, as demonstrated by the nucleus being stuck at the constriction interface. However, a slow creep from its viscoelastic nature enables gradual permeation. Phase 3 is when the nucleus has deformed entirely into the constriction, leaving the remaining (less obstructive) portion of the cell to deform more quickly into the constriction. We note here that phase 3 in the initial transit is much longer than the entirety of the transit period of the subsequent transits shown in FIG. 12A. This shows that while the nucleus appears to be the most obstructive element in cell transit, the serial deformation effect is a reflection of the conditioning of both the nucleus and the cytoskeleton. Once the cell is conditioned, its subsequent transit dynamics have an altered behavior that is faster than both phase 2 and phase 3. FIG. 12C shows the kymograph of the same cell as in FIG. 12B deforming across a second barrier. The strain dynamics of the whole cell as well as that of the nucleus are altered; there is no nucleus obstruction phase and the cell transits through the entire constriction much more quickly.

It is noteworthy here that under a fixed cell-scaled force of 60 nN (via 400 pa of applied pressure completely dropped across the cell at the constriction), the cells examined in our experiments deformed and transited completely across the constriction within a matter of minutes (4.2±0.5 and 7.3±2 minutes for the first and thus longest deformation event through 10 µm-long and 60 µm-long constrictions, respectively). The times were even shorter for subsequent transits. This translates into comparable cell migration velocities in 3D gel studies (S. I. Fraley et al., *Nature Cell Biology*, 2010, 12, 598-604; C. M. Kraning-Rush et al., *Integrative Biology*, 2013, 5, 606-616), suggesting that simple creep strain dynamics under consistent force loads could play a basic role in cell invasion across subcellular-scaled confinements. For instance, even if an applied force from the cell is not sufficient to enable it to squeeze across a constriction instantaneously, the cell simply needs to wait while consistently applying a forward force, e.g. through actin polymerization, and viscoelastic creep will confer the cell a sufficiently deformed state to pass through the constriction. Thus, cell invasion may characteristically exhibit the coupling between both active (force generation) and passive (creep strain) processes. It is also notable that the phases observed here in the strain dynamics of flowing cells have qualitative similarities to the phases observed when cells are actively migrating across subnucleus-scaled barriers (P. Friedl et al., *Current Opinion in Cell Biology*, 2011, 23, 55-64; M. Mak et al., *Plos One*, 2011, 6; M. Mak et al., *Lab on a Chip*, 2013, 13, 340-348).

The Serial Factor

To assess and appreciate the impact of repeated deformations on cells, we need a way to measure a factor, which we will now call the "serial factor" SF, that quantifies the relative degree of difficulty for a cell to transit across constrictions after it squeezes across an initial constriction. A good candidate for SF is the ratio of the transit times $SF=t_s/t_i$, where $t_i$ is transit time across the first constriction and $t_s$ is the transit time across a subsequent constriction.

Figure 13:
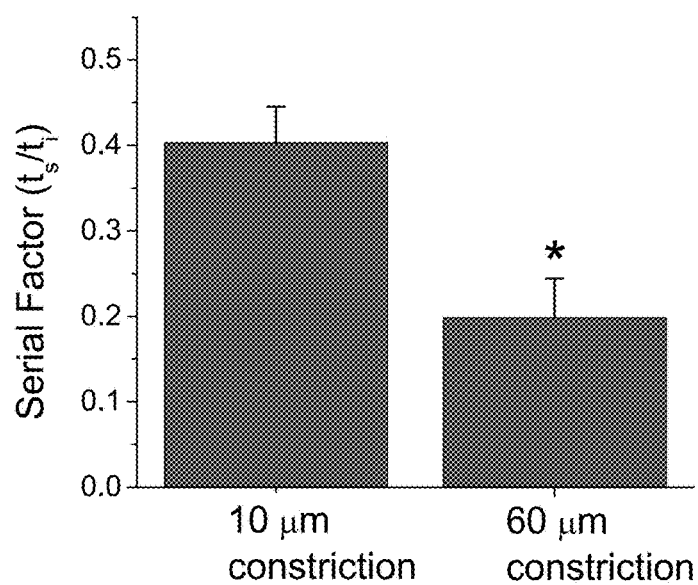
FIG. 13 illustrates the serial factor vs. constriction length, as observed in one embodiment of a microfluidic device/microfluidic system of the present invention. Shorter constrictions (10 µm) that only span a fraction of the total cell length exhibit a longer normalized transit time in subsequent constrictions ($t_s/t_i$=0.40±0.04, n=20) than longer constrictions (60 µm) that span most if not the entire deformed cell length ($t_s/t_i$=0.20±0.05, n=13). The serial factor is thus larger for cells experiencing larger initial strains. Error bars represent standard error of the mean, and * indicates p<0.01.

First, our results show in FIG. 13 that the average SF is larger for serial transits across shorter constrictions. The average SF is $0.40\pm0.04$ (n=20) and $0.20\pm0.05$ (n=13) for 10 μm-long serial constrictions and 60 μm-long serial constrictions, respectively, where n is the number of single-cell serial transit events. We note here that in this data, the strains on the cells before subsequent transits for the 10 μm-long and 60 μm-long serial micropipette experiments are $0.24\pm0.03$ (n=20) and $0.25\pm0.05$ (n=13), respectively, and they are not statistically different. This indicates that longer constrictions, which induce larger overall deformations on the cell, facilitate subsequent deformations to a larger degree, even after the cell is allowed to relax back towards equilibrium.

Next, we were interested in measuring SF as a function of the conformation of the cell after deformation in order to gauge how the shape or morphology of a previously deformed cell translates into its ability to deform across a subsequent constriction. Therefore, since we were conducting deformation and relaxation experiments on these cells, we were interested in the function $SF(J_r)$, where $J_r$ is the remaining strain on an initially deformed cell after it is given time to relax towards equilibrium. To derive this function, we considered previous micropipette studies that empirically characterized cells to exhibit a power-law creep under a fixed applied pressure, such that the creep strain is $J(t)=At^\alpha$, where A is a constant scaling prefactor, t is the time the cell is under the applied pressure, and $\alpha$ is the power-law scaling exponent. We note that this simple power-law relation does break down over the entirety of the cell and may be impacted by our simultaneous sampling of the nucleus and the cytoskeleton with subnucleus-scaled constrictions (K. N. Dahl et al., *Biophysical Journal*, 2005, 89, 2855-2864; N. Desprat et al., *Biophysical Journal*, 2005, 88, 2224-2233). However, for simplicity and in order to derive an empirical effective model, here we adopted the power-law approximation. Next we also assumed that A remains constant for the same cell under serial deformations such that all changes in cell strain behavior are then attributed to $\alpha$, which helps simplify our effective model. For our experiments, since most of the time the cell spends transiting across the barrier is time spent for the strain to increase until the cell reaches a conformation (i.e. when the cell is thin enough) that enables the cell to flow easily and rapidly through the constriction, we approximated $t_i$ and $t_s$ to be effectively the time when the cell strain is increasing under a constant applied pressure gradient. From this we derived SF as follows:

Since serial deformations are easier, the power-law scaling factor $\alpha$ is altered in subsequent deformations in comparison to the initial, such that there are two different strain dynamics relations:

$$J_1(t)=At^{\alpha 1} \quad (1a)$$

$$J_2(t)=At^{\alpha 2} \quad (1b)$$

where the indices 1 and 2 correspond to initial and subsequent strains, respectively. From this, we obtain:

$$J_i=J_1(t_i)=At_i^{\alpha 1} \quad (2a)$$

$$J_s=J_2(t_r+t_s)=A(t_r+t_s)^{\alpha 2} \quad (2b)$$

$$J_r=J_2(t_r)=At_r^{\alpha 2} \quad (2c)$$

where $J_i$ is the total strain from the initial deformation ($1^{st}$ transit), $J_s$ is the total strain in a subsequent deformation (the following serial transits), $J_r$ is the remaining strain on the cell after relaxation and before the next deformation event, and $t_r$ is the virtual time that it would require the cell to strain from 0 to $J_r$. The total strains on the cells are the same for each transit since they are deforming across identical subsequent constrictions so $J_i$ equals $J_s$ and it follows that:

$$t_i^{\alpha 1} = (t_r+t_s)^{\alpha 2} \quad (3a)$$

$$SF = \frac{t_s}{t_i} = t_i^{\frac{\alpha 1}{\alpha 2}-1}\left(1-\left(\frac{J_r}{J_1}\right)^{\frac{1}{\alpha 2}}\right) \quad (3b)$$

which gives an analytical form of SF. Next, we impose the condition that as the cell is allowed to relax completely to its equilibrium state after deformation, $\alpha_2$ would recover to $\alpha_1$:

$$\alpha_2=\alpha_1(1+C\times F[J_r/J_i]) \quad (4)$$

where C is a scaling coefficient and F is the normalized relaxation function that decays from 1 to 0 when the cell fully recovers (when $J_r/J_i=0$). From the data, SF decays sharply initially and then plateaus near 0, so therefore we choose a simple function that displays that form:

$$F = 1 - e^{-\frac{J_r}{k\times J_1}} \quad (5)$$

where $k*J_i$ is the characteristic decay length of F.

Figure 14:
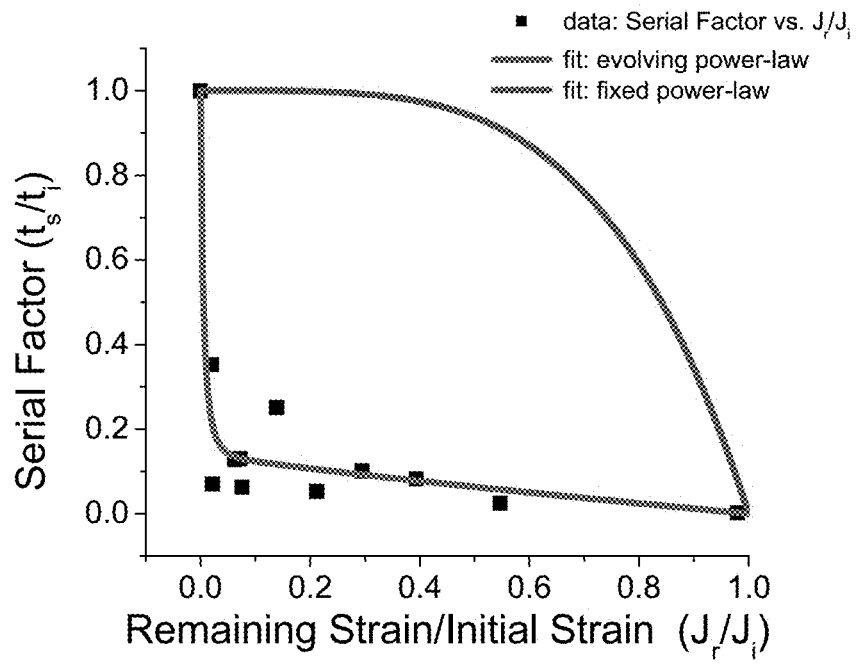
FIG. 14 illustrates the serial factor vs. normalized remaining cell strain, as observed in one embodiment of a microfluidic device/microfluidic system of the present invention. After an initial cell deformation across a 60 µm long subnucleus-scaled (3.3 µm×10 µm cross-sectional area) constriction, it becomes easier for cells to deform across subsequent (identical) constrictions. The relative degree of difficulty between subsequent and initial deformation processes can be interpreted from the relative transit times across the constrictions ($t_s/t_i$), i.e. the serial factor SF. As the remaining strain $J_r$ is increased (relative to the total initial strain $J_t$) signifying less relaxation before the subsequent deformation, the transit process becomes faster. Moreover, SF exhibits a sharp initial decay, which our modified power-law based model for SF captures (blue fitted curve, $R^2=0.92$). The conventional low strain, weak power-law model ($\alpha=0.25$) exhibits a different behavior (red curve).

FIG. 14 shows the SF vs. $J_r/J_i$ plot for the micropipette experiments with 60 μm-long constrictions. Only experiments from 60 μm-long constrictions were analyzed here because for 10 μm-long constrictions, since the constriction is shorter than the cell, there is non-uniform relaxation after cell transit (parts of the cell starts relaxing earlier than others), which complicates any analytical comparisons, particularly with our simple model. As shown in FIG. 14 by the blue fitted curve, the experimental data fits to our model for SF ($R^2$=0.92). Previous studies focusing on the low strain regime have shown that the strain dynamics exhibit a weak power-law dependence with $\alpha<1$ (K. N. Dahl et al., *Bio-*

Figure 15:
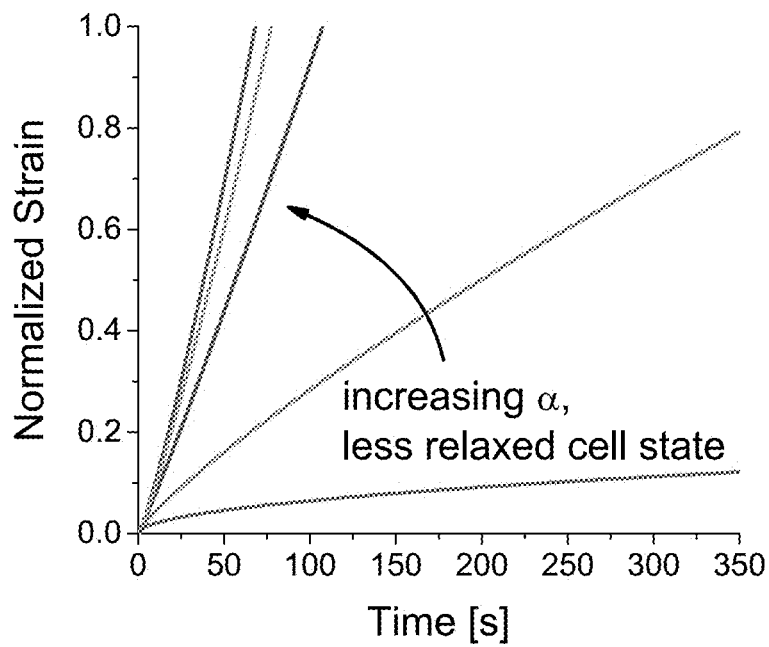
FIG. 15 illustrates strain dynamics under fixed pressure from the evolving power-law model. By assuming that the power-law scaling exponent a evolves based on the degree of relaxation of the cell state after an initial deformation, we plotted the normalized strain $J_N(t)=At^\alpha/J_i=t^\alpha/t_i^{\alpha 1}$ for different a's and recovered the typical behavior in serial strain dynamics under fixed pressure.

*physical Journal*, 2005, 89, 2855-2864; N. Desprat et al., *Biophysical Journal*, 2005, 88, 2224-2233; G. Lenormand et al., *Journal of The Royal Society Interface*, 2004, 1, 91-97). We calculated and plotted the red curve in FIG. 12 that assumes a constant $\alpha=0.25$, a typical value in the low strain regime. As demonstrated, the curvatures of the two calculated curves are different with one that is concave and one that is convex. The actual SF data is concave, illustrating that in the serial deformation scenario, it is applicable to consider an evolving a that becomes larger than 1. Without considering the serial effect, it would be difficult to fully appreciate the details and degree to which subsequent deformations are facilitated, which are especially relevant to physiological phenomena that require cells to deform repeatedly such as in migration and invasion. Using our model for an evolving $\alpha$ that is dependent on the remaining strain before subsequent cell deformations, we can recover the typical characteristics of J(t) for differentially relaxed cell states, as shown in FIG. 15.

Figure 16:
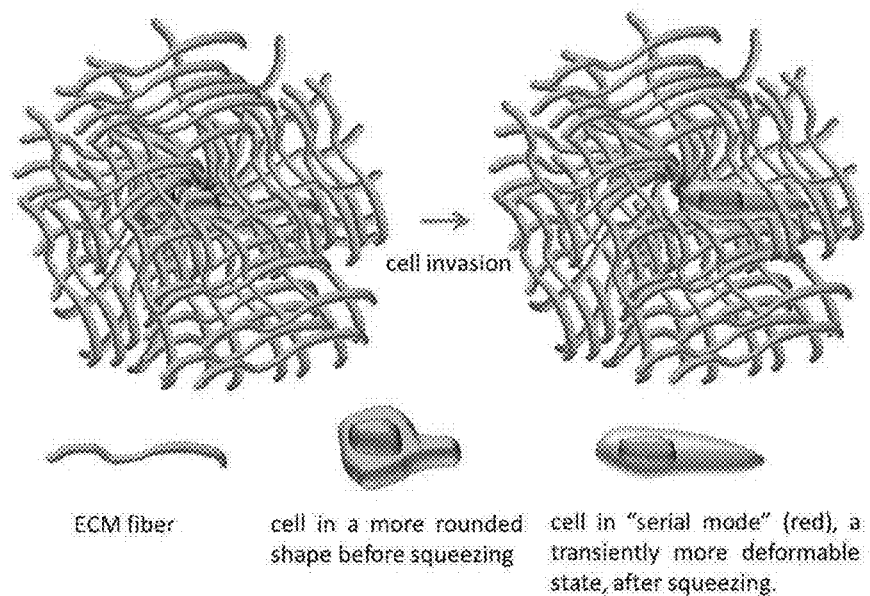
FIG. 16 is an illustration of the serial effect during cancer invasion. When a cell is in a more relaxed state and invades (non-proteolytically) across a constriction ring in the ECM, the cell is deformed and transiently enters a "serial mode" that exhibits a higher power-law scaling exponent in its strain dynamics, making the subsequent invasion events easier in accordance to the serial factor.

The results here show that unless a cell is allowed to relax completely back to its equilibrium state after a deformation event, any remaining strain indicates that the cell is in an enhanced "serial mode" that enables it to deform across subsequent constrictions more easily, in accordance to the serial factor. As illustrated in FIG. 16, this could have implications in the metastatic process in cancer, as non-proteolytic invasion induces cells to squeeze across narrow gaps that are often smaller than the cell nucleus, i.e. through constriction rings in the ECM (P. Friedl et al., *Current Opinion in Cell Biology*, 2011, 23, 55-64; K. Wolf et al., *The Journal of Cell Biology*, 2003, 160, 267-277). An initial invasion event would thus confer upon the cell faster strain dynamics that facilitate subsequent invasion through confining physiological barriers.

CONCLUSION

We developed a simple self-reliant system with no external parts or sources (syringe pumps, pressure manifolds, or other bulky connections that drive microfluidic devices) that requires only the loading of the cell samples of choice and performs multifaceted experiments in an automated manner without robotic assistance from programmable microscope stages, motorized parts, or other robotic actuators. We have demonstrated using this device that an initial cell deformation event, via a fixed cell-scaled force, conditions the cell for easier subsequent deformations, as the strain dynamics are altered. This conditioning is a function of the initial and remaining strain on the cell and may have physical implications for biological phenomena that require a multitude of deformation events, such as cancer invasion or immune cell diapedesis. We also gauged the contribution to the deformation strain dynamics from both the whole-cell body and the nucleus, which complements previous work that primarily considered only whole-cell boundaries or isolated nuclei or other intracellular components. Finally, we believe that the simplicity, form factor, automation, and multiple capabilities of this device can facilitate in a highly adoptable manner a broad array of cell mechanobiology studies, from measuring cell viscoelastic properties to disease diagnostics.

Example 3

Microfabricated Physical Spatial Gradients for Investigating Cell Migration and Invasion Dynamics We devise a novel assay that introduces micro-architectures into highly confining microchannels to probe the decision making processes of migrating cells. The conditions are meant to mimic the tight spaces in the physiological environment that cancer cells encounter during metastasis within the matrix dense stroma and during intravasation and extravasation through the vascular wall. In this study we use the assay to investigate the relative probabilities of a cell 1) permeating and 2) repolarizing (turning around) when it migrates into a spatially confining region. We observe the existence of both states even within a single cell line, indicating phenotypic heterogeneity in cell migration invasiveness and persistence. We also show that varying the spatial gradient of the taper can induce behavioral changes in cells, and different cell types respond differently to spatial changes. Particularly, for bovine aortic endothelial cells (BAECs), higher spatial gradients induce more cells to permeate (60%) than lower gradients (12%). Furthermore, highly metastatic breast cancer cells (MDA-MB-231) demonstrate a more invasive and permeative nature (87%) than non-metastatic breast epithelial cells (MCF-10A) (25%). We examine the migration dynamics of cells in the tapered region and derive characteristic constants that quantify this transition process. Our data indicate that cell response to physical spatial gradients is both cell-type specific and heterogeneous within a cell population, analogous to the behaviors reported to occur during tumor progression. Incorporation of micro-architectures in confined channels enables the probing of migration behaviors specific to defined geometries that mimic in vivo microenvironments.

Straight microchannels, a zeroth order environment (i.e. no perturbations in the direction of cell migration), provide limited means of extracting information about a cell's responsivity. By introducing small perturbations, higher order effects can be examined that may allow one to better understand how individual cells respond to a perturbation to its steady-state.

To accomplish this, here we have developed and conducted cell migration experiments in spatially tapered microchannels with cross-sectional areas comparable to the cell size. This provides a good model for cell navigation through physical constraints and spatial gradients, which are important during metastasis. Typical experiments (FIG. 17D) for weakly and strongly metastatic cells in these environments are shown. We demonstrate and compare the mechanical responsivity of three cell types: 1) bovine aortic endothelial cells (BAECs), which are a primary cell culture used here to provide basic insights toward mechanical and migratory behavior of adherent cells in tapered microchannels, 2) MCF-10A, a non-transformed human mammary epithelial cell line used here to represent non-metastatic cells, and 3) MDA-MB-231, a highly metastatic human cell line derived from metastatic breast carcinoma used in this study to model highly metastatic cells.

To date, most experiments involving engineered microenvironments and cell mechanics have been considered only in the steady-state. For instance, chemotactic responses, migration through straight confinement channels, and many other studies of cell migration, polarization, and morphology have only been characterized by average and steady-state velocities, directional persistence, and other ensemble averaged mechanical properties (Irmia D et al., (2009) *Integrative Biology* 1: 506-512; Rolli C G et al., (2010) *PLoS ONE* 5; Petrie R J et al., (2009) *Nature Reviews: Molecular Cell Biology* 10: 538-549; Abhyankar V V et al., (2008) *Lab Chip* 8: 1507-1515). Cell behavior, however, is governed by both spatially and temporally varying molecular signals and feedback (Dieterich P et al., (2008) *Proc Natl Acad Sci USA* 105: 459-463; Brandman O et al., (2008) *Science* 322:

390-395; Kholodenko B N (2006) C Nature Reviews: Molecular Cell Biology 7: 165-176; Parsons J T et al., (2010) Nature Reviews: Molecular Cell Biology 11: 633-643; Ridley A J et al., (2003)

Science 302: 1704-1709). These transient dynamics, such as the activation of intracellular processes in response to external mechanical or chemotactic stimuli, have not been considered in great detail. In this study, we investigate the transient cell dynamics caused by spatial, physical gradients.

Methods

Cell Culture

BAECs (VEC Technologies) were maintained at 37° C. and 0% $CO_2$ in Leibovitz L-15 media supplemented with 10% Fetal Bovine Serum and 1% Pen/Strep. Experimentation was conducted using the same media under the same condition.

MDA-MB-231 cells from the American Type Culture Collection (ATCC, HTB-26) were maintained at 37° C. and 5% $CO_2$ in DMEM supplemented with 10% Fetal Bovine Serum. Experimentation was conducted in the same condition except with DMEM replaced by L-15 and at 0% $CO_2$.

MCF-10A cells from the ATCC(CRL-10317) were maintained at 37° C. and 5% $CO_2$ in DMEM/F12 supplemented with 5% Horse serum, 0.5 µg/ml Hydrocortisone, 20 ng/ml hEGF, 10 µg/ml Insulin, 100 ng/ml Cholera toxin, 100 units/ml Penicillin, and 100 µg/ml Streptomycin. Experimentation was conducted in the same condition except with the addition of 10 mM HEPES buffer and at 0% $CO_2$. During experiments, the pH of cell culture media was monitored periodically by observing the color of the media due to the phenol red dye. No significant changes were seen. Furthermore, fresh media with the addition of 10 mM HEPES buffer for pH stabilization were replenished every 24 hours.

Note: The media used for each cell type are based on the ATCC (American Tissue Culture Collection) or National Institutes of Health Physical-Sciences and Oncology Center specifications, also delineated by Debnath J et al., (2003) Methods 30: 256-268 and Guise T A et al., (1996) J Clin Invest 98: 1544-1549.

Microchannel Fabrication

As shown in FIG. 18B, standard contact photolithography is used to generate an SU8 (MicroChem, Newton, Mass.) on silicon master that is used to create PDMS (10:1 silicone elastomer to curing agent ratio) (Dow Corning, Midland, Mich.) molded microchannels, which are bonded to a glass slide. In the designed pattern, as shown in FIG. 18A, a tapered junction of variable spatial gradient connects a large (cross-sectional area: 15 µm×10 µm) channel with a small (4 µm×10 µm) channel.

Cell Loading and Preparation for Experiments

Two fluidic injection ports are incorporated into the microchannel device—one on the side of the larger channels (inlet) and one on the side of the smaller channels (outlet). Cells are loaded into the inlet and allowed to proliferate and migrate into the larger channels. During experiments, devices are placed on top of a heating stage maintained at 37° C.

Cell Migration Trajectory and Velocity Tracing

Timelapse microscopy conducted on an inverted microscope with a 10× objective, with a temporal resolution of 2.88 min/frame, was used to record cell migration in microchannels. The center of mass of cells was tracked manually through image stacks using ImageJ, and velocities were calculated by linear approximation with adjacent frames. Each velocity data point was then averaged with the neighboring 10 points for smoothening and noise filtering.

Statistical Analysis of Cell Permeation Vs. Repolarization

Since we are considering a binary system and assuming the behavior of each cell represented by the data can be considered as an independent event, the statistics should follow the Bernoulli distribution. The statistical variance v of the cell behavior is then pq, where p and q are the probabilities of cell permeation and repolarization, respectively. By the central limit theorem (Feller W (1945) Bull Amer Math Soc 51: 800-832) for a sample of size n, the error of estimating p (and q) from our experimentally acquired value of $p_e$ (and $q_e$) should follow a normal distribution. Mathematically:

$$N(0, 1) = \frac{n \times (p_e - p)}{\sqrt{n \times v}}$$

where N(0,1) is notation for the standard normal distribution. To calculate confidence intervals:

$$p_e = N(0, 1) \times \sqrt{\frac{v}{n}} \leq p \leq p_e + N(0, 1) \times \sqrt{\frac{v}{n}}$$

and N(0,1) is 1.96 for 95% confidence and v is approximated by our experimental values as $p_e q_e$. For further details see Feller W (1945) Bull Amer Math Soc 51: 800-832.

Results

Heterogeneity and Statistical Behavior

Figure 18:
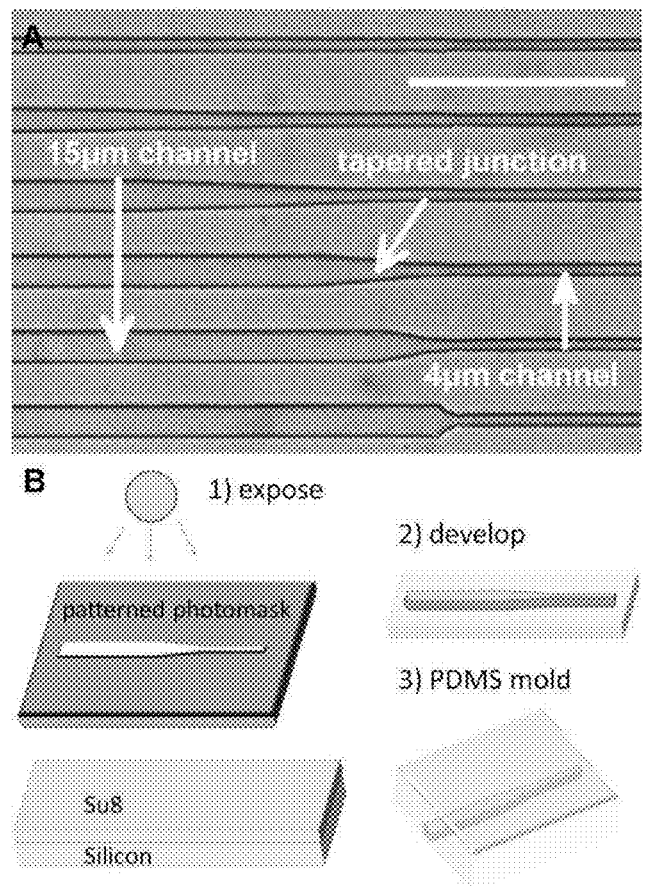
FIGS. 18A-18B illustrate design patterns and a device fabrication process of one embodiment of a microfluidic device/microfluidic system of the present invention.

To investigate the migratory response of cells to physical spatial gradients, we designed an array of PDMS microchannels bonded to a glass substrate. The device design and fabrication procedure are shown in FIG. 18. Each channel consists of a tapered junction of variable spatial gradient that connects a large (cross-sectional area: 15 µm×10 µm) channel with a small (4 µm×10 µm) channel. Six different gradients are incorporated, and for the studies here they are categorized as either "high" (tapering angle larger than 7 degrees) or "low" (tapering angle smaller than 3 degrees) gradients (see FIG. 18 caption for more details). Cells migrate unidirectionally in the large channel towards the small channel and their behavior in the tapered region is observed via timelapse microscopy (approximately 24 hrs per experiment) and analyzed. See methods section for more details on the fabrication of the microfluidics.

Figure 19:
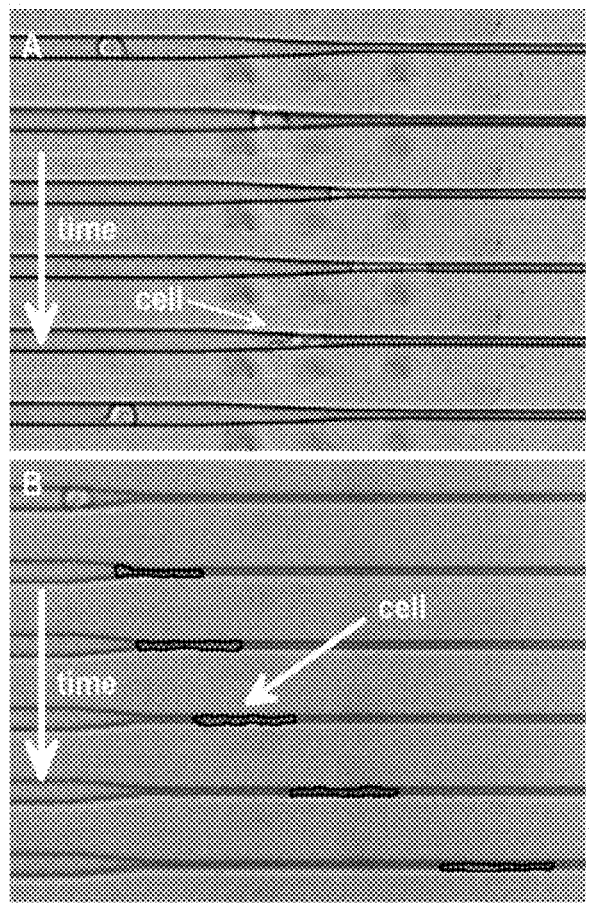
FIGS. 19A-19B illustrate heterogeneous cell behavior in tapered junctions, as observed in one embodiment of a microfluidic device/microfluidic system of the present invention. Timelapse montage of a cell (MCF-10A) turning back once reaching the tapered region (each frame is 0.96 hrs) (FIG. 19A) and permeating into the smaller channel (each frame is 2.5 hrs) (FIG. 19B). Width of larger channel is 15 µm. Supplementary materials for timelapse videos of all 3 cell types were studied as well.

We characterize the cell as a two-state system where each state corresponds to its polarization, which is determined here based on the direction of cell migration. Since the cell is confined to migrate in 1D, only two polarizations exist, forward and backward. We measure the probability of occurrence of each state upon a cell's interaction with the tapered geometry. Specifically, the two states are determined as: 1) a cell penetrating through the tapered junction and permeating into the smaller channel (i.e. the entire cell body is inside the smaller channel), and 2) a cell turning around (repolarizing) once reaching the tapered region and migrating in the backwards direction. Sample experiments demonstrating both states are shown in FIG. 19, and timelapse movies of various cell types migrating in the devices and exhibiting various behaviors. All cells considered are initially migrating in the direction pointing from the larger channel to the smaller channel. To account for random repolarizations due to distance traveled and the different lengths of tapered junctions of different spatial gradients, a fixed interaction length (250 µm between tapered region and start of small channel) is considered for each cell. All and only cells entering this region are considered, so random repolarizations due to distance traveled are weighted equally in all junctions. Furthermore, cells that die or have not made a conclusive decision by the end of each timelapse experiment are ignored. Cells interacting with other cells are also ignored.

First, our results demonstrate the non-trivial existence of these two states, as both have been observed with appreciable frequency. We have identified two distinct migratory phenotypes, permeating cells and repolarizing cells. Here, phenotype refers to any observable characteristic or behavior of the cell. The occurrence of these two states enables us to quantify migratory invasiveness both in the same cell population and across different cell types with a simple binary analysis. We characterize these events by their probability of occurrence and show that there is a significant dependence of this property on both the spatial gradient of the tapered junction and the cell type.

Figure 20:
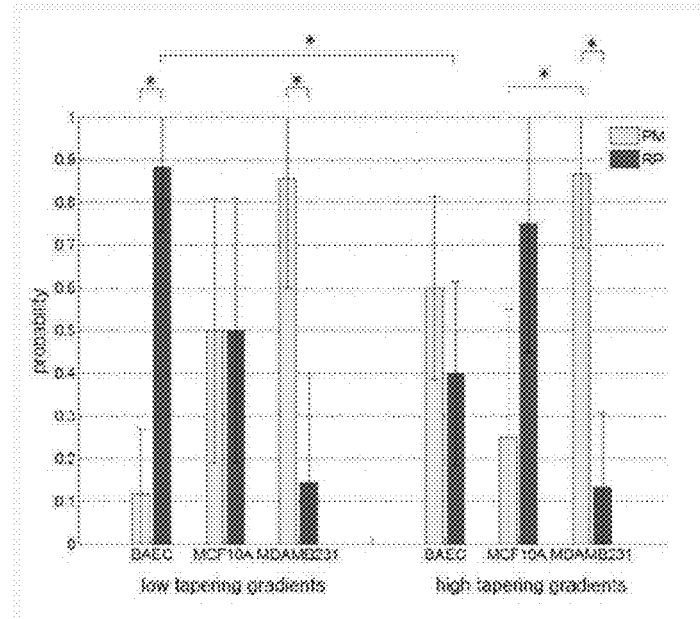
FIG. 20 is a graph illustrate cell behavior statistics at the tapered junction. Data plots showing the probability of cell permeation (PM, yellow) and repolarization (RP, red) for low and high gradient tapers for three different cell types. Error bars represent 95% confidence intervals calculated from the standard deviation of Bernoulli experiments. * denotes statistical difference, p-value <0.05, between data at the nodes of each line.

FIG. 20 shows the response of different cell types to the spatial gradient of the tapered junction. For BAECs, the probability of permeation (into the small channel once reaching the tapered region from the large channel) is greater for higher spatial gradients (60%, n=20) than for lower gradients (12%, n=17) ($p<0.05$). In other words, more gradual transitions tend to induce cells to repolarize more often. Furthermore, for the subset of cells that experience this more gradual transition, the probability of repolarization (88%) is statistically higher than permeation (12%) ($p<0.05$). For MCF-10A's, the probability of permeation is 50% (n=10) for low gradients and 25% (n=8) for high gradients. For MDA-MB-231's, the probability of permeation is 86% (n=7) for low gradients and 87% (n=15) for high gradients.

The response of highly metastatic MDA-MB-231 cells shows several distinguishing features. First, the probability of permeation for both low and high gradients is statistically greater than the probability of turning around ($p<0.05$). For low gradient tapers, this result is opposite to that of BAECs. Next, in comparison with non-metastatic breast epithelial cells (MCF-10A's), MDA-MB-231 cells exhibit a statistically higher ($p<0.05$) probability of permeation for high gradient tapers. These differences, particularly the latter case, can potentially be distinguishing factors between highly metastatic cells and non-metastatic cells. A higher probability of permeation in a spatially tapered and highly confining microenvironment for a particular cell type may indicate greater invasiveness in the context of cancer metastasis.

It has been shown previously that small channels which force cells to deform significantly in order to enter have a much lower probability of cell permeation upon contact (Rolli C G et al., (2010) PLoS ONE 5). Our results, particularly for MDA-MB-231's, show that there is a substantial permeative population into the smaller channel despite such highly constrictive spatial domains. This may imply that once a cell has entered into a mode of 1D unidirectional migration, its permeative and invasive capabilities are enhanced, at least in the direction of motion. Physiologically this may suggest that there is a feedback mechanism that once a metastatic cancer cell has entered into a defined track in the extracellular matrix or microvasculature, it gains increased aggressiveness during invasion into more confining spaces.

Cell Transition Dynamics and Signaling Feedback on the Single Cell Level

The tapered channel assay presented above can also be used as a label-free method of quantitatively characterizing signaling feedback on the single cell level by analyzing the mechanical responsivity of cells and profiling cell migration transition dynamics. Responsivity is the factor that maps an external input to an output of interest. Here, the input is the transformation of space and the output is the induced cell migration dynamics. Cell dynamics involve intracellular signaling which entails feedback loops to ensure a robust and rapid cell response. Feedback (whether electrical, mechanical, or biological) can often manifest mathematically as an exponential (sigmoid) curve (Brandman O et al., (2008) Science 322: 390-395; Kholodenko B N (2006) C Nature Reviews: Molecular Cell Biology 7: 165-176). Therefore, we fit the velocity profile of cells migrating in the spatially tapered region into sigmoid curves and derive characteristic transient constants. We note the sequential activation of two feedback loops (one negative and one positive). The model we used for curve fitting is:

$$\text{velocity} = \frac{v_i - v_{f1}}{1 + \exp(c_1(t - t_{01}))} + \frac{v_f - v_{f1}}{1 + \exp(-c_2(t - t_{02}))} + v_{f1}$$

where $v_i$ is the initial steady-state velocity, $v_f$ is the final steady-state velocity, $1/c_1$ is the time constant of the first sigmoid, $1/c_2$ is the time constant of the second sigmoid, $t_{01}$ is the time for the mid-point of the first sigmoid, $t_{02}$ is the time for the mid-point of the second sigmoid, and $v_{f1}$ is the final steady-state velocity if the second sigmoid is not present. By analyzing the temporal evolution of the cell's velocity, we can extract several key parameters of the transition process—1) the time constants of the sigmoid curves (the net signaling feedback loops) and 2) the temporal delay between the activation of the two net signaling processes ($t_{02}-t_{01}$).

The first process is a negative feedback loop that diminishes the speed of the cell as it encounters additional spatial constraints (i.e. the spatial taper). The second process is a positive feedback loop that accelerates the cell to a steady-state velocity in the direction it has chosen to pursue after encountering the spatial gradient. The delay in the activation of these two signaling processes is likely time used to reorganize the cell's cytoskeletal network for permeation into a more confining channel or repolarization for migration in a different direction.

Figure 21:
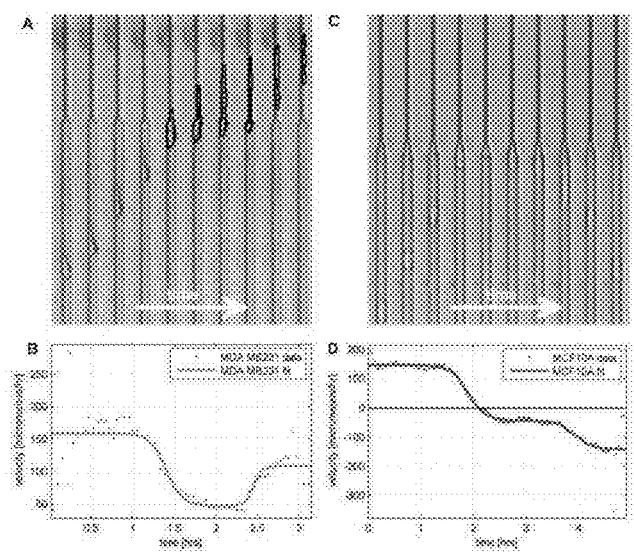
FIGS. 21A-21D illustrate migration dynamics of repolarizing and permeating cells, as observed in one embodiment of a microfluidic device/microfluidic system of the present invention.
Figure 22:
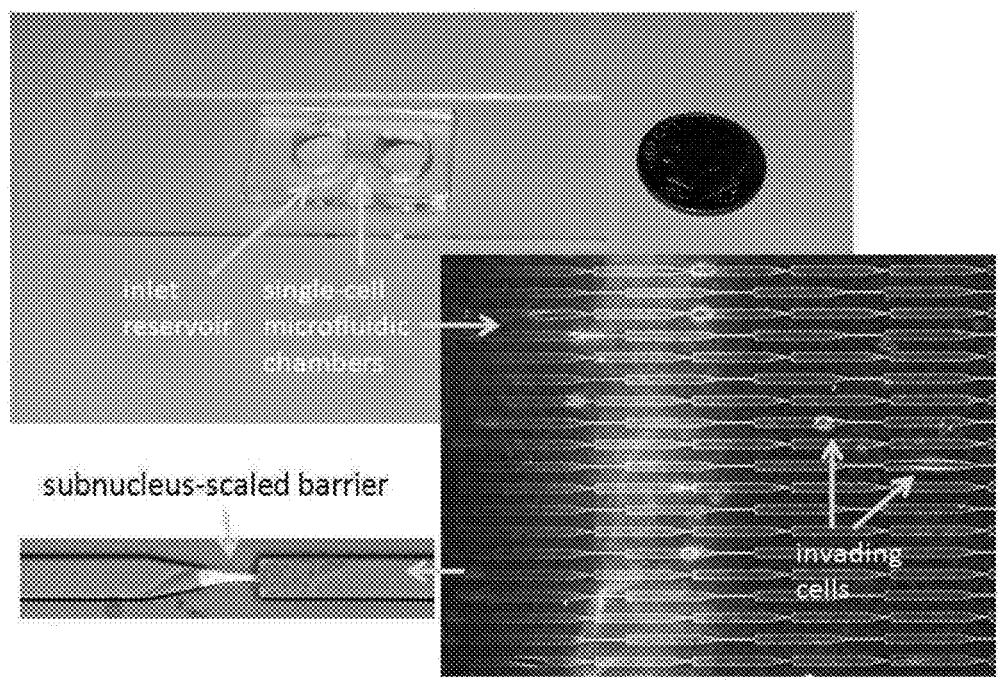
FIG. 22 illustrates an embodiment of a microfluidic device/microfluidic system prototype of the single-cell drug screening assay. Cells are loaded from the inlet reservoir into the microfluidic chambers (insets) at one cell per chamber and single-cell behaviors and emergent drug resistant phenotypes can be studied from isolated single-cell lineages. The constriction region in these channels is smaller than the cell nucleus, as visualized via fluorescence staining of the nucleus. This provides a highly confined barrier for invasion studies as well as a constriction interface to enable single-cell loading per channel. This design can be scaled up and incorporated into a 96-well plate format to accommodate high-throughput drug screening with existing drug development technologies and infrastructures.

Two time constants and a delay constant provide suitable curve fits for the velocity profile of cells undergoing this transition. For example, as shown in FIG. 21A for a permeating cell, the two time constants are 6 and 3 minutes, respectively, and the delay constant is 1 hour, and as shown in FIG. 21B for a repolarizing cell, the two time constants are both approximately 10 minutes and the delay constant is 2 hours. Time and delay constants for different cells can vary (from minutes to hours) indicating potentially diversity in signaling pathways at play and the cytoskeletal complex of individual cells. This illustrates the importance of considering single cell dynamics rather than ensemble averages, particularly for the analysis of cancer cell mechanics since metastatic potential may be dictated by heterogeneous subpopulations displaying more invasive characteristics (Visvader J E et al., (2008) Nature Reviews Cancer 8: 755-768; Shackleton M et al., (2009) Cell 138: 822-829; Fidler I J (1978) Cancer Research 38: 2651-2660). This method presents a way of measuring the signaling of a net biological process which may be more meaningful than the expression of individual signaling molecules that may contribute to a multitude of pathways and phenotypes.

Discussion

In this study, we have investigated the migratory behavior of different cell types in response to physical spatial gradients. We focused on the transition region connecting a larger channel to a smaller channel and demonstrated the effect of varying the spatial gradient of the junction on cell responsivity. We also showed that the highly metastatic cells used here (MDA-MB-231's) have a statistically higher permeative nature into smaller regions than non-metastatic cells (MCF-10A's), at least when the spatial gradient is high.

Figure 17:
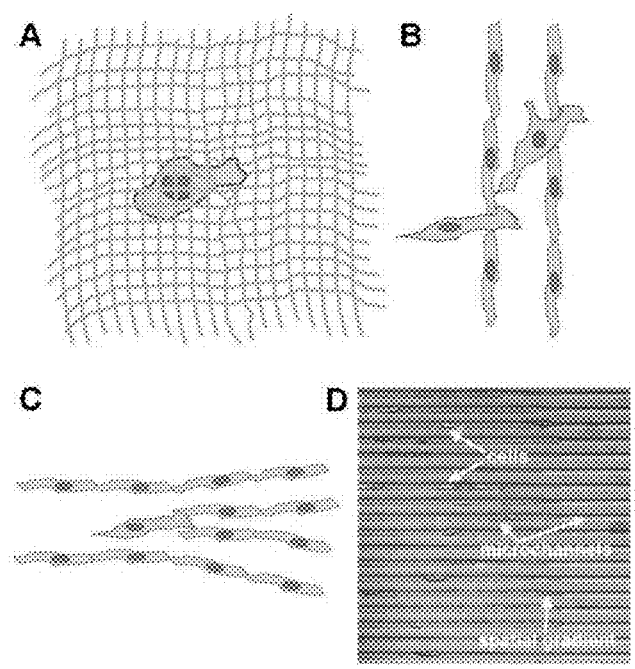
FIGS. 17A-17D illustrate cells encountering spatial gradients in physiological and simulated environments. A cancer cell (orange) is navigating through small pores in the extracellular matrix (green) as it is invading through the tumor stroma (FIG. 17A), squeezing through the endothelium (red cells) during intra- and extravasation (FIG. 17B), and encountering vessel branch points upon migration in the microvasculature (FIG. 17C).

Previous work that used highly confining environments to study cell migration and adhesion dynamics has primarily involved straight and symmetric microchannel structures. For example, Jacobelli J et al. ((2010) Nature Immunology 11: 953-961) demonstrated that myosin IIA regulates the crawling mode of T-cell migration by analyzing the "walking" and "sliding" adhesion dynamics of T-cells when migrating in straight confinement microchannels. Hawkins et al. ((2009) Physical Review Letters 102: 058103) developed a mathematical model that addresses spontaneous motion in narrow channels based on actin polymerization within a model cell. Furthermore, Irmia and Toner ((2009) Integrative Biology 1: 506-512) demonstrated that mechanical confinement can induce spontaneous unidirectional migration in cells, and migration rates are affected by microtubule-disrupting drugs such as Taxol and Nocodazole. These studies clearly showed the rich information about cell mechanics and motility that can be extracted by imposing physical constraints in the cells' local microenvironment. However, the data from these previous experiments were based on spontaneous cell reactions in a static environment with no perturbative features for stimulating cell responsivity. Very little information can be extracted about cell behavior at barriers and interfaces, which is especially important when considering metastasis, during which cancer cells are often transitioning across impeding junctions and into new environments. One such interface is the increase in physical constraint (as illustrated in FIG. 17), which our assay simulates. By introducing a spatially tapering region into microchannels, cells are stimulated at the interface and responses are induced. Therefore, stimulated dynamics rather than steady-state or spontaneous reactions can be studied.

Additionally, we elucidated the existence of behavioral differences within a common cell type in response to a tapered microgeometry; all cell types used here exhibited both permeating and repolarizing subpopulations. The existence of these two states demonstrates phenotypic heterogeneity in mechanical invasiveness among a common population of cells. Whether this heterogeneity is static or dynamic (i.e. whether the same cells always exhibit the same phenotype or this phenotype fluctuates in time for all cells) and the implications of either are currently not known and further studies are required. Heterogeneous subpopulations in tumors have been shown (Al-Hajj M et al., (2003) Proc Natl Acad Sci USA 100: 3983-3988; Li C et al., (2007) Cancer Research 67: 1030-1037), but the contributions to metastatic potential are not well understood (Kelly P N et al., (2007) Science 317: 337; Visvader J E et al., (2008) Nature Reviews Cancer 8: 755-768; Shackleton M et al., (2009) Cell 138: 822-829). Our technique presents a way of probing this heterogeneity based on mechanical properties on a single cell level.

Furthermore, migration dynamics under transition phases can provide insights into the mechanical responsivity of cells that can ultimately be mapped to intracellular signaling feedback mechanisms. For instance, one of the key contributors to cell locomotion is the actin machinery, where the polymerization and depolymerization of actin filaments provide force that drives cells in the direction of motion (Theriot J A et al., (1991) Nature 352; Barak L S et al., (1980) Proc Natl Acad Sci USA 77: 980-984). The velocity of cells then should be approximately proportional to the number of actively contributing actin filaments, and the velocity profile measured in this study should therefore be representative of actin signaling dynamics (i.e. the concentration profile of actin in the polarized edge of the cell, with negative values indicating that the polarization has changed directions).

Finally, our data indicate that metastatic MDA-MB-231 cells exhibit a more invasive phenotype (greater motility through the high gradient channels) than non-metastatic MCF-10A and BAECs. Because metastasis is a highly physical process that involves cell migration and deformation, our microfabricated system may have uncovered a novel mechanism by which metastatic cells enter narrow capillary beds of organs—cells may move through capillaries through active migration rather than simply passive flow transport. In our system, high and low gradient tapers may simulate vessel branch points and continuation along the main branch, respectively. Overall, by introducing additional parameters, e.g. variable geometric constraints, in engineered microenvironments, more information can be deduced about cell-environment interactions, such as mechanical triggers for cell repolarization and stability and persistence of cell polarization when perturbed externally. Investigation of the migratory response of cells to spatial constrictions could be valuable in elucidating other mechanical markers of metastasis.

As with most in vitro experimental systems, there are important caveats to address. Two important properties are the compliance of the materials used and the dimensionality of the system compared with physiological environments. The boundaries of our microchannels are glass, which is effectively purely rigid, and PDMS (10:1 ratio of silicone elastomer to curing agent), which has an elastic modulus of around $10^3$ kPa (Balaban N Q et al., (2001) Nature Cell Biology: 466-472; Brown X Q et al., (2004) Biomaterials 26: 3123-3129). Typical physiological surfaces that cells adhere to are soft and viscoelastic tissues comprising of the extracellular matrix and other cells (with elastic moduli between 10-10000 Pa) (Bao G et al., (2003) Nature Materials 2: 715-725; Wakatsuki T et al., (2000) Biophysical Journal 79: 2353-2368; Yeung T et al., (2005) Cell Motility and the Cytoskeleton 60: 24-34; Discher D E et al., (2005) Science 310: 1139-1143), which can be deformable under cellular forces (Balaban N Q et al., (2001) Nature Cell Biology: 466-472; Bao G et al., (2003) Nature Materials 2: 715-725; Califano J P et al., (2010) Cellular and Molecular Bioengineering 3: 68-75; Kraning-Rush C M et al., (2011) Physical Biology 8: 015009). Strong connective tissue and blood vessel walls can have elastic moduli on the order of 1 MPa (Brown X Q et al., (2004) Biomaterials 26: 3123-3129; Wakatsuki T et al., (2000) Biophysical Journal 79: 2353-2368). The complexity of the physiological environment, with such properties as non-uniform pore sizes and varying viscoelasticity in addition to dynamically regulated chemical signaling and proteolysis (Discher D E et al., (2005) Science 310: 1139-1143; Pathak A et al., (2011)

Integrative Biology 3: 267-278; Friedl P et al., (2009) Cancer Metastasis Rev 28: 129-135; Zaman M H et al., (2006) Proc Natl Acad Sci USA 103: 10889-10894; Bloom R J et al., (2008) Biophysical Journal 95: 4077-4088; Suresh S (2007) Acta Materialia 55: 3989-4014), makes it difficult to quantitatively analyze the fundamental principles of any physical processes. To begin to derive the governing properties of cell migration and invasion, it is important to simplify the experimental domain. With our assay, we are essentially considering a limiting case in which the compliance is low (relative to soft tissues) at the microchannel walls and infinite inside and along the channel. By reducing the width of the channel through physical tapering, we are reducing the "effective compliance" as experienced by the cells. Similarly, the dimensionality of our microchannel system can be considered as either 1-D, since cells are primarily moving along one axis, or pseudo 3-D, since cells can adhere to and interact with the four surrounding walls. Typical experiments that are supposed to mimic more physiological 3-D environments are conducted with cells embedded in extracellular matrix-simulating gels (Zaman M H et al., (2006) Proc Natl Acad Sci USA 103: 10889-10894; Wolf K et al., (2009) Clin Exp Metastasis 26: 289-298; Shields J D et al., (2007) Cancer Cell 11: 526-538). Fraley et al. ((2010) Nature Cell Biology 12: 598-604), for example, demonstrated that cell motility in these 3-D environments does not rely significantly on focal adhesion formation and depends on traction between cell protrusions and the surrounding matrix, both of which are different than 2-D motility. While 3-D experiments are excellent in elucidating more physiological mechanisms of cell motility, it is difficult to simulate and modulate interfaces, which as mentioned throughout this paper have important physiological consequences, in 3-D gels. Furthermore, the cell-in-gel model may not be the most accurate with regards to cell dynamics in microcapillaries, where the surrounding matter is the vessel wall and the interior is fluid (e.g. Yamauchi et al. ((2008) Cancer Research 68: 516-520) showed that cell dynamics in microvessels are relevant during the metastatic process). One of the main advantages of the confined microchannel approach is the ability to introduce and tune interface geometries. Ultimately, our tapered channel assay enables the quantitative analysis of the ability of a cell to transition from a region with higher degrees of freedom in movement to a region with lower degrees of freedom. Extensions of this assay could incorporate extracellular matrix components and multiple cell types in the channels to simulate more physiological conditions.

Example 4

High-Throughput Method for Screening Populations of Metastatic Cancer Cells

This example describes a proposed project to develop a high-throughput method for screening populations of metastatic cancer cells for the individuals that exhibit the highest levels of chemotherapeutic resistance. Identifying these outliers and ultimately the cause of their resistance to therapeutic intervention could lead to the development of more effective drug development and dosing schemes.

Microfluidic techniques are ideal to enable these studies because of the scale matching between device and cell features as well as the demonstrated capability for high throughput (Mahmud, G. et al., Nature Physics, 2009. 5: p. 606-612; Irmia, D. et al., Integrative Biology, 2009. 1: p. 506-512; Gabriele, S. et al., Lab on a Chip, 2010. 10: p. 1459-1467; Walter, N. et al., Biointerphases, 2011. 6: p. 117-125; Gabriele, S. et al., Biophysical Journal, 2009. 96: p. 4308-4318; Shelby, J. P. et al., Proc. Natl. Acad. Sci. USA, 2003. 100: p. 14618-14622; Hou, A.A.S.B.H. W. et al., Lab on a Chip, 2011. 11: p. 1870-1878; Chaw, K. C. et al., Lab on a Chip, 2007. 7: p. 1041-1047). We have recently developed a microfluidic assay—the Multi-barrier Serial Invasion Channels (MUSIC) device—that enables the serial sampling of individual metastatic cells and interrogation of their invasion properties in a highly parallel manner. Here, we aim to expand this technique and develop an integrated cancer resistance assay that can track the emergence of chemoresistance across single-cell lineages and uncover the fundamental evolutionary dynamics behind chemotherapeutic failure. Because cancer is driven by Darwinian evolution that selects for phenotypic (rather than genotypic) fitness under ecological stress (Hanahan, D. et al., Cell, 2011. 144: p. 646-674; Gillies, R. J. et al., Nat Rev Cancer, 2012. 12(7): p. 487-493), understanding the evolutionary principles at the fundamental scale of this ecology—the single-cell scale—can enable the development of new therapeutic strategies that modulate this evolutionary game and specifically target the emergence of resistance rather than the conventional target of specific cancer cell genomic signatures that will ultimately change and perpetually select into new and resistant profiles. This assay will give a metric that will assess whether resistance is targeted.

Various objectives are intended to be addressed by the project described in this example, including, those described below:

Objective 1—Create and Optimize a Simple, Ubiquitously Practicable Assay that Interfaces 1000 Microfluidic Channels with Single-Cell Cancer Biology for the Study of Chemoresistance.

Cell and nucleus-scaled microchannels will be developed that enable the isolation of one cell per chamber and the study of mechanical cell invasion and single-cell lineage proliferation.

Objective 2—Track and Analyze Morpho-Metrically the Evolutionary Fitness and Dynamics of Each Single-Cell Lineage Under Chemotherapeutic Treatment.

Here, we aim to analyze the variance in responsivity across single-cell lineages to pharmacologic effects and assess cancer heterogeneity and the evolution of this heterogeneity over time under chemotherapeutic stress. We will start with MDA-MB-231 cells, a highly metastatic breast adenocarcinoma cell line, and we will assess the effects of Paclitaxel, a commonly used anti-mitosis and anti-invasion chemotherapeutic drug that is susceptible to resistance.

Objective 3—Extract Individual Resistant Cell Lineages to Screen for Common Genotypes in Resistant Phenotypes.

Evolution could lead to any number of genomic differences that can confer a fit and resistant phenotype, such as tubulin mutations (against taxanes) (Verdier-Pinard et al., Oncogene, 2003. 22: p. 7280-7295; Wiesen, K. M. et al., Cancer Letters, 2007. 257: p. 227-235; Kavallaris, M. et al., J. Clin. Invest, 1997: p. 1282-1293; Giannakakou, P. et al., The Journal of Biological Chemistry, 1997. 272: p. 17118-17125; Jordan, M. A. et al., Nature Reviews Cancer, 2004. 4: p. 253-265), p-glycoprotein mediated multi-drug resistance (Pgp MDR) (Donnenberg, V. S. et al., J Clin Pharmacol, 2005. 45: p. 872-877; Greenberger, L. M. et al., Proc. Natl. Acad. Sci. USA, 1988. 85: p. 3762-3766; Li, X. et al., Analytical Chemistry, 2008. 80: p. 4095-4102), and drug resistant genes (Swanton, C. et al., Cancer Cell, 2007. 11: p. 498-512). However, it may be possible that there are some common precursor genes that facilitate evolution, e.g. stem-like properties (Donnenberg, V. S. et al., J Clin Pharmacol, 2005. 45: p. 872-877; Shackleton, M. et al., Cell, 2009. 138: p. 822-829; Dean, M. et al., Nat Rev Cancer, 2005. 5(4): p. 275-284; Dingli, D. et al., Stem Cells, 2006. 24: p. 2603-2610; Hermann, P. C. et al., Cell Stem Cell, 2007. 1: p. 313-323; Liu, G. et al., Molecular Cancer, 2006. 5), and such genes can be identified by considering the relative gene expression profiles of different drug-resistant phenotypes of the same tumor. Understanding the dynamics and mechanisms of each resistant variant can help in the development of new therapeutics (Goldie, J. H., Cancer and Metastasis Reviews, 2011. 20: p. 63-68; Komarova, N. L. et al., Proc. Natl. Acad. Sci. USA, 2005. 102: p. 9714-9719; Garnett, M. J. et al., Nature, 2012. 483: p. 570-575; Gascoigne, K. E. et al., Journal of Cell Sciences, 2009. 122: p. 2579-2585).

In order to understand heterogeneity at its fundamental scale—the cell scale since heterogeneity is ultimately a description of cell-to-cell variability—it is necessary to develop a new model that focuses beyond bulk samples. In this proposal, we aim to devise a ubiquitously practicable integrated cancer resistance assay by taking advantage of microfluidic techniques (prototype shown in FIG. 22) that enable a high throughput analysis of cancer heterogeneity at the single-cell level, and we will implement this assay to assess the emergence of chemoresistance from parallel single-cell lineages. By understanding the fundamental principles of cancer heterogeneity and evolution, we can more clearly identify the key elements that drive clinical failure in treating metastatic disease and better treatment regimens can be designed.

The innovation in our approach is that our high-throughput integrated cancer resistance assay is aimed at directly assessing the drug-induced emergence of phenotypes of interest at the single-cell level and uncovering the fundamental evolutionary dynamics of chemoresistance. We emphasize on the Darwinian evolution process that selects for phenotypically fit populations over the traditional-omics approach, which can be confusing and misleading when many different genotypes can confer phenotypic fitness. We aim to develop a simple but high throughput and easily adoptable single-cell assay, which is the antithesis of traditional single-cell studies that are usually complicated, laborious, extremely low-throughput, and unadoptable. For instance, conventional single-cell approaches such as atomic force microscopy or micropipette studies can take upwards of 1 hour per experiment per cell as well as specialized equipment and high manual labor consumption (Stewart, M. P. et al., Nat. Protocols, 2012. 7(1): p. 143-154; Hochmuth, R. M., Journal of Biomechanics, 2000. 33(1): p. 15-22). Alternatively, using only conventional microscopy to track thousands of single-cell lineages is impractical and computationally intensive.

For our experiments, we will start by assessing the drug-induced responses of the two key phenotypes of metastatic cancer—proliferative capacity and invasiveness, for cells cannot metastasize if they cannot invade and they are not cancerous if they do not proliferate with abandonment. Conventional methods for assessing cell proliferation and invasion responses to drugs primarily consist of transwell plates, extracellular matrix gel models, and the hanging drop and tumor spheroid assays (Timmins, N. et al., Angiogenesis, 2004. 7(2): p. 97-103; Albini, A. et al., Nature Protocols, 2007. 2(3): p. 504-511; Albini, A. et al., Current Opinion in Cell Biology, 2010; Friedl, P. et al., Nature Reviews Cancer, 2003. 3: p. 363-374). These assays are typically simple and compatible with existing large-scale drug screening infrastructures, which make them appealing and enabled their high adoption and usage rates. However, the key drawback of all of these assays is that they are all bulk population studies, which cannot produce the single-cell evolutionary dynamics that drive cancer evolution and resistance (as we discussed previously). There have also been more recent developments in microfluidic assays that enable the study of cell migration in microchannels (Irmia, D. et al., Integrative Biology, 2009. 1: p. 506-512; Rolli, C. G. et al., PLoS ONE, 2010. 5) or can manipulate single cells into geometric patterns or droplets for genomic or proteomic analysis (Rowat, A. C. et al., Proc. Natl. Acad. Sci. USA, 2009. 106: p. 18149-18154; Brouzes, E. et al., Proc. Natl. Acad. Sci. USA, 2009. 106; Shi, Q. et al., Proc. Natl. Acad. Sci. USA, 2012. 2012). However, none of these assays are architecturally designed to elicit both the proliferative and invasive abilities in single-cell lineages and elucidate the fundamental evolutionary dynamics of drug resistance in cancer. Our prior work includes our development of assays and metrics to assess the invasive phenotype in a single-cell and parallel manner.

Here we aim to expand the pharmacologic screening capabilities of this platform and develop an integrated single-cell chemoresistance assay. Specifically, for effective chemotherapeutic drugs, resistant subpopulations and their lineages can be identified based on their proliferation and invasion abilities, both of which can be measured morphometrically and label-free.

As noted, in the proposals described in this example, we aim to integrate an experimental platform, consisting of highly scalable, massively parallel, and user-friendly aspects achievable only through microfluidic techniques, with the concept of cancer cell evolution and drug resistance at the single-cell level. The goal is to innovate a cancer biology assay that can uncover the fundamental evolutionary dynamics and principles that govern chemoresistance and can enable the development of new therapeutic schemes aimed at eliminating the emergence of resistant cancer phenotypes.

As noted above in this example, there are a number of different objectives proposed. Provided below is additional discussion of these objectives, as follows:

Objective 1—Create and Optimize a Simple, Ubiquitously Practicable Assay that Interfaces 1000 Microfluidic Channels with Single-Cell Cancer Biology for the Study of Chemoresistance.

Figure 24:
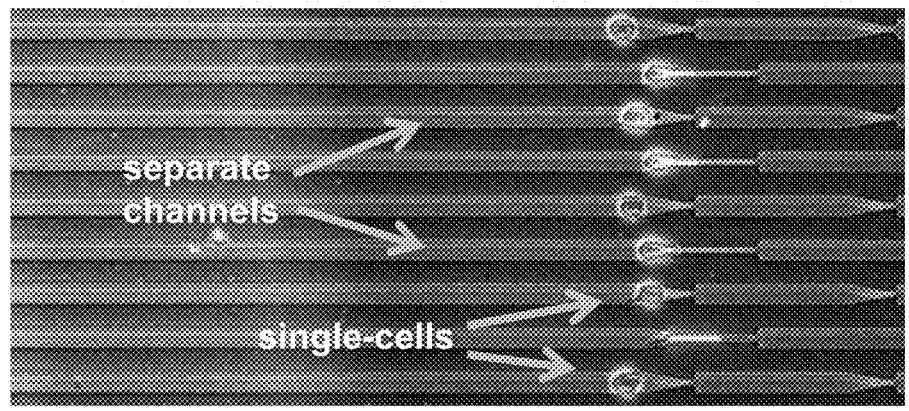
FIG. 24 illustrates increased hydrodynamic resistance due to cell clogging at the subnucleus-scaled channel interface enables one cell to be loaded into each of the parallel microchannels and single-cell proliferation and invasion studies to be performed, as observed in one embodiment of a microfluidic device/microfluidic system of the present invention. Pharmacologic effects can be assessed across single-cell lineages from each channel. Here, only one cell is loaded per channel. This image shows actual single-cells loaded into separate channels using our technique.

We take the minimalist approach in designing this assay in order to maximize adoptability even in biology-oriented and clinical settings. As shown in FIG. 23, the workflow in operating the microfluidic device in performing this assay requires only the pipetting of cells and solutions into the macroscale reservoirs. Single-cell experimental preparation is automated via hydrodynamics—each cell-scaled channel includes constrictions that are smaller than the cell such that an incoming cell would clog the channel at the constriction, inducing infinite hydrodynamic resistance and instantaneously stopping the flow, preventing more cells from entering. This enables each channel in the device to contain only a single cell, so subsequent experiments can be conducted that can resolve the responses of single-cell lineages. In FIG. 24, we show a successfully operating device from our previous work on cell invasion dynamics (Mak, M. et al., Lab on a Chip, 2013. 13(3): p. 340-348) with single-cells loaded across each separate channel.

For our initial design, we will incorporate 1000 single-cell channels in parallel for each device. Existing theories and experiments postulate that there are typically 0.1 to 5% of cells in a bulk tumor that are or will develop chemoresistance (Dean, M. et al., Nat Rev Cancer, 2005. 5(4): p. 275-284; Collins, A. T. et al., Cancer Research, 2005. 65(23): p. 10946-10951; Al-Hajj, M. et al., Proc. Natl. Acad. Sci. USA., 2003. 100: p. 3983-3988; Li, X. et al., Journal of the National Cancer Institute, 2008. 100(9): p. 672-679), so we should be able to collect appreciable data per device. At a channel to channel spacing of 30 µm, this translates into a footprint of only 30 mm per device.

Finite element simulations (from COMSOL) will be used to help design the microfluidic features that will permit the correct streamlines to enable single-cell loading into each chamber. Fabrication of devices will be performed at the Cornell Nanofabrication Facility (CNF). Photolithography and soft lithography will be used for device prototyping for experiments. Specifically, stepper photolithography will be used in preference over contact lithography to enable more repeatable and more refined features to be defined in our chips. With our expertise in nanofabrication and familiarity with all of the relevant tools available at the CNF, we expect to be able to develop an optimal device (in a timely manner with the most effective and efficient fabrication procedures). The result of this step will be an easy to use platform that can be effortlessly interfaced with single-cell lineages and chemotherapeutic testing for an integrated cancer resistance assay.

Objective 2—Track and Analyze Morpho-Metrically the Evolutionary Fitness and Dynamics of Each Single-Cell Lineage Under Chemotherapeutic Treatment.

Understanding the emergence of cell lineages that are chemoresistant can facilitate the development of therapeutic strategies that can target or modulate this critical property.

Current treatments are primarily aimed at targeting the bulk tumor population. This aim is outdated in light of the plethora of work that has demonstrated intra-tumor heterogeneity as a feature of cancer that promotes cancer progression and therapeutic failures. With our device platform, we can perform drug screening at the single-cell level in order to appreciate heterogeneity at the finest level. This will enable us to better identify the heterogeneous responsivity of individual cells to drugs, and the dynamics in the emergence of resistant subpopulations.

Ultimately, this can lead to experimental treatment strategies to test the effects of dosing (concentration and times) and combination chemotherapeutics that have multiple molecular targets (e.g. myosin and microtubules, which are both motor proteins important in cell migration and division) in order to find and optimize key parameters for an anti-resistance regiment. This method of studying drug resistance is advantageous over existing techniques, including animal models, in that it enables a direct visualization of single-cells and their lineages, and the emergence of resistant subpopulations can be visualized directly at its first signs. Other models such as transgenic mice do not easily allow for the tracking of chemoresistance evolution due to the difficulty in tracking individual cells and their dynamics in response to drugs.

In our previous work, we demonstrated the characterization of cell invasive capacity based on measuring the ability of individual cells to permeate across a barrier smaller than the cell nucleus. We showed that when the motor abilities of MDA-MB-231 cells are impaired via microtubule stabilization from the chemotherapeutic Paclitaxel, they can no longer invade, and their super-diffusive migratory behavior is reduced to a random walk as determined by the power-law dependence on time of the mean-squared displacement (see FIG. 6). Additionally, in FIG. 25 we show that distinct motile and morphological phenotypes from single-cells within the same bulk population can be passed on to their individual lineages, illustrating the dynamics of phenotypic diversity. Two different MDA-MB-231 cells, one with a rounded shape and a slow and ruffling motile state and the other with an extended shape with a more polarized motile state, give rise to subsequent progenies that share their initial phenotypes. These findings demonstrate the capabilities of our current generation of devices and metrics in assessing cell invasion, the impact of drug treatment, and single-lineage phenotypic dynamics and diversity—all of which can enable our goal in elucidating the fundamental evolutionary dynamics of drug resistance and metastasis.

Figure 26:
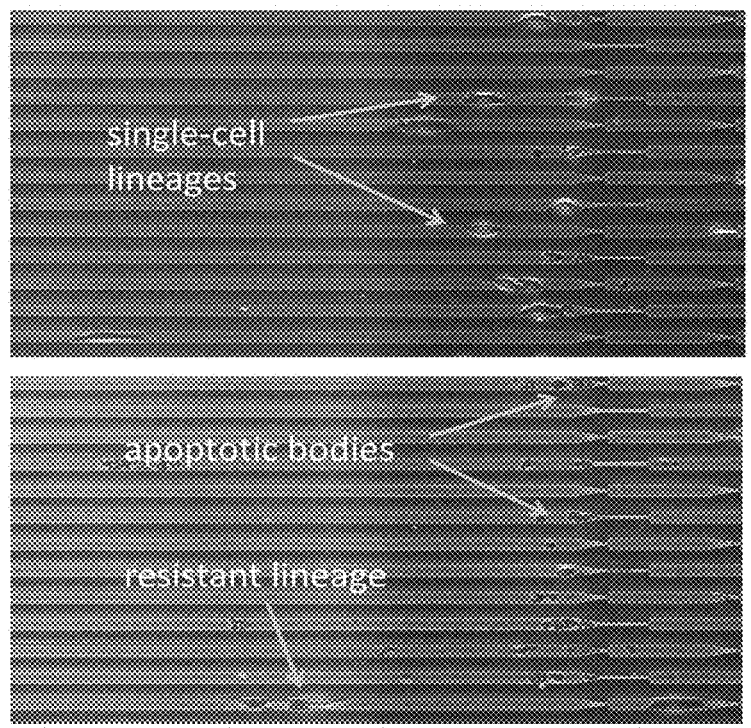
FIG. 26 illustrates breast cancer cells treated with 1 nM Paclitaxel at day 2 (top) and day 6 (bottom) from initial treatment, as observed in one embodiment of a microfluidic device/microfluidic system of the present invention. Cells at the bottom channel remained viable and proliferative, whereas many other cells in other channels underwent apoptosis after failed cell division. This demonstrates a heterogeneous susceptibility of MDA-MB-231 cells to Paclitaxel and the ability of our device and method to distinguish heterogeneity of different single-cell lineages from a common bulk cell population. The emergence of drug resistance can therefore be identified at the single-cell and single-cell lineage level, which can provide better biological resolution and can identify the onset of resistance more quickly especially if only a rare subpopulation of the bulk cells is resistant.

To move forward, we will expand these studies to distinguish the difference in drug responsivity between individual cell lineages enabled by our cell isolation technique previously described, and we will extend the time-scale of these experiments to accommodate for the emergence of drug resistance. In preliminary experiments, we showed that in the course of one week, we can already identify cell lineages that maintain proliferative capacity even under the constant treatment of the anti-mitotic and anti-invasion drug Paclitaxel; many cells underwent apoptosis but a select lineage continues to propagate, as shown in FIG. 26. This demonstrates directly (using the metric of proliferative capacity) the heterogeneous responsivity to drugs and suggests the first signs of resistant phenotypes. For our experiments here, we will continue using MDA-MB-231 cells as a model for metastatic cancer that has demonstrated the ability to develop resistance against Paclitaxel (Wiesen, K. M. et al., Cancer Letters, 2007. 257: p. 227-235).

Our goal is to assess the two key phenotypic traits (u) of metastatic cancer—invasiveness and proliferative capacity. By analyzing how these two properties change over time under chemotherapeutic stress both for the population average $d<u>/dt$ and for each of the isolated single-cell lineages $du/dt$, we can uncover the fundamental evolutionary dynamics in the emergence of chemoresistance. We can then tailor dosing schemes and combinatorial approaches with existing FDA-approved drugs to assess their impact on not only shrinking tumors but also altering and suppressing the onset of resistant behavior. Beyond Paclitaxel, we can continue to expand the library of relevant drugs to be tested that target important aspects of the metastastic cascade, such as pathways involving PI3K, Rho GTPases, and different modes of invasion (mensenchymal, amoeboid, and collective cell behaviors), all of which are targetable by pre-existing pharmacologics. Therefore, we expect to be able to expand the cell-level drug screening process with our technique in order to gauge some of the most relevant features of current cancer research, i.e. heterogeneity and resistance.

Objective 3—Extract Individual Resistant Cell Lineages to Screen for Common Genotypes in Resistant Phenotypes.

The conventional approach in genomics in developing cancer therapies is to screen for differential gene expression between normal cells and cancer cells. Alternatively, when resistant cells are discovered they are screened for their differential expression against the bulk tumor (in addition to normal cells). While these approaches have uncovered the properties of many different cancer cells as well as their resistant counterparts, evolutionary theory states that cancer can simply continue evolving even when such cells are targeted and a new resistant strain will arise. Here, our ability to isolate single-cell lineages in high throughput enables us to assess shared qualities among different resistant subpopulations arising from a common tumor (in addition to the gene expression differentials with the bulk population). By comparing the gene expression profiles across all of the different evolutionarily fit lineages that emerge after therapy, we may uncover potential common genes that promote the ability to develop resistance (to anything) in the first place (rather than any particular resistant phenotype), e.g. stem-like expressions. If such general resistance-inducing precursor genes exist, they would be the ideal anti-resistance targets. However, such genes may not exist or may only exist for certain types of cancers. Nonetheless, our approach here offers a subtle but substantial quality not achievable through existent genomics approaches and may identify the most critical genes of interest. This way we can target genes beyond the ones that are simply the most over-expressed on average or otherwise belong to one of many genotypes that converge towards phenotypic fitness.

To perform these downstream genomics experiments, we simply need to extract the isolated resistant single-cell lineages from our device. This can be accomplished by incorporating separate on-chip outlet reservoirs to collect different lineages. However, because each of our devices has 1000 channels, incorporating separate outlets for each channel would be impractical. Additionally, since only a small percentage of cells (~1% as previously discussed) will develop resistance, it would be inefficient to incorporate 1000 separate outlets. Therefore, we will only make 10 outlet reservoirs for each device, each spanning 100 channels so that on average there would be ~1 resistant lineage per outlet. Cells can then simply be trypsinized and driven out of the channels via pressure driven flow, after which they can be cultured and expanded externally and independently.

Previously, we have extracted cells that invaded across confined spaces in a microfluidic channel and performed a gene expression microarray analysis that demonstrated that mechanically invasive cells differentially express multiple genes, including chemokine receptors such as CCR7 and CXCR4. This demonstrates the ability to extract viable cells from this platform of microfluidic devices and expand them for conventional gene expression profiling. Conventional gene profiling techniques will be used to establish a molecular signature for each of the separate resistant cell lineages. The Agilent Human Gene Expression 44K microarray, available at the Cornell Life Science Core Laboratories Center (CLC), and software analysis using GeneSpring will be the initial tools to use to identify gene expression differentials, and a host of other genomic, epigenomic, and proteomic tools from the CLC can be used for subsequent analyses. Experts at the CLC can aid in the performance of these established assays.

Example 5

Additional Embodiments and Experimental Results

As set forth below, this example describes additional embodiments of the devices, systems, and methods of the present invention and related experimental results.

Figure 27:
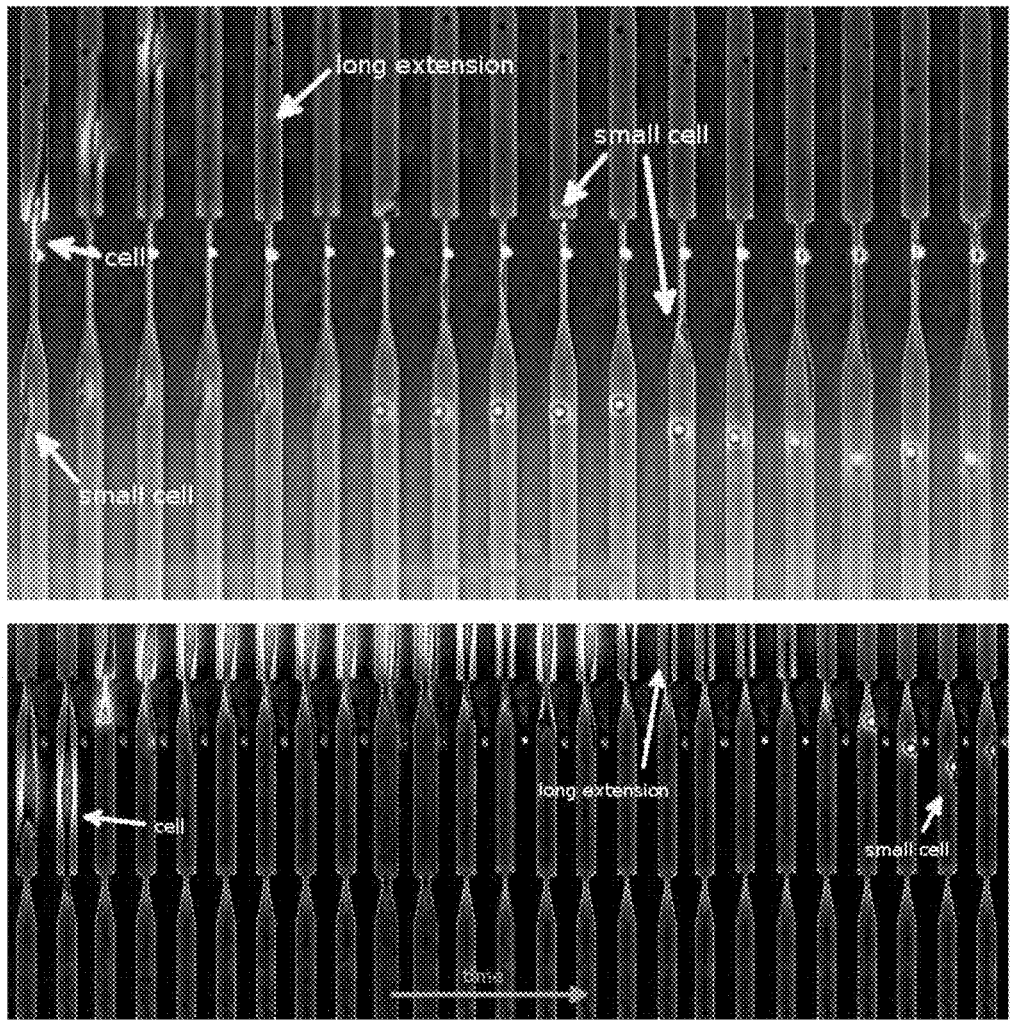
FIG. 27 illustrates cells in one embodiment of a microfluidic device of the present invention, and particularly showing small cell fractionalization from long extensions during invasion across subnucleus barriers.
Figure 28:
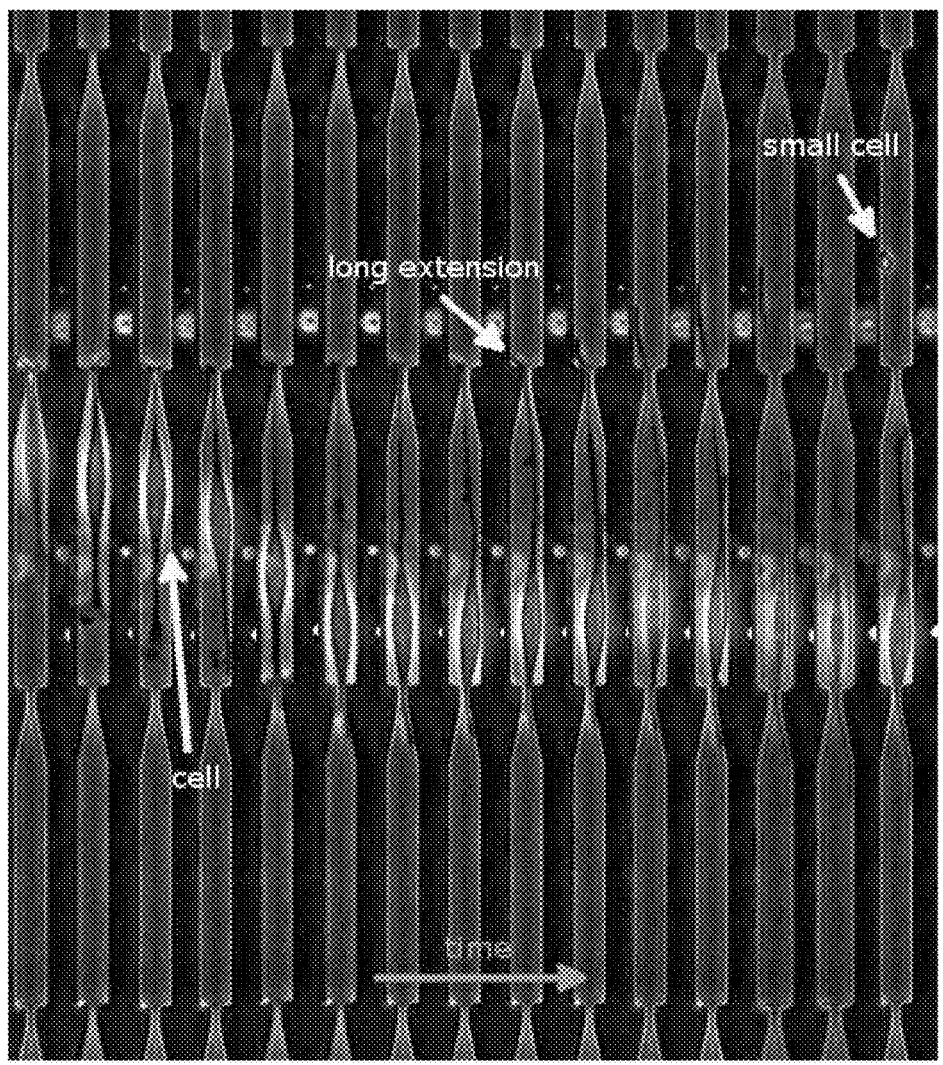
FIG. 28 illustrates cells in one embodiment of a microfluidic device of the present invention, and particularly showing that subnucleus barriers induce cells to protrude long extensions. These extensions sometimes fractionalize into small cells that are capable of moving and protruding their own extensions. 34 minutes elapsed between each frame.

As shown in FIG. 27, in one embodiment of a microfluidic device of the present invention, small cell fractionalization from long extensions during invasion across subnucleus barriers has been observed. As shown in FIG. 28, in one embodiment of a microfluidic device of the present invention, it has been observed that subnucleus barriers induce cells to protrude long extensions. These extensions sometimes fractionalize into small cells that are capable of moving and protruding their own extensions. 34 minutes elapsed between each frame. Thus, as shown in FIGS. 27 and 28, cells exhibit elongated morphologies during invasion across subnucleus barriers, at times their long extensions would fractionalize into small motile fragments. These fragments can continue migrating and invading.

Figure 29A:
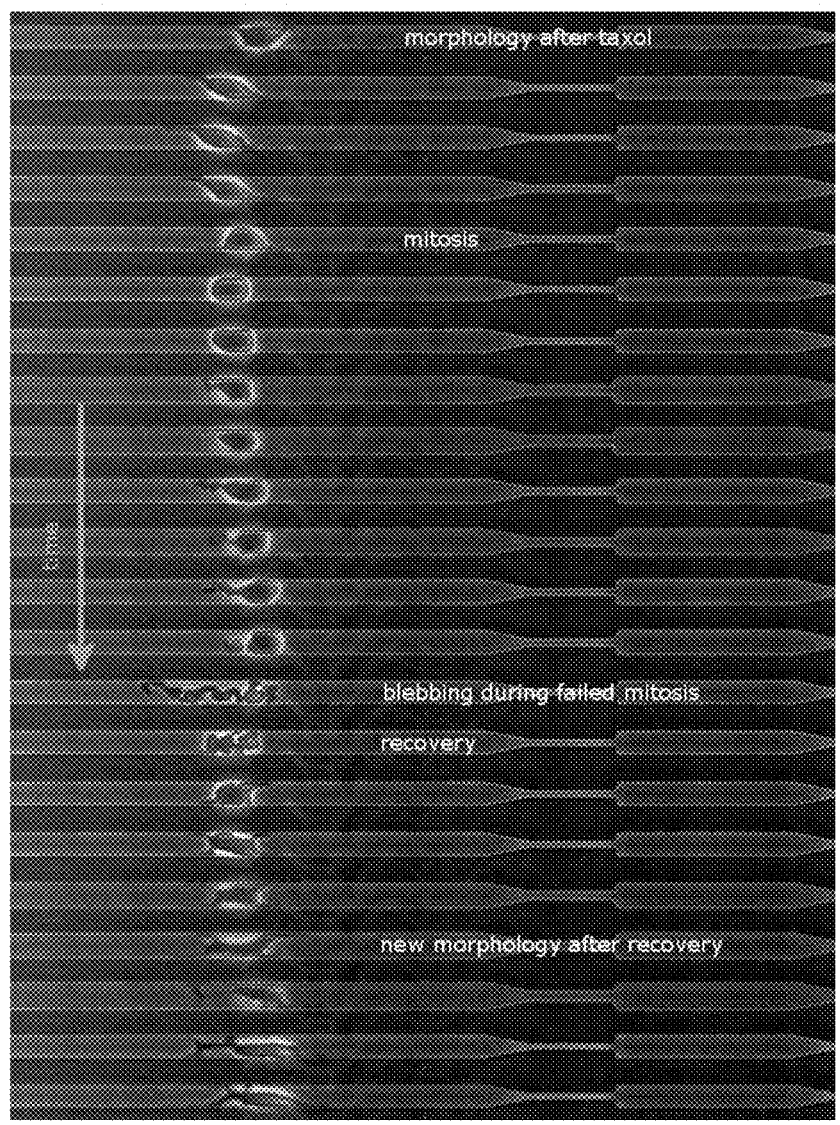
FIGS. 29A-29B illustrate cancer cells treated with the chemotherapeutic taxol in embodiments of a microfluidic device and system of the present invention.
Figure 29B:
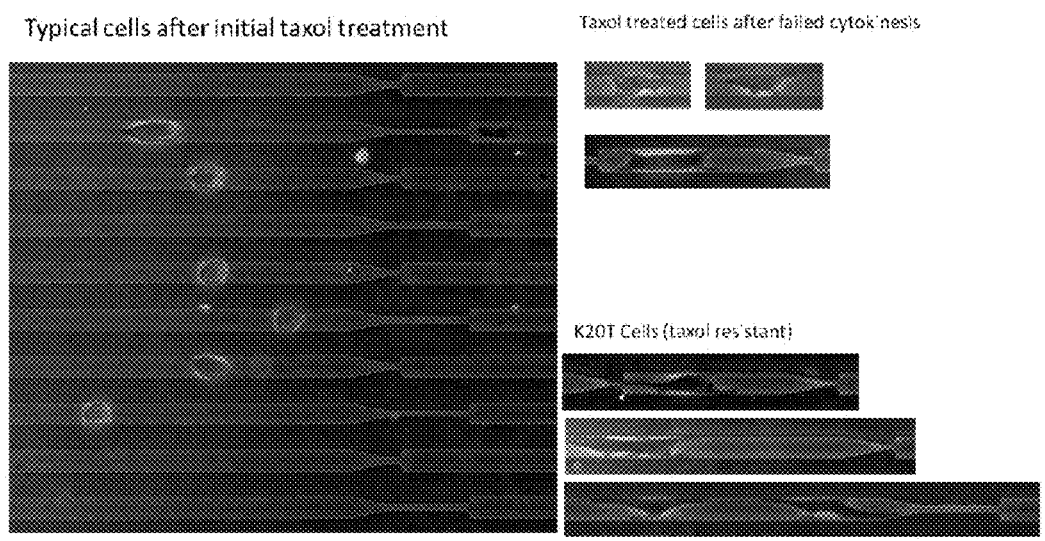

FIGS. 29A-29B show cancer cells treated with the chemotherapeutic taxol in embodiments of a microfluidic device and system of the present invention. In particular, in FIG. 29A, MDA-MB-231 metastatic breast cancer cells treated with the chemotherapeutic taxol exhibit a less extended, more rounded morphology. However, after failed mitosis due to microtubule disruption from taxol, the cells recover a more extended morphology. FIG. 29B shows this more extended morphology from taxol-treated cells after failed mitosis resembles the morphology of K20T cells, which are the taxol-resistant variant of the MDA-MB-231 cells. FIGS. 29A-29B show that, after paclitaxel treatment (taxol) cell morphologies usually take on a more rounded, less extended shape. They also lose the ability to divide properly, resulting in an extensive blebbing phase followed by cytoskeletal recovery. After failed mitosis and recovery, the cells take on a different, more extended morphology, typically with more edges and extensions. This new morphology resembles the taxol-resistant variant of these cells. This could suggest that on an individual cell basis, after failed mitosis, the cell starts to acquire phenotypic features of the drug-resistant variant. For timelapse stacks, 34 minutes elapsed between each frame.

Figure 30:
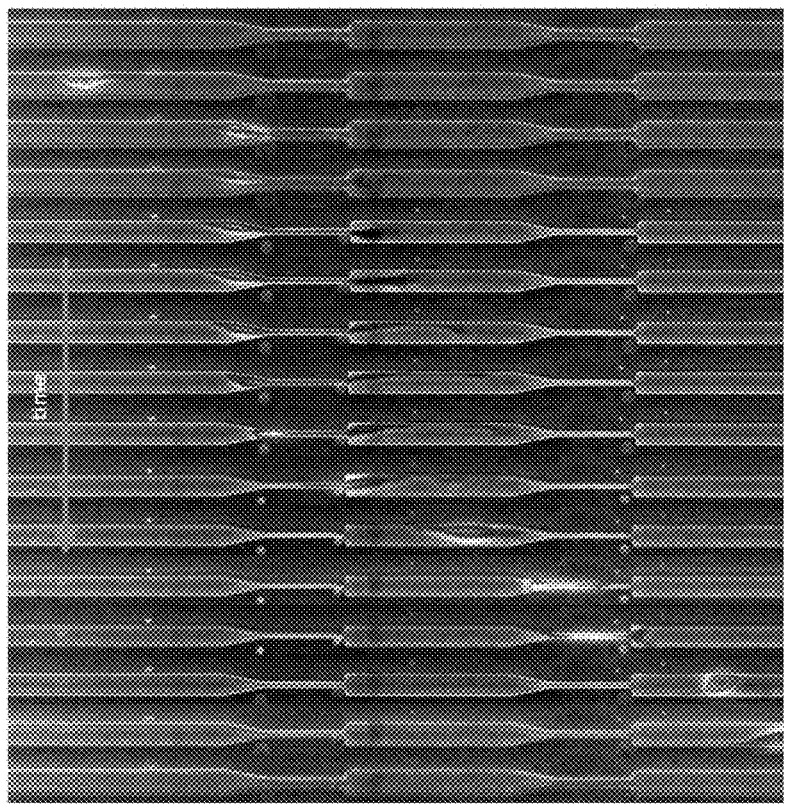
FIG. 30 illustrates a timelapse image stack of a cell invading through a MUlti-tapered Serial Invasion Channel (MUSIC) device.

As shown in FIG. 30, cells invading across subnucleus barriers may exhibit plasticity in invasive modes. This particular cell exhibits an elongated morphology during the invasion across the first subnucleus barrier. The same cell exhibits a substantially less extended morphology on its invasion across the next subnucleus barrier. The MDA-MB-231 cell invaded through 2 mechanical barriers. The first invasion event took 8.4 hrs while the second took only 1.9 hrs. The morphodynamics during invasion between the two events are also different, as one involved much longer protrusions than the other. The MUSIC device enables new single-cell studies of morphological plasticity and transition dynamics across multiple mechanical interfaces. 1.13 hrs elapsed between successive frames.

Figure 31:
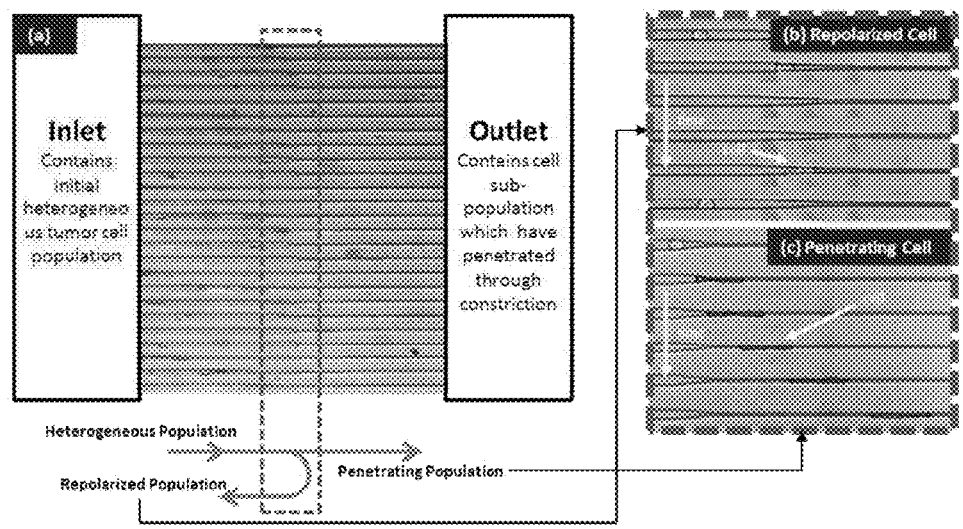
FIG. 31 illustrates one embodiment of a microfluidic device and microfluidic system of the present invention, with the microfluidic channels being in the form of a tapered microchannel assay.

FIG. 31 illustrates one embodiment of a microfluidic device and microfluidic system of the present invention, with the microfluidic channels being in the form of a tapered microchannel assay. Portion (a): Initial heterogeneous population of cells placed in the "inlet" spontaneously crawl through the microchannel array. At the interrogation point (shown here as a constriction) cells either repolarize and return to the initial channel or rearrange their structure and penetrate through. Cells can be collected from the "outlet" for further analysis. Portions (b) and (c): Timelapse montages of cells (b) turning back or repolarizing once reaching the tapered region and (c) permeating into the smaller channel. The cell invasion devices can be used to filter for subpopulations of more invasive cells. An initial heterogeneous tumor cell population is seeded in the inlet and cells are allowed to migrate into the confined microchannels. When the cells reach the interface between the larger microchannel and the smaller microchannel (typically subnucleus-scaled), some cells can permeate into the smaller channel while others cannot and may repolarize (turn around). Cells that permeate into the smaller microchannel and invade into the outlet can be collected and represent a subpopulation of cells that have the ability to persistently invade across highly confined environments. The collected cells can then be cultured separately and/or used in downstream experiments such as genomic profiling. Cells that spend a prolonged period inside the subnucleus-scaled region may exhibit mechanically strained nucleus conformations that could lead to altered gene expression.

Figure 32:
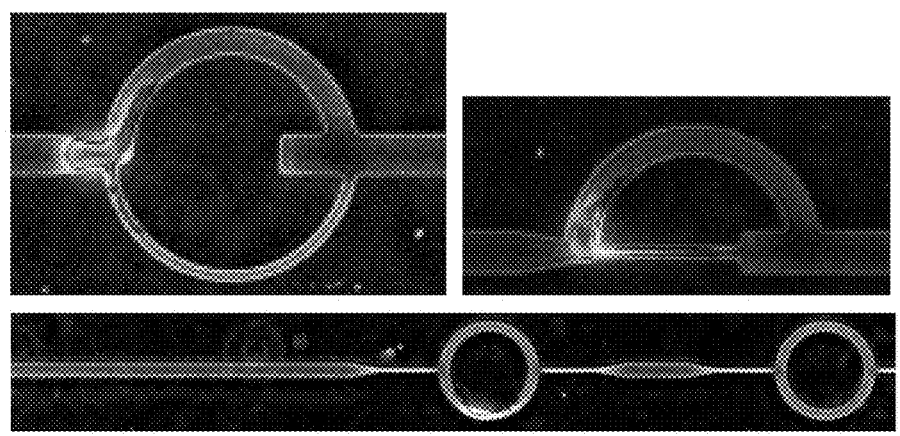
FIG. 32 illustrates cells invading in a confined channel with a split path to probe cell decision making based on mechanical cues during migration and invasion, as observed in one embodiment of a microfluidic device/microfluidic system of the present invention.

As shown in FIG. 32, in one embodiment, the microfluidic channel can be configured to include a confined microchannel with a split path to probe cell decision making based on mechanical cues during migration and invasion. Mechanical features explored are dimensionality (different sized paths) and directionality (relative to the direction of the cell invasion polarization). Our findings show that certain cancer cells, when given split paths with cell-scaled and sub-nucleus-scaled dimensions, will prefer the larger path if the angles of the paths are the same. However, when the direction of one path is close to the original polarized direction of migration of the cell, the cell will then gain preference towards that path. Together, this device can demonstrate the relative importance of mechanical features in biasing or guiding cell decision making during invasion. Ring patterns can then be created that can trap cells inside the ring for an extended period of time, thus modulating cell invasion behavior through manipulating the mechanical microenvironment. These designs can help in uncovering new ways to modulate cell invasion patterns and decision making The larger channel width is 15 µm. The smallest channel has a width of ~3 µm.

As shown in FIG. 32, additional patterns can be incorporated into the original MUSIC device design. Single-cell decision making path trees are incorporated to enable the study of cell migratory behavior when given different paths of different mechanical and geometric properties. Specifically, paths of different sizes (subnucleus-scaled vs. cell-scaled) and different directionality (parallel vs. perpendicular to the cell's original migratory path) are implemented and can probe the mechanical parameters in the local microenvironment that can bias cell migration and invasion behavior. Additionally, cell-scaled ring patterns are incorporated that have an entrance and exit that are subnucleus-scaled in order to impose mechanical asymmetry in the environment. This induces "cell trapping" in the ring region, as cells are forced to migrate for prolonged periods, often in circles, within the ring region.

Citation of a reference herein shall not be construed as an admission that such reference is prior art to the present invention. All references cited herein are hereby incorporated by reference in their entirety.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for tracking at least one cell or cell lineage migrating through a microfluidic channel having single cell-scaled regions and subnucleus-scaled constriction regions, said method comprising:
   (a) providing a microfluidic system comprising a microfluidic device, a cell loading reservoir, and an outlet reservoir,
   wherein said microfluidic device comprises a substrate having one microfluidic channel formed therein or a plurality of microfluidic channels formed therein and arranged in parallel, wherein each microfluidic channel comprises: (i) an inlet end for receiving at least one cell and an accompanying fluidic medium into the microfluidic channel; (ii) an opposing outlet end for dispensing of the fluidic medium flowing from the microfluidic channel and for extracting the at least one cell or a lineage of cells derived from the at least one cell from the microfluidic channel; and (iii) a channel portion comprising a series of at least two alternating single cell-scaled regions and subnucleus-scaled constriction regions disposed between the inlet end and the outlet end, said subnucleus-scaled constriction regions each having a width of between 2 and 4 micrometers (µm),
   wherein said cell loading reservoir is in fluid communication with the inlet end of each microfluidic channel of the microfluidic device,
   wherein said outlet reservoir is in fluid communication with the outlet end of each microfluidic channel of the microfluidic device, and
   wherein a flow path for a fluidic medium runs from the cell loading reservoir through the microfluidic channel and into the outlet reservoir;
   (b) introducing at least one cell or cell lineage into said one microfluidic channel or said plurality of microfluidic channels so that said at least one cell or said lineage of cells migrates into and passes through and past said at least one of the subnucleus-scaled constriction regions in a manner sufficient to cause nucleus deformation of said at least one cell or said lineage of cells due to having to pass through the between 2 and 4 µm width of the subnucleus-scaled constriction regions so as to induce cell transition dynamics, changes in cell morphology, and/or boundary effects on cell division of the at least one cell or cell lineage; and
   (c) viewing the at least one cell or cell lineage as it migrates into and passes through and past at least one of the subnucleus-scaled constriction regions of the microfluidic channel.

2. The method according to claim 1, wherein the introducing step comprises:
   loading a population of cells contained in a fluidic medium into the cell loading reservoir of the microfluidic system under conditions effective to cause at least one cell or multiple cells in close proximity to one another to enter the microfluidic channel through the inlet end of the microfluidic channel and to migrate through the microfluidic channel.

3. The method according to claim 1, wherein the introducing step further comprises:
   generating a flow of the fluidic medium along the flow path of the microfluidic system, said flow path running from the cell loading reservoir through the microfluidic channel and into the outlet reservoir, wherein the flow is maintained for a sufficient amount of time and at a sufficient amount of pressure to induce the cells to migrate through said series of alternating single cell-scaled regions and subnucleus-scaled constriction regions.

4. The method according to claim 3, wherein the flow is generated by establishing a pressure gradient or an electric field along the flow path.

5. The method according to claim 4, wherein the pressure gradient is gravity-based.

6. The method according to claim 3, wherein the flow is either discontinued or maintained after the at least one cell is introduced into the microfluidic channel.

7. The method according to claim 6 further comprising: inducing and maintaining fluidic equilibrium along the flow path after the flow is discontinued.

8. The method according to claim 1, wherein the viewing step comprises observing single cell or single cell lineage behavior during migration into and through the microfluidic channel, wherein said behavior comprises cell invasion, cell migration, cell proliferation, cell deformation, and/or cell response to an introduced agent.

9. The method according to claim 1, wherein multiple cells are introduced into the same microfluidic channel and caused to migrate into and through the microfluidic channel.

10. The method according to claim 1, wherein the at least one cell introduced into the microfluidic channel is caused to, upon coming into contact with one of the subnucleus-scaled constriction regions, temporarily stop for a sufficient amount of time to induce an increase in hydrodynamic resistance in the respective microfluidic channel, thereby preventing additional cells from entering the same microfluidic channel, while allowing individual cells to become loaded in a plurality of other parallel microfluidic channels.

11. The method according to claim 1, wherein viewing the at least one cell or cell lineage comprises using microscopy to observe the at least one cell or cell lineage in contemporaneous real-time or using video microscopy to create real-time videos or static images of the at least one cell or cell-lineage.

12. The method according to claim 1, wherein the at least one cell or cell lineage is viewed migrating through at least one of the single cell-scaled regions and at least one of the subnucleus-scaled constriction regions.

13. The method according to claim 1, wherein the at least one cell or cell lineage is viewed undergoing one or more deformation stage, wherein the deformation stage comprises an initial temporary stoppage of the at least one cell upon meeting at least one of the subnucleus-scaled constriction regions and deformation upon entering and moving along at least one of the subnucleus-scaled constriction regions.

14. The method according to claim 1, wherein a plurality of cells or cell lineages are simultaneously viewed and compared from a plurality of microfluidic channels at substantially the same region of each microfluidic channel in order to observe heterogeneity between the cells or cell lineages.

15. The method according to claim 1, wherein the at least one cell comprises a eukaryotic cell selected from the group consisting of a mammalian cell, a non-mammalian animal cell, a fungal cell, and a plant cell.

16. The method according to claim 1, wherein the at least one cell or cell lineage comprises any primary cancer cell or normal cell from humans, primary cells from animals, and/or cell lines.

17. The method according to claim 1 further comprising: removing unloaded cells from the cell loading reservoir to prevent additional individual cells from entering into a microfluidic channel that already contains an individual cell or individual cell lineage.

18. The method according to claim 1 further comprising: extracting the cells or cell lineages from the microfluidic channels subsequent to viewing their behavior within the microfluidic channels; and
optionally culturing the extracted cells or cell lineages.

19. A method for tracking behavior of at least one cell or cell lineage in response to exposure to an agent of interest, said method comprising:
(a) providing a microfluidic system comprising a microfluidic device, a cell loading reservoir, and an outlet reservoir,
wherein said microfluidic device comprises a substrate having one microfluidic channel formed therein or a plurality of microfluidic channels formed therein and arranged in parallel, wherein each microfluidic channel comprises: (i) an inlet end for receiving at least one cell and an accompanying fluidic medium into the microfluidic channel; (ii) an opposing outlet end for dispensing of the fluidic medium flowing from the microfluidic channel and for extracting the at least one cell or a lineage of cells derived from the at least one cell from the microfluidic channel; and (iii) a channel portion comprising a series of at least two alternating single cell-scaled regions and subnucleus-scaled constriction regions disposed between the inlet end and the outlet end, said subnucleus-scaled constriction regions each having a width of between 2 and 4 micrometers (µm),
wherein said cell loading reservoir is in fluid communication with the inlet end of each microfluidic channel of the microfluidic device,
wherein said outlet reservoir is in fluid communication with the outlet end of each microfluidic channel of the microfluidic device, and
wherein a flow path for a fluidic medium runs from the cell loading reservoir through the microfluidic channel and into the outlet reservoir;
(b) introducing at least one cell or cell lineage into said one microfluidic channel or said plurality of microfluidic channels so that said at least one cell or said lineage of cells migrates into and passes through and past said at least one of the subnucleus-scaled constriction regions in a manner sufficient to cause nucleus deformation of said at least one cell or said lineage of cells due to having to pass through the between 2 and 4 µm width of the subnucleus-scaled constriction regions so as to induce cell transition dynamics, changes in cell morphology, and/or boundary effects on cell division of the at least one cell or cell lineage;
(c) contacting the at least one cell or a cell lineage derived from the at least one cell to an agent of interest; and
(d) viewing the at least one cell or cell lineage in response to the agent as the at least one cell or cell lineage moves through and past at least one of the subnucleus-scaled constriction regions of the microfluidic channel.

20. The method according to claim 19, wherein the agent of interest comprises a drug or drug candidate targeted against the at least one cell or cell lineage.

21. The method according to claim 20, wherein the drug or drug candidate is a chemotherapeutic.

22. The method according to claim 19, wherein viewing the at least one cell or cell lineage comprises using microscopy to observe the at least one cell or cell lineage in contemporaneous real-time or using video microscopy to create real-time videos or static images of the at least one cell or cell-lineage.

23. The method according to claim 19, wherein the at least one cell or cell lineage is viewed undergoing behavior changes in response to the contact with the agent of interest, wherein the behavior changes comprise static and/or dynamic behavior changes.

24. The method according to claim 19 further comprising:
identifying cells that are resistant to intended effects of the agent of interest; and
extracting the identified resistant cells from the microfluidic channels.

25. The method according to claim 19 further comprising: culturing the extracted resistant cells.

* * * * *